US011298358B2

(12) United States Patent
Hoshino et al.

(10) Patent No.: US 11,298,358 B2
(45) Date of Patent: Apr. 12, 2022

(54) COMBINATION THERAPY USING ASCOCHLORIN DERIVATIVE

(71) Applicant: Tatsuo Hoshino, Kanagawa (JP)

(72) Inventors: Tatsuo Hoshino, Kanagawa (JP); Shinji Kagaya, Kanagawa (JP); Nobuo Shimma, Kanagawa (JP); Tsutomu Kawaguchi, Saitama (JP)

(73) Assignee: Tatsuo Hoshino, Kanagawa (JP)

( * ) Notice: Subject to any disclaimer, the term of this patent is extended or adjusted under 35 U.S.C. 154(b) by 296 days.

(21) Appl. No.: 16/613,958

(22) PCT Filed: May 18, 2018

(86) PCT No.: PCT/JP2018/020087
§ 371 (c)(1),
(2) Date: Nov. 15, 2019

(87) PCT Pub. No.: WO2018/212363
PCT Pub. Date: Nov. 22, 2018

(65) Prior Publication Data
US 2021/0346390 A1 Nov. 11, 2021

(30) Foreign Application Priority Data
May 18, 2017 (JP) .............................. JP2017-098860

(51) Int. Cl.
| | | |
|---|---|---|
| *A61K 31/15* | (2006.01) | |
| *A61K 31/155* | (2006.01) | |
| *A61K 31/5375* | (2006.01) | |
| *A61K 31/495* | (2006.01) | |
| *A61K 45/06* | (2006.01) | |
| *A61P 35/00* | (2006.01) | |
| *A61K 31/055* | (2006.01) | |
| *A61K 31/122* | (2006.01) | |
| *A61K 31/215* | (2006.01) | |
| *A61K 31/337* | (2006.01) | |
| *C07K 16/28* | (2006.01) | |

(52) U.S. Cl.
CPC ........ *A61K 31/5375* (2013.01); *A61K 31/055* (2013.01); *A61K 31/122* (2013.01); *A61K 31/15* (2013.01); *A61K 31/215* (2013.01); *A61K 31/337* (2013.01); *A61K 31/495* (2013.01); *A61P 35/00* (2018.01); *C07K 16/2818* (2013.01); *C07K 16/2827* (2013.01)

(58) Field of Classification Search
CPC .. A61K 31/15; A61K 31/155; A61K 31/5375; A61K 31/495; A61K 39/3955; A61K 45/06; C07K 16/2818; C07K 16/2827; C07K 2317/76; A61P 35/00
USPC ..................... 514/764, 763, 238.5
See application file for complete search history.

(56) References Cited

U.S. PATENT DOCUMENTS

| | | | |
|---|---|---|---|
| 5,420,334 | A | 5/1995 | Singh et al. |
| 2006/0247307 | A1 | 11/2006 | Kitahara et al. |
| 2007/0208078 | A1 | 9/2007 | Saimoto et al. |
| 2014/0243378 | A1 | 8/2014 | Draper et al. |

FOREIGN PATENT DOCUMENTS

| | | |
|---|---|---|
| EP | 1176134 A1 | 1/2002 |
| EP | 1616856 A1 | 1/2006 |
| EP | 1762558 A1 | 3/2007 |
| JP | 06305959 A | 11/1994 |
| JP | H09157286 A | 6/1997 |
| JP | 2005112755 A | 4/2005 |
| JP | 2005225851 A | 8/2005 |
| JP | 2006213644 A | 8/2006 |
| WO | 9405274 A1 | 3/1994 |
| WO | 2004074236 A1 | 9/2004 |
| WO | 2007060976 A1 | 5/2007 |
| WO | 2017119515 A1 | 7/2017 |

OTHER PUBLICATIONS

Park, Jun-Young, et al., "Ascofuranone inhibits lipopolysaccharide-induced inflammatory response via NF-kB and AP-1, p-ERK, TNA-a, IL-6 and IL-1B in RAW 264.7 macrophages", PLoS ONE (2017), 12(2), pp. 1-14 (Year: 2017).*
J. M. Shin et al., "Suppression of c-Myc induces apoptosis via an AMPK/mTOR-dependent pathway by 4-O-methyl-ascochlorin in leukemia cells", Apoptosis; vol. 21, No. 5, Feb. 27, 2016, pp. 657-668.
J. Park et al., "Immune checkpoint inhibitors for cancer treatment," Archives of Pharmacal Research; vol. 39, No. 11, Oct. 21, 2016, pp. 1577-1587.
EPO Extended European Search Report corresponding to the EP Application No. 18802154.7; dated Jan. 25, 2021.
A. Nerstedt et al., "AMP-activated protein kinase inhibits IL-6-stimulated inflammatory response in human liver cells by suppressing phosphorylation of signal transducer and activator of transcriptions 3 (STAT3)," Diabetologia, 2010, vol. 53, pp. 2406-2416.
Barbara Cool et al., "Identification and characterization of a small molecular AMPK activator that treats key components of type 2 diabetes and the metabolic syndrome," Cell Metabolism, Jun. 2006, vol. 3, pp. 403-416.
Benoit Viollet et al., "Cellular and molecular mechanisms of metformin: an overview" Clinical Science, Mar. 2012, 122 (6); pp. 253-270.
Clinton M. Hasenour et al., "Emerging Role of AMP activated Protein Kinase in Endocrine Control of Metabolism in the LIver" Molecular and Cellular Endocrinology, Feb. 25, 2013 vol. 366(2); pp. 152-162.

(Continued)

*Primary Examiner* — Joseph R Kosack
*Assistant Examiner* — Sagar Patel
(74) *Attorney, Agent, or Firm* — Cantor Colburn LLP

(57) ABSTRACT

An object of the present invention is to provide a measure for treating or preventing a disease or condition that involves AMPK dysregulation, particularly a cancer. The present invention provides a combination therapy using a compound presented by formula (I), a pharmaceutically acceptable salt or a solvate thereof with an immune checkpoint inhibitor.

13 Claims, 2 Drawing Sheets

(56) References Cited

OTHER PUBLICATIONS

D. Grahame Hardie, et al., "AMPK—a nutrient and energy sensor that maintains energy homeostasis," Nature Reviews/Molecular Cell Biology, Author manuscript available in PMC Dec. 2017, vol. 13 pp. 251-262.
Gregory R. Steinberg et al., "AMPK in Health and Disease," Physiological Rev. 2009, vol. 89, pp. 1025-1078.
Hayley M. O'Neill et al., AMPK regulation of fatty acid metabolism and mitochondrial biogenesis: Implications for obesity,: Molecular and Cellular Endocrinology, 2013, vol. 366; pp. 135-151.
Heberty T. F. Facundo et al., AMPK Activators: Not Just for Diabetes? Circ Res., 2009, 104 (3), pp. 282-284.
International Search Report corresponding to Application No. PCT/JP2018/020087; dated Jul. 24, 2018.
Ji-Hak Jeong et al., "4-0-methylascochlorin, methylated derivative of ascochlorin, stabilizes HIF-1x via AMPK activaiton," Biochemical and Biophysical Research Communications, 2011, vol. 406, pp. 353-358.
Maria M. Mihaylova, et al., "The AMP-activated protein kinase (AMPK) signaling pathway coordinates cell growth, autophagy, & metabolism," Nature Cell Biology, 2011, vol. 13 (9), pp. 1016-1023.
Michael M. Myerburg et al., AMPK Agonists Ameliorate Sodium and Fluid Transport and Inflammation in Systic Fibrosis Airway Epithelia Cells, Am. J Respir. Cell Mol. Biol., 2010, vol. 42, pp. 676-684.
Neil B. Ruderman et al., "AMPK, insulin resistance, and the metabolic syndrome," The Journal of Clinical Investigation, Jul. 2013, vol. 123 No. 7, pp. 2764-2772.
Nicole E. Scharping et al., "Efficacy of PD-1 Blockade Is Potentiated by Metformin-Induced Reduction of Tumor Hypoxia," Cancer Immunology Research, Jan. 2017; 5(1), pp. 9-16.
Nikolaos Tezapsidis et al., "Leptin: A Novel Therapeutic Strategy for Alzheimer's Disease," J Alzheimers Disease., Apr. 2009, vol. 16(4), pp. 731-740.
Richard M. Reznick et al., "The role of AMP-activated protein kinase in mitochondrial biogenesis," J. Physiol., 2006, vol. 574.1 pp. 33-39.
Weidong Li et al., "Targeting AMPK for cancer prevention and treatment," Oncotarget, 2015, vol. 6 No. 10, pp. 7365-7378.
International Search Report corresponding to International Application No. PCT/JP2017/000902; dated Feb. 21, 2017.
The extended European Search Report corresponding to the EP Application No. 17736052.6; dated Sep. 11, 2019.
JPO Office Action for corresponding JP Application No. 2018-553638; dated Jun. 5, 2020.
Saimoto et al., "Pharmacophore identification of ascofuranone, potent, inhibitor of cyanide-insensitive alternative oxidase of Trypanosoma brucei", The Journal of Biochemistry, vol. 153(3):267-273, doi:10.1093/jb/mvs135; (Published Nov. 23, 2012), 7 pages.
Wanigesekara et al. "10'-Deoxy-10' [alpha]-hydroxyascochlorin, a New Cell Migration Inhibitor and Other Metabolites from *Acremonium* sp., a Fungal Endophyte in Ephedra trifurca". Natural Product Communications, vol. 8, No. 5; Dated (Mar. 4-21, 2013);pp. 601-604.
CNIPA Office Action for corresponding CN Application No. 201880032981.4, dated Apr. 1, 2021.
Stewart et al., "Identification and Characterization of MEDI4736, an Antagonistic anti_PD-L1 Monoclonal Antibody", Cancer Immunology Research, vol. 3, No. 9, May 5, 2015; 38 pages.

* cited by examiner

COMBINATION THERAPY USING ASCOCHLORIN DERIVATIVE

CROSS REFERENCE TO RELATED APPLICATIONS

This application is the U.S. national stage of PCT/JP2018/020087, filed on May 18, 2018, which claims priority under 35 U.S.C. § 119(a) and 35 U.S.C. § 365(b) to Japanese Patent Application No. 2017-098860, filed May 18, 2017, the contents of which are incorporated herein by reference in their entirety.

TECHNICAL FIELD

The present invention is directed to a combination therapy using an ascochlorin derivative with an immune check point inhibitor. The invention is also directed to a pharmaceutical composition comprising an ascochlorin derivative, for use in combination with administration of an immune check point inhibitor.

BACKGROUND ART

The adenosine monophosphate-activated protein kinase (AMPK) is an important regulatory protein for cellular energy balance and is considered as a master switch of glucose and lipid metabolisms in various organs, especially in skeletal muscle, liver and fat tissue.

AMPK is also known to have critical roles in regulating cell growth and autophagy through inhibition of m-TOR, as well as mitochondrial biogenesis [*Physiological Rev.* 2009, vol. 89, page 1025, *Nature Reviews/Molecular Cell Biology*, 2012, vol. 13 page 251, *Nature Cell Biology*, 2011, vol. 13 (9), 1016, *Molecular and Cellular Endocrinology*, 2013 vol. 366, page 152, *J. Physiol.*, 2006, vol 574.1 page 33.].

When intracellular ATP levels become lower, AMP or ADP can directly bind to the ☐ regulatory subunit of AMPK, leading to a conformational change that promotes AMPK phosphorylation at Thr172 by LKB1 (known as a tumor suppressor) or CAMKK2 ($Ca^{++}$ dependent kinase). Further, the conformational change also protects AMPK from dephosphorylation by protein phosphatases 2A and C so that AMPK remains activated.

The dysregulation of AMPK is considered as a pathogenic factor for the diseases such as cancer, type 2 diabetes, metabolic syndrome-associated diseases (dyslipidemia, adiposity, atherosclerotic cardiovascular disease, hypertension, and nonalcoholic fatty liver disease (NAFLD)), inflammation and Alzheimer disease, and thus AMPK is considered as a target for the prevention and therapy of these diseases [metabolic syndrome: *The Journal of Clinical Investigation*, 2013, Vol. 123 (7) page 2764, *Molecular and Cellular Endocrinology*, 2013, vol. 366 page 135; cancer and inflammation: *Oncotarget*, 2015, vol. 6 (10), page 7365; cardiovascular disease: *Circ Res.*, 2009 vol. 104 (3), page 282; inflammation, *Diabetologia*, 2010 vol. 53, page 2406, *Am. J. Respir. Cell Mol. Biol.*, 2010, vol 42, page 676; Alzheimer disease: *J Alzheimers Dis.* 2009, vol. 16(4) page 731].

Metformin is known as an antihyperglycemic agent to indirectly activate AMPK through inhibition of respiratory chain complex 1 [*Clinical Science*, 2012, vol. 122, page 253]. Metformin, however, is reported to activate AMPK in HepG2 cell only at surprisingly high concentration of mM level for in vitro cellular experiment.

5-Aminoimidazole-4-carboxamide ribonucleotide (AICAR) is known as an AMP mimic. AICAR directly activates AMPK through binding to a regulatory ☐-subunit to promote phosphorylation of AMPK and to protect AMPK from dephosphorylation. A-769662 is reported to be a direct AMPK-activator with a different binding mode, [*Cell Metabolism*, 2006, vol. 3, page 403]. There are other AMPK-activators reported in literatures, but none of them is clinically used up to now, partly because of the insufficient in vivo efficacy and/or safety profile. Therefore, novel AMPK activators with good efficacy and safety profile would provide therapeutic benefits to the patients with diseases that involve AMPK dysregulations.

4-O-Methy-ascochlorin (MAC) is a derivative of a fungal metabolite of ascochlorin, which is reported to have ability for activating AMPK in HepG2 cells [*Biochemical and Biophysical Research Communications*, 2011, vol. 406, page 353]. 4-O-Substituted ascochlorin derivatives including MAC are described as an antidiabetic agent in JP H06-305959 A (published in 1994), and prodrugs of MAC that are Schiff base derivatives formed with natural amino acids are described in WO2004/074236. However, the development of any ascochlorin derivatives has not become successful.

Immune checkpoint inhibitors are known as molecules that block signaling in the immune system to stimulate or inhibit the immune system. It has been well known that many cancers protect themselves from the immune system by inhibiting the T cell signal. Immune checkpoint system, particularly the system involving CTLA4 (cytotoxic T-lymphocyte-associated protein 4), PD-1 (programmed cell death 1), PD-L1 (programmed cell death ligand-1), and the like is considered as targets for cancer immunotherapies, and the immune check point inhibitors are considered as applicable to treatment of cancers. As the immune checkpoint inhibitor, one anti-CTLA4 antibody, ipilimumab (Bristol-Myers Squibb); two anti-PD-1 antibody, nivormab (Bristol-Myers Squibb) and pembrolizumab (Merck); and one PD-L1 antibody, atezolizumab (Roche) were already launched to initially apply to advanced melanoma or urothelial carcinoma.

Combination therapies are widely used by practitioners for treating serious diseases including a cancer. A report was made for combination of anti-PD-1 antibody with metformin for treating a cancer (Cancer Immunol. Res., 2017 January; 5(1), 9-16).

CITATION LIST

Patent Documents

Patent Document 1: JP H06-305959 A;
Patent Document 2: WO 2004/074236

Non-Patent Documents

Non-Patent Document 1: Physiological Rev. 2009, vol. 89, page 1025,
Non-Patent Document 2: Nature Reviews/Molecular Cell Biology, 2012, vol. 13 page 251,
Non-Patent Document 3: Nature Cell Biology, 2011, vol. 13 (9), 1016,
Non-Patent Document 4: Molecular and Cellular Endocrinology, 2013 vol. 366, page 152,
Non-Patent Document 5: J. Physiol., 2006, vol 574.1 page 33
Non-Patent Document 6: The Journal of Clinical Investigation, 2013, 123 (7), 2764;
Non-Patent Document 7: Mol. Cell. Endocrinol., 2013, 366; 135;

Non-Patent Document 8: Oncotarget, 2015, 6 (10), 7365;
Non-Patent Document 9: Circ Res., 2009, 104 (3), page 282;
Non-Patent Document 10: Diabetologia, 2010, 53, 2406;
Non-Patent Document 11: Am. J. Respir. Cell Mol. Biol., 2010, 42, 676;
Non-Patent Document 12: J Alzheimers Dis. 2009, 16(4), 731;
Non-Patent Document 13: Clinical Science, 2012, 122, 253;
Non-Patent Document 14: Cell Metabolism, 2006, 3, 403.
Non-Patent Document 15: Biochemical and Biophysical Research Communications, 2011, vol. 406, page 353
Non-Patent Document 16: Cancer Immunol. Res., 2017 January; 5(1), 9-16.

SUMMARY OF INVENTION

Technical Problem

The present inventors produced ascochlorin derivatives, which are confirmed to have AMPK activation profile, and significantly improved metabolic stability as compared with MAC (PCT application: PCT/JP2017/000902). Particularly, the inventors found that the ascochlorin derivatives also show good in vivo efficacy in several disease models especially for oncology and metabolic diseases. On the other hand, there are strong needs for measures to treat or prevent a certain number of diseases including a cancer.

Solution to Problem

The present inventors have conducted diligent studies and consequently completed the present invention by finding that a combination of an ascochlorin derivative with an immune check point inhibitor has an excellent effect for treating or preventing one of diseases including a cancer.

The present invention is directed to a combination therapy using an ascochlorin derivative with an immune checkpoint inhibitor for treating or preventing at least one disease including a cancer. The invention is also directed to a pharmaceutical composition comprising an ascochlorin derivative for use in combination with administration of an immune checkpoint inhibitor for treating or preventing at least one disease including a cancer.

According to one aspect of the present invention, there is provided the following inventions:

(1-1) A pharmaceutical composition comprising a compound represented by formula (I):

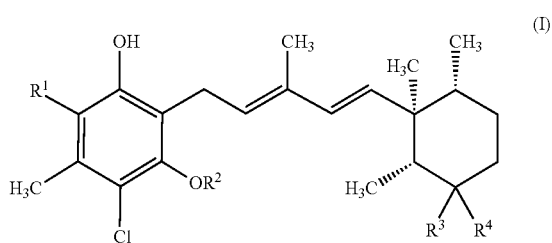

wherein
$R^1$ is formyl, or —CH=N—O—Y, in which Y is a hydrogen atom or $C_{1-6}$ alkyl;
$R^2$ is $C_{1-6}$ alkyl, in which the alkyl may be substituted with one to five fluorine atoms;
$R^3$ is a hydrogen atom or $C_{1-6}$ alkyl;

$R^4$ is hydroxy, $C_{1-6}$ alkylamino, $C_{3-7}$ cycloalkylamino, or 3- to 7-membered heterocycloalkylamino which contains —O—, —S—, —$NR^6$—, —SO— or —$SO_2$— as a ring atom, or $R^3$ and $R^4$ together with the carbon atom to which they are attached form >C=N—O—Z;
Z is a hydrogen atom, $C_{1-6}$ alkyl, —$CO(CH_2)_n$—$R^5$ or —$(CH_2)_n$—$R^5$;
n is an integer selected from 1 to 4;
$R^5$ is —$CO_2R^6$, —$CONR^7R^8$, —$OCONR^7R^8$, —$SO_2NR^7R^8$, —$SO_2R^9$, hydroxy, —$NHSO_2R^9$, or —$NR^7R^8$;
$R^6$, $R^7$ and $R^8$ are each independently selected from a group consisting of a hydrogen atom, $C_{1-6}$ alkyl, and $C_{3-7}$ cycloalkyl; or $R^7$ and $R^8$ together with the nitrogen atom to which they are attached form a nitrogen containing heterocyclic ring which may further contain —O—, —S—, —$NR^6$—, —SO— or —$SO_2$— as a ring atom, in which the heterocyclic ring may be substituted with one or more substituents selected from hydroxy and $C_{1-6}$ alkyl,
$R^9$ is $C_{1-6}$ alkyl, or $C_{3-7}$ cycloalkyl;
a pharmaceutically acceptable salt or a solvate thereof,
wherein the composition is for use in combination with administration of an immune checkpoint inhibitor.

(1-2) The pharmaceutical composition according to (1-1), wherein $R^4$ is selected from the group consisting of hydroxy, methylamino, ethylamino, cyclopropylamino, and oxetan-3-ylamino.

(1-3) The pharmaceutical composition according to (1-1), wherein $R^3$ and $R^4$ together with the carbon atom to which they are attached form >C=N—O—Z in which Z is selected from the group consisting of a hydrogen atom, $C_{1-6}$ alkyl, —$CH_2CO_2H$, —$CH_2CO_2R^5$, morpholinoethyl, piperazinylethyl, N-methyl-piperazinylethyl, and N,N-dimethylamino-ethyl.

(1-4) The pharmaceutical composition according to (1-2) or (1-3), wherein $R^1$ is formyl.

(1-5) The pharmaceutical composition according to (1-2) or (1-3), wherein $R^1$ is —CH=N—OH.

(1-6) The pharmaceutical composition according to (1-2) or (1-3), wherein $R^1$ is —CH=N—OMe.

(1-7) The pharmaceutical composition according to (1-1), wherein the compound represented by formula (I) is selected from the group consisting of
3-chloro-6-hydroxy-5-((2E,4E)-5-((1R,2R,6R)-3-hydroxy-1,2,3,6-tetramethylcyclohexyl)-3-methylpenta-2,4-dien-1-yl)-4-methoxy-2-methylbenzaldehyde,
3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde,
(E)-3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde oxime,
3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde oxime,
3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde,
[(1E,2R,3R,4R)-3-[(1E,3E)-5-(3-chloro-5-formyl-6-hydroxy-2-methoxy-4-methylphenyl)-3-methylpenta-1,3-dien-1-yl]-2,3,4-trimethylcyclohexylidene]amino 2-(dimethylamino)acetate,
(E)-3-chloro-6-hydroxy-5-((2E,4E)-5-((1R,2R,3S,6R)-3-hydroxy-1,2,3,6-tetramethylcyclohexyl)-3-methylpenta-2,4-dien-1-yl)-4-methoxy-2-methylbenzaldehyde oxime, (E)-3-chloro-6-hydroxy-4-methoxy-5-((2E,4E)-5-((1R,2R,6R,E)-3-(methoxyimino)-1,2,6-trimethylcyclohexyl)-3-methylpenta-2,4-dien-1-yl)-2-methylbenzaldehyde O-methyl oxime,
(E)-3-chloro-4-(fluoromethoxy)-6-hydroxy-5-((2E,4E)-5-((1R,2R,6R,E)-3-(methoxyimino)-1,2,6-trimethylcyclohexyl)-3-methylpenta-2,4-dien-1-yl)-2-methylbenzaldehyde O-methyl oxime,
(E)-3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde O-methyl oxime,
(E)-3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde O-methyl oxime,
3-chloro-4-(fluoromethoxy)-6-hydroxy-2-methyl-5-((2E,4E)-3-methyl-5-((1R,2R,6R,E)-1,2,6-trimethyl-3-(2-morpholinoethoxyimino)cyclohexyl)penta-2,4-dien-1-yl)benzaldehyde,
3-chloro-5-((2E,4E)-5-((1R,2R,6R)-3-(cyclopropylamino)-1,2,6-trimethylcyclohexyl)-3-methylpenta-2,4-dien-1-yl)-4-(fluoromethoxy)-6-hydroxy-2-methylbenzaldehyde,
(E)-3-chloro-6-hydroxy-5-((2E,4E)-5-((1R,2R,3S,6R)-3-hydroxy-1,2,3,6-tetramethylcyclohexyl)-3-methylpenta-2,4-dien-1-yl)-4-methoxy-2-methylbenzaldehyde O-methyl oxime,
(E)-3-chloro-5-((2E,4E)-5-((1R,2R,6R,E)-3-(2-(dimethylamino)ethoxyimino)-1,2,6-trimethylcyclohexyl)-3-methylpenta-2,4-dien-1-yl)-6-hydroxy-4-methoxy-2-methylbenzaldehyde O-methyl oxime,
(E)-3-chloro-6-hydroxy-4-methoxy-2-methyl-5-((2E,4E)-3-methyl-5-((1R,2R,6R,E)-1,2,6-trimethyl-3-(2-morpholinoethoxyimino)cyclohexyl)penta-2,4-dien-1-yl)benzaldehyde O-methyl oxime,
(E)-3-chloro-6-hydroxy-4-methoxy-2-methyl-5-((2E,4E)-3-methyl-5-((1R,2R,6R,E)-1,2,6-trimethyl-3-(2-(4-methylpiperazin-1-yl)ethoxyimino)-cyclohexyl)penta-2,4-dien-1-yl)benzaldehyde O-methyl oxime,
ethyl 2-([[[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetate,
2-([[[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetic acid,
3-chloro-5-((2E,4E)-5-((1R,2R,6R)-3-(ethylamino)-1,2,6-trimethylcyclohexyl)-3-methylpenta-2,4-dien-1-yl)-6-hydroxy-4-methoxy-2-methylbenzaldehyde,
(E)-3-chloro-5-((2E,4E)-5-((1R,2R,6R)-3-(ethylamino)-1,2,6-trimethylcyclohexyl)-3-methylpenta-2,4-dien-1-yl)-6-hydroxy-4-methoxy-2-methylbenzaldehyde O-methyl oxime,
3-chloro-5-((2E,4E)-5-((1R,2R,6R)-3-(cyclopropylamino)-1,2,6-trimethylcyclohexyl)-3-methylpenta-2,4-dien-1-yl)-6-hydroxy-4-methoxy-2-methylbenzaldehyde,
(E)-3-chloro-5-((2E,4E)-5-((1R,2R,6R)-3-(cyclopropylamino)-1,2,6-trimethylcyclohexyl)-3-methylpenta-2,4-dien-1-yl)-6-hydroxy-4-methoxy-2-methylbenzaldehyde O-methyl oxime,
2-[(2E,4E)-5-[(1R,2R,6R)-3-amino-1,2,6-trimethylcyclohexyl]-3-methylpenta-2,4-dien-1-yl]-4-chloro-3-methoxy-6-[(1E)-(methoxyimino)methyl]-5-methylphenol,
(E)-3-chloro-6-hydroxy-4-methoxy-2-methyl-5-((2E,4E)-3-methyl-5-((1R,2R,6R)-1,2,6-trimethyl-3-(oxetan-3-ylamino)cyclohexyl)penta-2,4-dien-1-yl)benzaldehyde O-methyl oxime,
2-([[[(1E,2R,3R,4R)-3-[(1E,3E)-5-[3-chloro-6-hydroxy-2-fluoromethoxy-5-formyl-4-methylphenyl]-3-methylpenta-1,3-dien-1-yl]-2,3,4-trimethylcyclohexylidene]amino]oxy)acetic acid,
2-([[[(1E,2R,3R,4R)-3-[(1E,3E)-5-[3-chloro-6-hydroxy-2-methoxy-5-[(1E)-(hydroxyimino)methyl]-4-methylphenyl]-3-methylpenta-1,3-dien-1-yl]-2,3,4-trimethylcyclohexylidene]amino]oxy)acetic acid,
2-([[[(1E,2R,3R,4R)-3-[(1E,3E)-5-[3-chloro-2-methoxy-6-hydroxy-5-[(1E)-(hydroxyimino)methyl]-4-methylphenyl]-3-methylpenta-1,3-dien-1-yl]-2,3,4-trimethylcyclohexylidene]amino]oxy)acetic acid,
and pharmaceutically acceptable salts thereof.

(1-8) The pharmaceutical composition according to any one of (1-1) to (1-7), wherein the immune checkpoint inhibitor is selected from anti-CTLA4 antibodies, anti-PD-1 antibodies and anti-PD-L1 antibodies.

(1-9) The pharmaceutical composition according to any one of (1-1) to (1-7), wherein the composition is for use in treating or preventing a cancer.

(1-10) The pharmaceutical composition according to any one of (1-1) to (1-7), wherein the immune checkpoint inhibitor is an anti-PD-1 antibody.

(1-11) The pharmaceutical composition according to any one of (1-1) to (1-7), wherein the immune checkpoint inhibitor is an anti-PD-L1 antibody.

(1-12) The pharmaceutical composition according to any one of (1-1) to (1-11), wherein the immune checkpoint inhibitor is administered in amount of 0.1 to 200 mg/kg/day.

(1-13) The pharmaceutical composition according to any one of (1-1) to (1-12), wherein the compound represented by formula (I) is administered in amount of 1 to 500 mg/kg/day.

(2-1) A pharmaceutical composition comprising an immune checkpoint inhibitor for use in combination with administration of a compound represented by formula (I):

wherein
$R^1$ is formyl, or —CH=N—O—Y, in which Y is a hydrogen atom or $C_{1-6}$ alkyl;
$R^2$ is $C_{1-6}$ alkyl, in which the alkyl may be substituted with one to five fluorine atoms;
$R^3$ is a hydrogen atom or $C_{1-6}$ alkyl;
$R^4$ is hydroxy, $C_{1-6}$ alkylamino, $C_{3-7}$ cycloalkylamino, or 3- to 7-membered heterocycloalkylamino which contains —O—, —S—, —$NR^6$—, —SO— or —$SO_2$— as a ring atom, or $R^3$ and $R^4$ together with the carbon atom to which they are attached form >C=N—O—Z;
Z is a hydrogen atom, $C_{1-6}$ alkyl, —CO($CH_2$)$_n$—$R^5$ or —($CH_2$)$_n$—$R^5$;
n is an integer selected from 1 to 4;

R⁵ is —CO₂R⁶, —CONR⁷R⁸, —OCONR⁷R⁸, —SO₂NR⁷R⁸, —SO₂R⁹, hydroxy, —NHSO₂R⁹, or —NR⁷R⁸;

R⁶, R⁷ and R⁸ are each independently selected from a group consisting of a hydrogen atom, C₁₋₆ alkyl, and C₃₋₇ cycloalkyl; or R⁷ and R⁸ together with the nitrogen atom to which they are attached form a nitrogen containing heterocyclic ring which may further contain —O—, —S—, —NR⁶—, —SO— or —SO₂— as a ring atom, in which the heterocyclic ring may be substituted with one or more substituents selected from hydroxy and C₁₋₆ alkyl, R⁹ is C₁₋₆ alkyl, or C₃₋₇ cycloalkyl;

a pharmaceutically acceptable salt or a solvate thereof.

(2-2) The pharmaceutical composition according to (2-1), wherein R⁴ is selected from the group consisting of hydroxy, methylamino, ethylamino, cyclopropylamino, and oxetan-3-ylamino.

(2-3) The pharmaceutical composition according to (2-1), wherein R³ and R⁴ together with the carbon atom to which they are attached form >C=N—O—Z in which Z is selected from the group consisting of a hydrogen atom, C₁₋₆ alkyl, —CH₂CO₂H, —CH₂CO₂R⁵, morpholinoethyl, piperazinylethyl, N-methyl-piperazinylethyl, and N,N-dimethylamino-ethyl.

(2-4) The pharmaceutical composition according to (2-2) or (2-3), wherein R¹ is formyl.

(2-5) The pharmaceutical composition according to (2-2) or (2-3), wherein R¹ is —CH=N—OH.

(2-6) The pharmaceutical composition according to (2-2) or (2-3), wherein R¹ is —CH=N—OMe.

(2-7) The pharmaceutical composition according to (2-1), wherein the compound represented by formula (I) is selected from the group consisting of 3-chloro-6-hydroxy-5-((2E,4E)-5-((1R,2R,6R)-3-hydroxy-1,2,3,6-tetramethylcyclohexyl)-3-methylpenta-2,4-dien-1-yl)-4-methoxy-2-methylbenzaldehyde, 3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde, (E)-3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde oxime, 3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde oxime, 3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde,

[(1E,2R,3R,4R)-3-[(1E,3E)-5-(3-chloro-5-formyl-6-hydroxy-2-methoxy-4-methylphenyl)-3-methylpenta-1,3-dien-1-yl]-2,3,4-trimethylcyclohexylidene]amino 2-(dimethylamino)acetate, (E)-3-chloro-6-hydroxy-5-((2E,4E)-5-((1R,2R,3S,6R)-3-hydroxy-1,2,3,6-tetramethylcyclohexyl)-3-methylpenta-2,4-dien-1-yl)-4-methoxy-2-methylbenzaldehyde oxime, (E)-3-chloro-6-hydroxy-4-methoxy-5-((2E,4E)-5-((1R,2R,6R,E)-3-(methoxyimino)-1,2,6-trimethylcyclohexyl)-3-methylpenta-2,4-dien-1-yl)-2-methylbenzaldehyde O-methyl oxime, (E)-3-chloro-4-(fluoromethoxy)-6-hydroxy-5-((2E,4E)-5-((1R,2R,6R,E)-3-(methoxyimino)-1,2,6-trimethylcyclohexyl)-3-methylpenta-2,4-dien-1-yl)-2-methylbenzaldehyde O-methyl oxime, (E)-3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde O-methyl oxime, (E)-3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde O-methyl oxime, 3-chloro-4-(fluoromethoxy)-6-hydroxy-2-methyl-5-((2E,4E)-3-methyl-5-((1R,2R,6R,E)-1,2,6-trimethyl-3-(2-morpholinoethoxyimino)cyclohexyl)penta-2,4-dien-1-yl)benzaldehyde, 3-chloro-5-((2E,4E)-5-((1R,2R,6R)-3-(cyclopropylamino)-1,2,6-trimethylcyclohexyl)-3-methylpenta-2,4-dien-1-yl)-4-(fluoromethoxy)-6-hydroxy-2-methylbenzaldehyde, (E)-3-chloro-6-hydroxy-5-((2E,4E)-5-((1R,2R,3S,6R)-3-hydroxy-1,2,3,6-tetramethylcyclohexyl)-3-methylpenta-2,4-dien-1-yl)-4-methoxy-2-methylbenzaldehyde O-methyl oxime, (E)-3-chloro-5-((2E,4E)-5-((1R,2R,6R,E)-3-(2-(dimethylamino)ethoxyimino)-1,2,6-trimethylcyclohexyl)-3-methylpenta-2,4-dien-1-yl)-6-hydroxy-4-methoxy-2-methylbenzaldehyde O-methyl oxime, (E)-3-chloro-6-hydroxy-4-methoxy-2-methyl-5-((2E,4E)-3-methyl-5-((1R,2R,6R,E)-1,2,6-trimethyl-3-(2-morpholinoethoxyimino)cyclohexyl)penta-2,4-dien-1-yl)benzaldehyde O-methyl oxime, (E)-3-chloro-6-hydroxy-4-methoxy-2-methyl-5-((2E,4E)-3-methyl-5-((1R,2R,6R,E)-1,2,6-trimethyl-3-(2-(4-methylpiperazin-1-yl)ethoxyimino)-cyclohexyl)penta-2,4-dien-1-yl)benzaldehyde O-methyl oxime, ethyl 2-([[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetate, 2-([[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetic acid, 3-chloro-5-((2E,4E)-5-((1R,2R,6R)-3-(ethylamino)-1,2,6-trimethylcyclohexyl)-3-methylpenta-2,4-dien-1-yl)-6-hydroxy-4-methoxy-2-methylbenzaldehyde, (E)-3-chloro-5-((2E,4E)-5-((1R,2R,6R)-3-(ethylamino)-1,2,6-trimethylcyclohexyl)-3-methylpenta-2,4-dien-1-yl)-6-hydroxy-4-methoxy-2-methylbenzaldehyde O-methyl oxime, 3-chloro-5-((2E,4E)-5-((1R,2R,6R)-3-(cyclopropylamino)-1,2,6-trimethylcyclohexyl)-3-methylpenta-2,4-dien-1-yl)-6-hydroxy-4-methoxy-2-methylbenzaldehyde, (E)-3-chloro-5-((2E,4E)-5-((1R,2R,6R)-3-(cyclopropylamino)-1,2,6-trimethylcyclohexyl)-3-methylpenta-2,4-dien-1-yl)-6-hydroxy-4-methoxy-2-methylbenzaldehyde O-methyl oxime, 2-[(2E,4E)-5-[(1R,2R,6R)-3-amino-1,2,6-trimethylcyclohexyl]-3-methylpenta-2,4-dien-1-yl]-4-chloro-3-methoxy-6-[(1E)-(methoxyimino)methyl]-5-methylphenol, (E)-3-chloro-6-hydroxy-4-methoxy-2-methyl-5-((2E,4E)-3-methyl-5-((1R,2R,6R)-1,2,6-trimethyl-3-(oxetan-3-ylamino)cyclohexyl)penta-2,4-dien-1-yl)benzaldehyde O-methyl oxime, 2-([[(1E,2R,3R,4R)-3-[(1E,3E)-5-[3-chloro-6-hydroxy-2-fluoromethoxy-5-formyl-4-methylphenyl]-3-methylpenta-1,3-dien-1-yl]-2,3,4-trimethylcyclohexylidene]-amino]oxy)acetic acid, 2-([[(1E,2R,3R,4R)-3-[(1E,3E)-5-[3-chloro-6-hydroxy-2-methoxy-5-[(1E)-(hydroxyimino)methyl]-4-methylphenyl]-3-methylpenta-1,3-dien-1-yl]-2,3,4-trimethylcyclohexylidene]amino]oxy)acetic acid, 2-([[(1E,2R,3R,4R)-3-[(1E,3E)-5-[3-chloro-2-methoxy-6-hydroxy-5-[(1E)-(hydroxyimino)methyl]-4-methylphenyl]-3-methylpenta-1,3-dien-1-yl]-2,3,4-trimethylcyclohexylidene]amino]oxy)acetic acid, and pharmaceutically acceptable salts thereof.

(2-8) The pharmaceutical composition according to any one of (2-1) to (2-7), wherein the immune checkpoint inhibitor is selected from anti-CTLA4 antibody, anti-PD-1 antibodies and anti-PD-L1 antibodies.

(2-9) The pharmaceutical composition according to any one of (2-1) to (2-7), wherein the composition is for use in treating or preventing a cancer.

(2-10) The pharmaceutical composition according to any one of (2-1) to (2-7), wherein the immune checkpoint inhibitor is an anti-PD-1 antibody.

(2-11) The pharmaceutical composition according to any one of (2-1) to (2-7), wherein the immune checkpoint inhibitor is an anti-PD-L1 antibody.

(2-12) The pharmaceutical composition according to any one of (2-1) to (2-11), wherein the immune checkpoint inhibitor is administered in amount of 0.1 to 200 mg/kg/day.

(2-13) The pharmaceutical composition according to any one of (2-1) to (2-12), wherein the compound represented by formula (I) is administered in amount of 1 to 500 mg/kg/day.

(3-1) A method for treating or preventing a disease that involves AMPK dysregulation comprising:

administering to a subject in need thereof a therapeutically effective amount of a compound represented by formula (I):

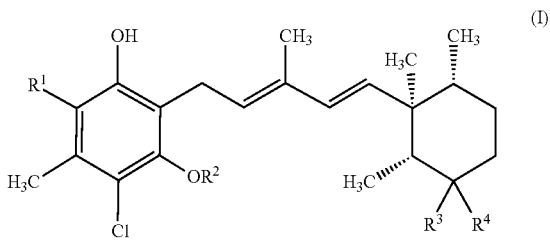

wherein $R^1$ is formyl, or —CH=N—O—Y, in which Y is a hydrogen atom or $C_{1-6}$ alkyl;

$R^2$ is $C_{1-6}$ alkyl, in which the alkyl may be substituted with one to five fluorine atoms;

$R^3$ is a hydrogen atom or $C_{1-6}$ alkyl;

$R^4$ is hydroxy, $C_{1-6}$ alkylamino, $C_{3-7}$ cycloalkylamino, or 3- to 7-membered heterocycloalkylamino which contains —O—, —S—, —$NR^6$—, —SO— or —$SO_2$— as a ring atom, or $R^3$ and $R^4$ together with the carbon atom to which they are attached form >C=N—O—Z;

Z is a hydrogen atom, $C_{1-6}$ alkyl, —CO(CH$_2$)$_n$—$R^5$ or —(CH$_2$)$_n$—$R^5$;

n is an integer selected from 1 to 4;

$R^5$ is —$CO_2R^6$, —$CONR^7R^8$, —$OCONR^7R^8$, —$SO_2NR^7R^8$, —$SO_2R^9$, hydroxy, —$NHSO_2R^9$, or —$NR^7R^8$;

$R^6$, $R^7$ and $R^8$ are each independently selected from a group consisting of a hydrogen atom, $C_{1-6}$ alkyl, and $C_{3-7}$ cycloalkyl; or $R^7$ and $R^8$ together with the nitrogen atom to which they are attached form a nitrogen containing heterocyclic ring which may further contain —O—, —S—, —$NR^6$—, —SO— or —$SO_2$— as a ring atom, in which the heterocyclic ring may be substituted with one or more substituents selected from hydroxy and $C_{1-6}$ alkyl, $R^9$ is $C_{1-6}$ alkyl, or $C_{3-7}$ cycloalkyl;

a pharmaceutically acceptable salt or a solvate thereof, in combination with administering a therapeutically effective amount of an immune checkpoint inhibitor.

(3-2) The method according to (3-1), wherein $R^4$ is selected from the group consisting of hydroxy, methylamino, ethylamino, cyclopropylamino, and oxetan-3-ylamino.

(3-3) The method according to (3-1), wherein $R^3$ and $R^4$ together with the carbon atom to which they are attached form >C=N—O—Z in which Z is selected from the group consisting of a hydrogen atom, $C_{1-6}$ alkyl, —$CH_2CO_2H$, —$CH_2CO_2R^5$, morpholinoethyl, piperazinylethyl, N-methyl-piperazinylethyl, and N,N-dimethylamino-ethyl.

(3-4) The method according to (3-2) or (3-3), wherein $R^1$ is formyl.

(3-5) The method according to (3-2) or (3-3), wherein $R^1$ is —CH=N—OH.

(3-6) The method according to (3-2) or (3-3), wherein $R^1$ is —CH=N—OMe.

(3-7) The method according to (3-1), wherein the compound represented by formula (I) is selected from the group consisting of 3-chloro-6-hydroxy-5-((2E,4E)-5-((1R,2R,6R)-3-hydroxy-1,2,3,6-tetramethylcyclohexyl)-3-methylpenta-2,4-dien-1-yl)-4-methoxy-2-methylbenzaldehyde, 3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde, (E)-3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde oxime, 3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde oxime, 3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde,

[(1E,2R,3R,4R)-3-[(1E,3E)-5-(3-chloro-5-formyl-6-hydroxy-2-methoxy-4-methylphenyl)-3-methylpenta-1,3-dien-1-yl]-2,3,4-trimethylcyclohexylidene]amino 2-(dimethylamino)acetate, (E)-3-chloro-6-hydroxy-5-((2E,4E)-5-((1R,2R,3S,6R)-3-hydroxy-1,2,3,6-tetramethylcyclohexyl)-3-methylpenta-2,4-dien-1-yl)-4-methoxy-2-methylbenzaldehyde oxime, (E)-3-chloro-6-hydroxy-4-methoxy-5-((2E,4E)-5-((1R,2R,6R,E)-3-(methoxyimino)-1,2,6-trimethylcyclohexyl)-3-methylpenta-2,4-dien-1-yl)-2-methylbenzaldehyde O-methyl oxime, (E)-3-chloro-4-(fluoromethoxy)-6-hydroxy-5-((1R,2R,6R,E)-3-(methoxyimino)-1,2,6-trimethylcyclohexyl)-3-methylpenta-2,4-dien-1-yl)-2-methylbenzaldehyde O-methyl oxime, (E)-3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde O-methyl oxime, (E)-3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde O-methyl oxime, 3-chloro-4-(fluoromethoxy)-6-hydroxy-2-methyl-5-((2E,4E)-3-methyl-5-((1R,2R,6R,E)-1,2,6-trimethyl-3-(2-morpholinoethoxyimino)cyclohexyl)penta-2,4-dien-1-yl)benzaldehyde, 3-chloro-5-((2E,4E)-5-((1R,2R,6R)-3-(cyclopropylamino)-1,2,6-trimethylcyclohexyl)-3-methylpenta-2,4-dien-1-yl)-4-(fluoromethoxy)-6-hydroxy-2-methylbenzaldehyde, (E)-3-chloro-6-hydroxy-5-((2E,4E)-5-((1R,2R,3S,6R)-3-hydroxy-1,2,3,6-tetramethylcyclohexyl)-3-methylpenta-2,4-dien-1-yl)-4-methoxy-2-methylbenzaldehyde O-methyl oxime, (E)-3-chloro-5-((2E,4E)-5-((1R,2R,6R,E)-3-(2-(dimethylamino)ethoxyimino)-1,2,6-trimethylcyclohexyl)-3-methylpenta-2,4-dien-1-yl)-6-hydroxy-4-methoxy-2-methylbenzaldehyde O-methyl oxime, (E)-3-chloro-6-hydroxy-4-methoxy-2-methyl-5-((2E,4E)-3-methyl-5-((1R,2R,6R,E)-1,2,6-trimethyl-3-(2-morpholinoethoxyimino)cyclohexyl)penta-2,4-dien-1-yl)benzaldehyde O-methyl oxime, (E)-3-chloro-6-hydroxy-4-methoxy-2-methyl-5-((2E,4E)-3-methyl-5-((1R,2R,6R,E)-1,2,6-trimethyl-3-(2-(4-methylpiperazin-1-yl)ethoxyimino)-cyclohexyl)penta-2,4-dien-1-yl)benzaldehyde O-methyl oxime, ethyl 2-([[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetate, 2-([[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetic acid, 3-chloro-5-((2E,4E)-5-((1R,2R,6R)-3-(ethylamino)-1,2,6-trimethylcyclohexyl)-3-methylpenta-2,4-dien-1-yl)-6-hydroxy-4-methoxy-2-methylbenzaldehyde, (E)-3-chloro-5-((2E,4E)-5-((1R,2R,6R)-3-(ethylamino)-1,2,6-trimethylcyclohexyl)-3-methylpenta-2,4-dien-1-yl)-6-hydroxy-4-methoxy-2-methylbenzaldehyde O-methyl oxime, 3-chloro-5-((2E,4E)-5-((1R,2R,6R)-3-(cyclopropylamino)-1,2,6-trimethylcyclohexyl)-3-methylpenta-2,4-dien-1-yl)-6-hydroxy-4-methoxy-2-methylbenzaldehyde, (E)-3-chloro-5-((2E,4E)-5-((1R,2R,6R)-3-(cyclopropylamino)-1,2,6-trimethylcyclohexyl)-3-methylpenta-2,4-dien-1-yl)-6-hydroxy-4-methoxy-2-methylbenzaldehyde O-methyl oxime, 2-[(2E,4E)-5-[(1R,2R,6R)-3-amino-1,2,6-trimethylcyclohexyl]-3-methylpenta-2,4-dien-1-yl]-4-chloro-3-methoxy-6-[(1E)-(methoxyimino)methyl]-5-methylphenol, (E)-3-chloro-6-hydroxy-4-methoxy-2-methyl-5-((2E,4E)-3-methyl-5-((1R,2R,6R)-1,2,6-trimethyl-3-(oxetan-3-ylamino)cyclohexyl)penta-2,4-dien-1-yl)benzaldehyde O-methyl oxime, 2-([[(1E,2R,3R,4R)-3-[(1E,3E)-5-[3-chloro-6-hydroxy-2-fluoromethoxy-5-formyl-4-methylphenyl]-3-methylpenta-1,3-dien-1-yl]-2,3,4-trimethylcyclohexylidene]amino]oxy)acetic acid, 2-([[(1E,2R,3R,4R)-3-[(1E,3E)-5-[3-chloro-6-hydroxy-2-methoxy-5-[(1E)-(hydroxyimino)methyl]-4-methylphenyl]-3-methylpenta-1,3-dien-1-yl]-2,3,4-trimethylcyclohexylidene]amino]oxy)acetic acid, 2-([[(1E,2R,3R,4R)-3-[(1E,3E)-5-[3-chloro-2-methoxy-6-hydroxy-5-[(1E)-(hydroxyimino)methyl]-4-methylphenyl]-3-methylpenta-1,3-dien-1-yl]-2,3,4-trimethylcyclohexylidene]amino]oxy)acetic acid, and pharmaceutically acceptable salts thereof.

(3-8) The method according to any one of (3-1) to (3-7), wherein the immune checkpoint inhibitor is selected from anti-CFLA4 antibody, anti-PD-1 antibodies and anti-PD-L1 antibodies.

(3-9) The method according to any one of (3-1) to (3-7), wherein the disease is a cancer.

(3-10) The method according to any one of (3-1) to (3-7), wherein the immune checkpoint inhibitor is an anti-PD-1 antibody.

(3-11) The method according to any one of (3-1) to (3-7), wherein the immune checkpoint inhibitor is an anti-PD-L1 antibody.

(3-12) The method according to any one of (3-1) to (3-11), wherein the immune checkpoint inhibitor is administered in amount of 0.1 to 200 mg/kg/day.

(3-13) The pharmaceutical composition according to any one of (3-1) to (3-12), wherein the compound represented by formula (I) is administered in amount of 1 to 500 mg/kg/day.

Advantageous Effects of the Invention

The pharmaceutical composition is useful in treating or preventing a cancer or tumor, for example, carcinoma, squamous carcinoma (e.g. cervical canal, eyelid, tunica conjunctiva, vagina, lung, oral cavity, skin, urinary bladder, tongue, larynx, and gullet), adenocarcinoma (e.g. prostate, small intestine, endometrium, cervical canal, large intestine, lung, pancreas, gullet, intestinum rectum, uterus, stomach, mammary gland, and ovary), and sarcomata (for example, myogenic sarcoma), leukosis, neuroma, melanoma, and lymphoma. Particularly, a cancer or tumor is selected from melanoma, non-small-cell lung cancer (NSLC), kidney cancer, non-Hodgkin lymphoma, head and neck cancer, and urothelial carcinoma.

The compound of formula (I) is useful as a preventive or therapeutic agent for the disease in which AMPK is dysregulated; such as metabolic syndrome, type 2 diabetes, dyslipidemia, adiposity, atherosclerotic cardiovascular disease, hypertension, and nonalcoholic fatty liver disease (NAFLD), inflammation and Alzheimer disease. Furthermore, the compound of formula (I) is useful as a preventive or therapeutic agent for cancers such as hepatoma, glioma, breast, prostate and non-small cell lung carcinoma and cancer-associated inflammation. Examples of the cancers include cancers that involve activation of PI3K/AKT/mTOR pathway and/or loss of tumor suppressor LKB1, such as breast cancer (e.g. triple negative breast cancer), hepatoma (especially sorafenib resistant HCC), colon cancer, prostate cancer, glioma and non-small cell lung carcinoma. [Oncotarget, vol. 6 (10), page 7365, 2015].

DESCRIPTION OF EMBODIMENTS

Figure 1:
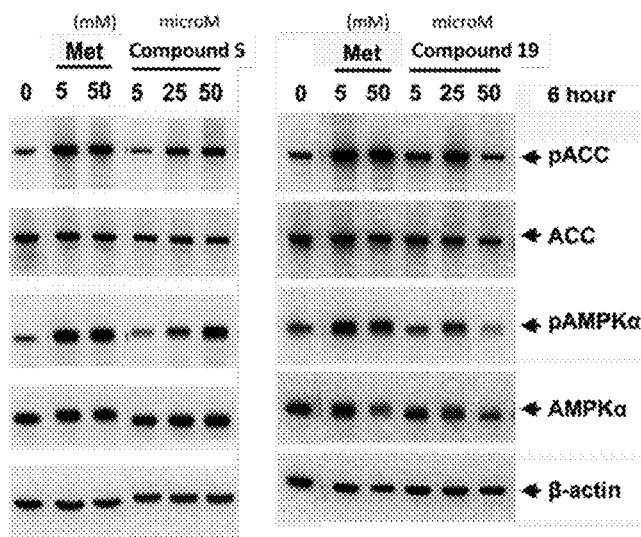
FIG. 1 shows the results of western blot analysis to indicate AMPK activation and downstream signal, ACC in HepG2 cell.

In the subject specification, the term "$C_{1-6}$ alkyl" refers to a linear or branched saturated hydrocarbon group having 1 to 6 carbon atoms. Examples thereof include methyl, ethyl, n-propyl, iso-propyl, butyl, iso-butyl, tert-butyl, n-pentyl, pentan-3-yl and the like.

The term "$C_{1-6}$ alkylamino" means a group: —NH—($C_{1-6}$ alkyl), in which $C_{1-6}$ alkyl is as defined above.

The term "$C_{3-7}$ cycloalkyl" refers to a saturated carbocyclic group having 3 to 7 carbon atoms. Examples thereof include cyclopropyl (cPr), cyclobutyl, cyclopentyl, cyclohexyl, cycloheptyl and the like.

The term "$C_{3-7}$ cycloalkylamino" means a group: —NH—($C_{3-7}$ cycloalkyl), in which "$C_{37}$ cycloalkyl" is as defined above. Examples thereof include cyclopropylamino, cyclobutylamino, cyclopentylamino, cyclohexylamino, cycloheptylamino and the like.

The term "3- to 7-membered heterocycloalkylamino" refers to an amino group substituted with a saturated heterocyclic group having 3 to 7 ring atoms, which includes one or more hetero atoms selected from —O—, —S—, —$NR^6$—, —SO— and —$SO_2$—. Examples thereof include pyrrolidinylamino, piperidinylamino, piperazinylamino, N-methylpiperazinylamino, morpholinylamino, thiomorpholinylamino, imidazolidinylamino, homopiperizynylamino, homopiperazinylamino, and the like.

The term "a nitrogen-containing 3- to 7-membered heterocyclic ring" refers to a heterocyclic ring having 3 to 7 ring atoms, which includes at least one nitrogen atom and one or more hetero atoms selected from —O—, —S—, —$NR^6$—, —SO— and —$SO_2$—. Examples thereof include pyrrolidine, piperidine, piperazine, N-methylpiperazine, morphorine, thiomorpholine, imidazolidine, imidazoline, homopiperidine, homopiperazine and the like.

In one embodiment of the present invention, $R^1$ is selected from aldehyde, —CH=N—OH, —CH=N—OMe, and —CH=N—OEt.

In another embodiment of the present invention, $R^2$ is $C_{1-6}$ alkyl which may be substituted with 1 to 3 fluorine atoms, for example, $CH_3$, $CH_2CH_3$, $CHF_2$, $CH_2F$, $CF_3$, and $CH_2CF_3$, preferably $CH_3$ or $CH_2F$.

In another embodiment of the present invention, $R^3$ is selected from hydrogen, methyl and ethyl.

In another embodiment of the present invention, $R^4$ is selected from a group consisting of hydroxy, methylamino, ethylamino, cyclopropylamino, oxetan-3-ylamino, (3-morpholinopropyl)amino, pirrolidin-3-ylamino or (3-(2-methylpipelidin-1-yl)propyl)amino. Preferably, $R^4$ is selected from hydroxyl, ethylamino, cyclopropylamino, and oxetan-3-ylamino.

In another embodiment of the present invention, $R^3$ and $R^4$ form a group =N—O—Z, in which Z is a hydrogen atom, $C_{1-6}$ alkyl or, —$(CH_2)_n$—$R^5$, and $R^5$ is as defined above. Examples of the group =N—O—Z include hydroxyimino, methoxyimino, (2-(N,N-dimethylamino)ethoxy)imino, (2-morpholinoethoxy)imino, (2-(4-methylpiperazinyl)ethoxy)imino, (ethoxycarbonylmethoxy)imino, (carboxymethoxy)imino, ((N,N-dimethylamino)acetoxy)imino.

Specifically, the compound of formula (I) is exemplified by the compounds (Compounds 1 to 28) indicated in Table 1.

TABLE 1

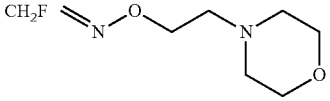

| No. | $R^1$ | $R^2$ | $R^3$ | $R^4$ |
|---|---|---|---|---|
| 1 | —CHO | Me | Me | OH |
| 2 | —CHO | Me | =N—OH (E-form) | |
| 3 | —CH=N—OH (E-form) | Me | =N—OH (E-form) | |
| 4 | —CH=N—OH (E-form) | $CH_2F$ | =N—OH (E-form) | |
| 5 | —CHO | $CH_2F$ | =N—OH (E-form) | |
| 6 | —CHO | Me | =N—OC(=O)$CH_2NMe_2$ (E-form) | |
| 7 | —CH=N—OH (E-form) | Me | Me | OH |
| 8 | —CH=N—OMe (E-form) | Me | =N—OMe (E-form) | |
| 9 | —CH=N—OMe (E-form) | $CH_2F$ | =N—OMe (E-form) | |
| 10 | —CH=N—OMe (E-form) | Me | =N—OH (E-form) | |
| 11 | —CH=N—OMe (E-form) | $CH_2F$ | =N—OH (E-form) | |
| 12 | —CHO | $CH_2F$ | 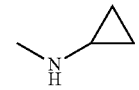 | |
| 13 | —CHO | $CH_2F$ | H | 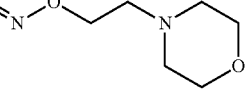 |
| 14 | —CH=N—OMe (E-form) | Me | Me | OH |
| 15 | —CH=N—OMe (E-form) | Me | =N—O$(CH_2)_2NMe_2$(E-form) | |
| 16 | —CH=N—OMe (E-form) | Me | 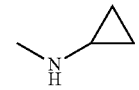 | |

TABLE 1-continued

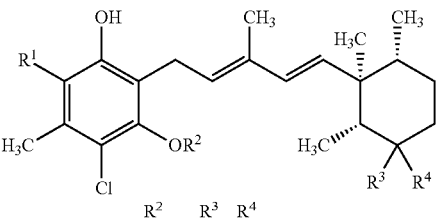

| No. | R¹ | R² | R³ | R⁴ |
|---|---|---|---|---|
| 17 | —CH=N—OMe (E-form) | Me | 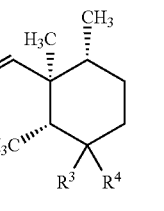 | |
| 18 | —CH=N—OMe (E-form) | Me | =N—OCH₂—CO₂Et (E-form) | |
| 19 | —CH=N—OMe (E-form) | Me | =N—OCH₂—CO₂H (E-form) | |
| 20 | —CHO | Me | H | NHEt |
| 21 | —CH=N—OMe (E-form) | Me | H | NHEt |
| 22 | —CHO | Me | H | 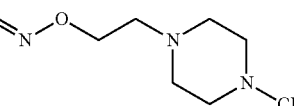 |
| 23 | —CH=N—OMe (E-form) | Me | H | 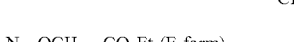 |
| 24 | —CH=N—OMe (E-form) | Me | H | NH₂ |
| 25 | —CH=N—OMe (E-form) | Me | H | 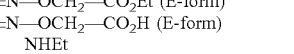 |
| 26 | —CHO | CH₂F | =N—OCH₂—CO₂H (E-form) | |
| 27 | —CH=N—OH (E-form) | CH₂F | =N—OCH₂—CO₂H (E-form) | |
| 28 | —CH=N—OH (E-form) | Me | =N—OCH₂—CO₂H (E-form) | |

More specifically, the compound of formula (I) is exemplified by the following compounds:
1) 3-chloro-6-hydroxy-5-((2E,4E)-5-((1R,2R,6R)-3-hydroxy-1,2,3,6-tetramethylcyclohexyl)-3-methylpenta-2,4-dien-1-yl)-4-methoxy-2-methylbenzaldehyde;
2) 3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde;
3) (E)-3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde oxime;
4) (E)-3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde oxime;
5) 3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde;
6) [(1E,2R,3R,4R)-3-[(1E,3E)-5-(3-chloro-5-formyl-6-hydroxy-2-methoxy-4-methylphenyl)-3-methylpenta-1,3-dien-1-yl]-2,3,4-trimethylcyclohexylidene]amino 2-(dimethylamino)acetate;
7) (E)-3-chloro-6-hydroxy-5-((2E,4E)-5-((1R,2R,6R)-3-hydroxy-1,2,3,6-tetramethylcyclohexyl)-3-methylpenta-2,4-dien-1-yl)-4-methoxy-2-methylbenzaldehyde oxime;
8) (E)-3-chloro-6-hydroxy-4-methoxy-5-((2E,4E)-5-((1R,2R,6R,E)-3-(methoxyimino)-1,2,6-trimethylcyclohexyl)-3-methylpenta-2,4-dien-1-yl)-2-methylbenzaldehyde O-methyl oxime;
9) (E)-3-chloro-4-(fluoromethoxy)-6-hydroxy-5-((2E,4E)-5-((1R,2R,6R,E)-3-(methoxyimino)-1,2,6-trimethylcyclohexyl)-3-methylpenta-2,4-dien-1-yl)-2-methylbenzaldehyde O-methyl oxime;
10) (E)-3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde O-methyl oxime;
11) (E)-3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde O-methyl oxime;
12) 3-chloro-4-(fluoromethoxy)-6-hydroxy-2-methyl-5-((2E,4E)-3-methyl-5-((1R,2R,6R,E)-1,2,6-trimethyl-3-(2-morpholinoethoxyimino)cyclohexyl)penta-2,4-dien-1-yl)benzaldehyde;
13) 3-chloro-5-((2E,4E)-5-((1R,2R,6R)-3-(cyclopropylamino)-1,2,6-trimethylcyclohexyl)-3-methylpenta-2,4-dien-1-yl)-4-(fluoromethoxy)-6-hydroxy-2-methylbenzaldehyde;
14) (E)-3-chloro-6-hydroxy-5-((2E,4E)-5-((1R,2R,6R)-3-hydroxy-1,2,3,6-tetramethylcyclohexyl)-3-methylpenta-2,4-dien-1-yl)-4-methoxy-2-methylbenzaldehyde O-methyl oxime;

15) (E)-3-chloro-5-((2E,4E)-5-((1R,2R,6R,E)-3-(2-(dimethylamino)ethoxyimino)-1,2,6-trimethylcyclohexyl)-3-methylpenta-2,4-dien-1-yl)-6-hydroxy-4-methoxy-2-methylbenzaldehyde O-methyl oxime;
16) (E)-3-chloro-6-hydroxy-4-methoxy-2-methyl-5-((2E,4E)-3-methyl-5-((1R,2R,6R,E)-1,2,6-trimethyl-3-(2-morpholinoethoxyimino)cyclohexyl)penta-2,4-dien-1-yl)benzaldehyde O-methyl oxime;
17) (E)-3-chloro-6-hydroxy-4-methoxy-2-methyl-5-((2E,4E)-3-methyl-5-((1R,2R,6R,E)-1,2,6-trimethyl-3-(2-(4-methylpiperazin-1-yl)ethoxyimino)cyclohexyl)penta-2,4-dien-1-yl)benzaldehyde O-methyl oxime;
18) ethyl 2-([[[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetate;
19) 2-([[[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetic acid;
20) 3-chloro-5-((2E,4E)-5-((1R,2R,6R)-3-(ethylamino)-1,2,6-trimethylcyclohexyl)-3-methylpenta-2,4-dien-1-yl)-6-hydroxy-4-methoxy-2-methylbenzaldehyde;
21) (E)-3-chloro-5-((2E,4E)-5-((1R,2R,6R)-3-(ethylamino)-1,2,6-trimethylcyclohexyl)-3-methylpenta-2,4-dien-1-yl)-6-hydroxy-4-methoxy-2-methylbenzaldehyde O-methyl oxime;
22) 3-chloro-5-((2E,4E)-5-((1R,2R,6R)-3-(cyclopropylamino)-1,2,6-trimethylcyclohexyl)-3-methylpenta-2,4-dien-1-yl)-6-hydroxy-4-methoxy-2-methylbenzaldehyde;
23) (E)-3-chloro-5-((2E,4E)-5-((1R,2R,6R)-3-(cyclopropylamino)-1,2,6-trimethylcyclohexyl)-3-methylpenta-2,4-dien-1-yl)-6-hydroxy-4-methoxy-2-methylbenzaldehyde O-methyl oxime;
24) 2-[(2E,4E)-5-[(1R,2R,6R)-3-amino-1,2,6-trimethylcyclohexyl]-3-methylpenta-2,4-dien-1-yl]-4-chloro-3-methoxy-6-[(1E)-(methoxyimino)methyl]-5-methylphenol;
25) (E)-3-chloro-6-hydroxy-4-methoxy-2-methyl-5-((2E,4E)-3-methyl-5-((1R,2R,6R)-1,2,6-trimethyl-3-(oxetan-3-ylamino)cyclohexyl)penta-2,4-dien-1-yl)benzaldehyde O-methyl oxime;
26) 2-([[[(1E,2R,3R,4R)-3-[(1E,3E)-5-[3-chloro-6-hydroxy-2-fluoromethoxy-5-formyl-4-methylphenyl]-3-methylpenta-1,3-dien-1-yl]-2,3,4-trimethylcyclohexylidene]amino]oxy)acetic acid;
27) 2-([[[(1E,2R,3R,4R)-3-[(1E,3E)-5-[3-chloro-6-hydroxy-2-fluoromethoxy-5-[(1E)-(hydroxyimino)methyl]-4-methylphenyl]-3-methylpenta-1,3-dien-1-yl]-2,3,4-trimethylcyclohexylidene]amino]oxy)acetic acid;
28) 2-([[[(1E,2R,3R,4R)-3-[(1E,3E)-5-[3-chloro-2-methoxy-6-hydroxy-5-[(1E)-(hydroxyimino)methyl]-4-methylphenyl]-3-methylpenta-1,3-dien-1-yl]-2,3,4-trimethylcyclohexylidene]amino]oxy)acetic acid;
and pharmaceutically acceptable salts thereof.

The compound of formula (I) is exemplified by the following compounds:

7-1) (E)-3-chloro-6-hydroxy-5-((2E,4E)-5-((1R,2R,3S,6R)-3-hydroxy-1,2,3,6-tetramethylcyclohexyl)-3-methylpenta-2,4-dien-1-yl)-4-methoxy-2-methylbenzaldehyde oxime;
7-2) (E)-3-chloro-6-hydroxy-5-((2E,4E)-5-((1R,2R,3R,6R)-3-hydroxy-1,2,3,6-tetramethylcyclohexyl)-3-methylpenta-2,4-dien-1-yl)-4-methoxy-2-methylbenzaldehyde oxime;
13-1) 3-chloro-5-((2E,4E)-5-((1R,2R,3S,6R)-3-(cyclopropylamino)-1,2,6-trimethylcyclohexyl)-3-methylpenta-2,4-dien-1-yl)-4-(fluoromethoxy)-6-hydroxy-2-methylbenzaldehyde;
13-2) 3-chloro-5-((2E,4E)-5-((1R,2R,3R,6R)-3-(cyclopropylamino)-1,2,6-trimethylcyclohexyl)-3-methylpenta-2,4-dien-1-yl)-4-(fluoromethoxy)-6-hydroxy-2-methylbenzaldehyde;
14-1) (E)-3-chloro-6-hydroxy-5-((2E,4E)-5-((1R,2R,3S,6R)-3-hydroxy-1,2,3,6-tetramethylcyclohexyl)-3-methylpenta-2,4-dien-1-yl)-4-methoxy-2-methylbenzaldehyde O-methyl oxime;
14-2) (E)-3-chloro-6-hydroxy-5-((2E,4E)-5-((1R,2R,3R,6R)-3-hydroxy-1,2,3,6-tetramethylcyclohexyl)-3-methylpenta-2,4-dien-1-yl)-4-methoxy-2-methylbenzaldehyde O-methyl oxime;
20-1) 3-chloro-5-((2E,4E)-5-((1R,2R,3S,6R)-3-(ethylamino)-1,2,6-trimethylcyclohexyl)-3-methylpenta-2,4-dien-1-yl)-6-hydroxy-4-methoxy-2-methylbenzaldehyde;
20-2) 3-chloro-5-((2E,4E)-5-((1R,2R,3R,6R)-3-(ethylamino)-1,2,6-trimethylcyclohexyl)-3-methylpenta-2,4-dien-1-yl)-6-hydroxy-4-methoxy-2-methylbenzaldehyde;
21-1) (E)-3-chloro-5-((2E,4E)-5-((1R,2R,3S,6R)-3-(ethylamino)-1,2,6-trimethylcyclohexyl)-3-methylpenta-2,4-dien-1-yl)-6-hydroxy-4-methoxy-2-methylbenzaldehyde O-methyl oxime;
21-2) (E)-3-chloro-5-((2E,4E)-5-((1R,2R,3R,6R)-3-(ethylamino)-1,2,6-trimethylcyclohexyl)-3-methylpenta-2,4-dien-1-yl)-6-hydroxy-4-methoxy-2-methylbenzaldehyde O-methyl oxime;
22-1) 3-chloro-5-((2E,4E)-5-((1R,2R,3S,6R)-3-(cyclopropylamino)-1,2,6-trimethylcyclohexyl)-3-methylpenta-2,4-dien-1-yl)-6-hydroxy-4-methoxy-2-methylbenzaldehyde;
22-2) 3-chloro-5-((2E,4E)-5-((1R,2R,3R,6R)-3-(cyclopropylamino)-1,2,6-trimethylcyclohexyl)-3-methylpenta-2,4-dien-1-yl)-6-hydroxy-4-methoxy-2-methylbenzaldehyde;
23-1) (E)-3-chloro-5-((2E,4E)-5-((1R,2R,3S,6R)-3-(cyclopropylamino)-1,2,6-trimethylcyclohexyl)-3-methylpenta-2,4-dien-1-yl)-6-hydroxy-4-methoxy-2-methylbenzaldehyde O-methyl oxime;
23-2) (E)-3-chloro-5-((2E,4E)-5-((1R,2R,3R,6R)-3-(cyclopropylamino)-1,2,6-trimethylcyclohexyl)-3-methylpenta-2,4-dien-1-yl)-6-hydroxy-4-methoxy-2-methylbenzaldehyde O-methyl oxime;
24-1) 2-[(2E,4E)-5-[(1R,2R,3S,6R)-3-amino-1,2,6-trimethylcyclohexyl]-3-methylpenta-2,4-dien-1-yl]-4-chloro-3-methoxy-6-[(1E)-(methoxyimino)methyl]-5-methylphenol;
24-2) 2-[(2E,4E)-5-[(1R,2R,3R,6R)-3-amino-1,2,6-trimethylcyclohexyl]-3-methylpenta-2,4-dien-1-yl]-4-chloro-3-methoxy-6-[(1E)-(methoxyimino)methyl]-5-methylphenol;
25-1) (E)-3-chloro-6-hydroxy-4-methoxy-2-methyl-5-((2E,4E)-3-methyl-5-((1R,2R,3S,6R)-1,2,6-trimethyl-3-(oxetan-3-ylamino)cyclohexyl)penta-2,4-dien-1-yl)benzaldehyde O-methyl oxime;
25-2) (E)-3-chloro-6-hydroxy-4-methoxy-2-methyl-5-((2E,4E)-3-methyl-5-((1R,2R,3R,6R)-1,2,6-trimethyl-3-(oxetan-3-ylamino)cyclohexyl)penta-2,4-dien-1-yl)benzaldehyde O-methyl oxime;

According to one aspect of the present invention, the compound of formula (I) is selected from the compounds of Nos. (5), (8), (9), (10), (11), (12), (14), (15), (16), (19), (21), (24), (25), (26), (27), (28) indicated above, and particularly preferably a compound selected from the compounds of Nos. (5), (10), (12), (15), (16), (19), (21), and (25) indicated above.

The compound of formula (I) has activity to increase phosphorylation of AMPK and its downstream effector, acetyl-CoA carboxylase (ACC) [Test Example 1]. Further, the compound has significantly improved metabolic stability against degradation by liver microsome (human and mouse) [Test Example 3], improved PK profile that allows once a day oral treatment [Test Example 4], and improved solubility [Test Example 2] as compared with 4-O-methyl-ascoclorin (MAC) and its prodrug, a Schiff base of MAC with glycine amide (compound #13 in WO2004/074236).

The compounds of formula (I) may be administered in the form of a pharmaceutically acceptable salt. The term "pharmaceutically acceptable salt" refers to a salt, which is non-toxic and is prepared with a pharmaceutically acceptable base or acid. When the compound of formula (I) is basic, the pharmaceutically acceptable salt thereof is generally prepared by adding the compound with a suitable organic or inorganic acid. Examples of the acid-addition salt include acetate, benzenesulfonate, benzoate, citrate, fumarate, glutamate, hydrobromide, hydrochloride, lactate, maleate, mandelate, mesylate, oxalate, palmitate, phosphate/diphosphate, salicylate, stearate, sulfate, succinate, tartrate, and tosylate.

Furthermore, when the compound of formula (I) is acidic, the pharmaceutically acceptable salt thereof is generally prepared by adding the compound with a suitable organic or inorganic base. Examples of the base-addition salt include salts derived from inorganic bases including aluminum, ammonium, calcium, potassium, sodium and the like. Particularly preferred are the ammonium, calcium, potassium, and sodium salts. Examples of the base-addition salt also include salts derived from primary, secondary, and tertiary amines such as arginine, betaine, 2-diethylaminoethanol, 2-dimethylaminoethanol, ethanolamine, N-ethylmorpholine, N-ethylpiperidine, glucamine, glucosamine, histidine, lysine, methylglucamine, morpholine, piperazine, piperidine, triethylamine, tripropylamine, and the like.

The compound of formula (I) may be administered as a prodrug. The prodrug can be prepared in line with technical knowledge commonly available to a person skilled in the art. For example, in the case of a carboxy group (—COOH) or hydroxy group being present in the compounds of formula (I), a prodrug can be prepared by converting the carboxy group to a pharmaceutically acceptable ester group, such as methyl, ethyl, or pivaloyloxymethyl ester, or by converting the hydroxy group to a pharmaceutically acceptable ester group, such as acetate or maleate. Use of a prodrug may be beneficial for modifying the solubility or hydrolysis characteristics for use as sustained-release or prodrug formulations.

In one embodiment, the compound of formula (I) may be used in an amorphous form or a crystalline form. The crystalline form may include solvent to form a solvate such as a hydrate. It should be understood that the present invention covers any use of such a solvate or any mixture such as a solution, suspension or solid mixture containing the compound of formula (I).

According to one aspect of the present invention, there is provided a method for treating or preventing a disease that involves AMPK dysregulation including a cancer, which comprises administering to a patient in need thereof a therapeutically effective amount of a compound represented by formula (I) or a pharmaceutically acceptable salt thereof in combination with administration of an immune checkpoint inhibitor. The disease that involves AMPK dysregulation is preferably a cancer. An appropriate route of the administration of the compound represented by formula (I) may be determined by a person skilled in the art. Examples thereof include oral, endorectal, parenteral (intravenous, intramuscular, or subcutaneous), intracisternal, vaginal, intraperitoneal, intravesical, topical (drip infusion, powder, ointment, gel, or cream) application, and inhalation (intraoral or nasal spray). The dosage form of the compound represented by formula (I) for the administration includes tablets, capsules, granules, powders, pills, aqueous and non-aqueous solutions or suspensions for oral use, and parenteral solutions loaded into containers.

According to one aspect of the present invention, there is provided a pharmaceutical composition comprising a compound represented by formula (I) or a pharmaceutically acceptable salt thereof, and a pharmaceutically acceptable excipient or additive, for use in combination with administration of an immune checkpoint inhibitor. The composition may be administered in an appropriate route, for example, oral, endorectal, parenteral (intravenous, intramuscular, or subcutaneous), intracisternal, vaginal, intraperitoneal, intravesical, topical (drip infusion, powder, ointment, gel, or cream) application, and inhalation (intraoral or nasal spray). The dosage form for the administration includes tablets, capsules, granules, powders, pills, aqueous and non-aqueous solutions or suspensions for oral use, and parenteral solutions loaded into containers.

The pharmaceutical composition may be administered as a pharmaceutical formulation. The pharmaceutical formulation can be produced by well-known methods, using additives such as excipients, coating agents, lubricants, binders, disintegrators, stabilizers, corrigents, diluents, solvent and surfactants or emulsifiers.

Examples of excipients include starches such as potato starch and cornstarch, lactose, crystalline cellulose, and calcium hydrogen phosphate.

Examples of coating agents include ethylcellulose, hydroxypropylcellulose, hydroxypropylmethylcellulose, shellac, talc, carnauba wax, and paraffin.

Examples of lubricants include magnesium stearate, and stearic acid.

Examples of binders include polyvinylpyrrolidone, macrogol, and the same substances exemplified as the excipients.

Examples of disintegrators include the same substances exemplified as the excipients and croscarmellose sodium, sodium carboxymethylstarch, and chemically modified starch or celluloses.

Examples of stabilizers include paraoxybenzoic acid esters such as methylparaben and propylparaben; alcohols such as chlorobutanol, benzylalcohol, and phenylethylalcohol; benzalkonium chloride; phenols such as phenol and cresol; thimerosal; dehydroacetic acid; and ascorbic acid.

Examples of corrigents include sweeteners which are conventionally used.

Examples of diluents include the substances exemplified as excipients.

Examples of solvents include ethanol, phenol, chlorocresol, purified water, and distilled water.

Examples of surfactants or emulsifiers include polysorbate 80, polyoxyl 40 stearate, lauromacrogol, soybean oil, Maisin 35-1 (Gattefosse, France) and Cremophor (BASF, Germany).

The dose of the compounds of formula (I) or pharmaceutically acceptable salts thereof differs depending on the symptoms, age, body weight, relative health condition, presence of other medication, method of administration, and the like. For example, a generally effective dose for an oral agent as the active ingredient for a patient (a warmblooded animal, especially a human) is a daily dose of preferably 0.1 to 1000 mg per kg body weight, more preferably 1 to 30 mg per kg body weight. The daily dose for an adult patient with a normal body weight is preferably in the range of 10 to 1000 mg. For a parenteral agent, the daily dose is preferably 0.1 to 1000 mg per kg body weight, more preferably 10 to 800 mg per kg body weight. Preferably such a dose is administered at one time or in several portions per day, or intermittent schedule depending on the symptoms.

An immune checkpoint inhibitor includes a cytotoxic T-lymphocyte-associated protein 4 (CTLA4) inhibitor, a programmed cell death protein 1 (PD-1) inhibitor, or a programmed death-ligand 1 (PD-L1) inhibitor. In the present invention, anti-CTLA4 antibody, anti-PD-1 antibody, anti-PD-1 fusion protein or anti-PD-L1 antibody is preferably used as an immune checkpoint inhibitor. The anti-CTLA4 antibody is exemplified by ipilimumab and tremelimumab. The anti-PD-1 fusion protein is exemplified by ANP-224. The anti-PD-1 antibody is exemplified by nivormab, pembrolizumab, pidilizumab (CT-011), MEDIO680 (AMP-514), REGN2810, PDR001, JS001-PD-1, SHR-1210, and BMS-936559. Particularly, the anti-PD-1 antibody is selected from nivormab, and pembrolizumab. The anti-PD-L1 antibody is exemplified by atezolizumab (MPDL3280A), avelumab (MSB0010718C), durvalumab (MEDI4736), and BMS-936559.

The immune checkpoint inhibitor may be administered, by a route and in an amount that are commonly known therefor, simultaneously or sequentially with a compound of formula (I). When the compound is administered simultaneously with an immune checkpoint inhibitor, these ingredients may be contained in a single unit dosage form or two or more separate dosage forms. In the combination therapy, the compound of formula (I) and an immune checkpoint inhibitor are administered on different overlapping schedules. It is also contemplated that in the combination therapy, the compounds of formula (I) and the immune checkpoint inhibitor may be administered in lower doses than that administered each alone.

The dosage of the compounds of formula (I) and the immune checkpoint inhibitor used for the subject invention is determined depending on age of a subject, body weight of a subject, symptom, degree of seriousness, therapeutic effect, administration route, administration regimen, and period of the treatment, According to one aspect of the subject invention, the compound represented by formula (I) is administered in an amount from 1 to 500 mg/kg/day, particularly 10 to 300 mg/kg/day, more particularly 25 to 50 mg/kg/day.

According to one aspect of the subject invention, the immune checkpoint inhibitor is administered in an amount from 0.1 to 200 mg/kg/day, particularly 1 to 50 mg/kg/day, more particularly 5 to 15 mg/kg/day.

According to one aspect of the subject invention, the anti-PD-1 antibody is administered in an amount from 0.1 to 200 mg/kg/day, particularly 1 to 50 mg/kg/day, more particularly 5 to 15 mg/kg/day.

According to one aspect of the subject invention, the anti-PD-L1 antibody is administered in an amount from 0.1 to 200 mg/kg/day, particularly 1 to 50 mg/kg/day, more particularly 5 to 15 mg/kg/day.

According to one aspect of the subject invention, the compound represented by formula (I) is administered in an amount from 1 to 500 mg/kg/day, and the immune checkpoint inhibitor is administered in an amount from 0.1 to 200 mg/kg/day. According to another aspect of the subject invention, the compound represented by formula (I) is administered in an amount from 10 to 300 mg/kg/day, and the immune checkpoint inhibitor is administered in an amount from 1 to 50 mg/kg/day. According to another aspect of the subject invention, the compound represented by formula (I) is administered in an amount from 1 to 500 mg/kg/day, and the immune checkpoint inhibitor is administered in an amount from 5 to 15 mg/kg/day.

The composition of the present invention is for use in treating or preventing a disease involves AMPK dysregulation, particularly a cancer, which is exemplified by a cancer or tumor selected from melanoma, non-small-cell lung cancer (NSLC), kidney cancer, non-Hodgkin lymphoma, head and neck cancer, stomach cancer, esophageal cancer, ovary cancer, liver cancer, breast cancer, colorectal cancer and urothelial carcinoma.

Synthetic processes for preparing the compounds represented by formula (I) are illustrated in the following schemes and examples.

A starting material, ascochlorin can be obtained by fermentation of *Ascochyts viciae* Libert as described in JP S45-009832 B published in 1970. In the following schemes, $R^2$, $R^3$, $R^4$, $R^5$, $R^7$, Y, and Z are as defined hereinbefore.

Scheme 1

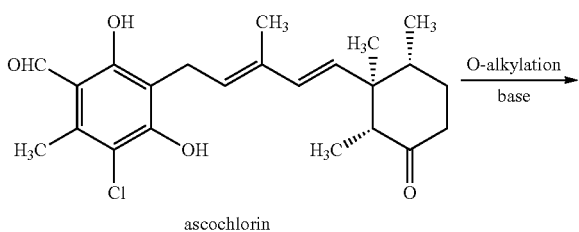

ascochlorin

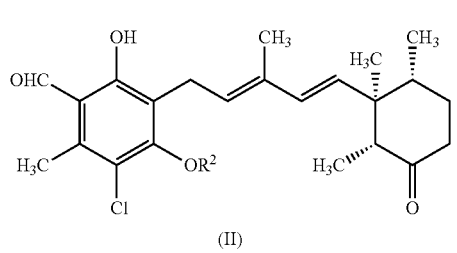

(II)

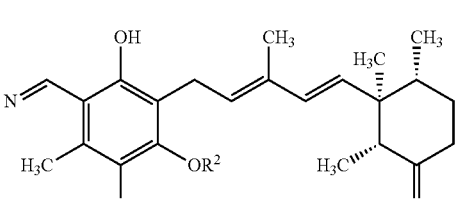

(VI)

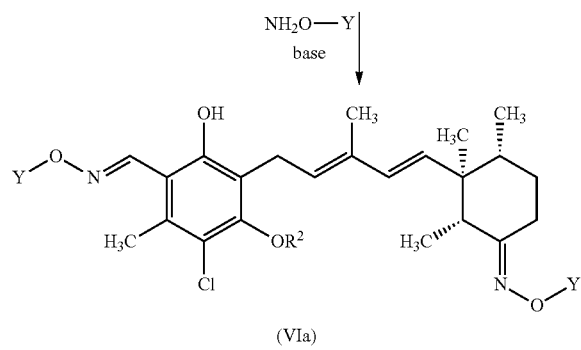

(VIa)

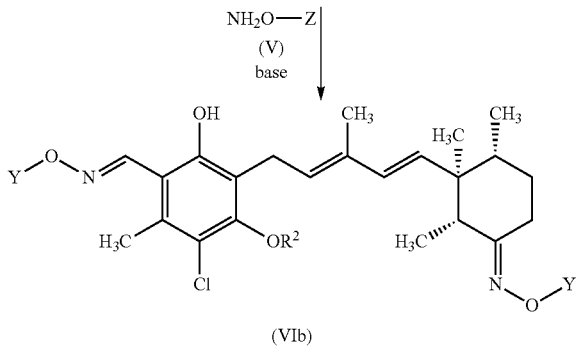

(VIb)

Scheme 1 shows a method for producing compound (IV), (VIa) or (VIb). The compound (II) in which $R^2$ is methyl (4-O-methyl-ascochlorin) can be prepared by the method described in JP H6-305959 A. The compound (II) in which $R^2$ is fluorinated alkyl group can be obtained by O-alkylation with a fluoroalkylating agent in the presence of base in an appropriate solvent. Examples of the base include potassium carbonate, cesium carbonate and the like. Examples of fluoroalkylating agents include bromofluoromethane, bis(trifluoromethyl)-bis(trifluoromethyloxy)-sulfane, 5-tert-butyl-2'-(trifluoromethoxy)biphenylyl-2-diazonium hexafluoroantimonate, 2,2,2-tris(fluoranyl)ethyl methanesulfonate, 2-diazo-1,1,1-tris(fluoranyl)ethane, tris(fluoranyl)methane, 1-chloranyl-4-[chloranyl-bis(fluoranyl)methyl]sulfonyl-benzene and the like.

The compound (IV) can be prepared by reacting a compound (II) with $NH_2OY$ (III) in the presence of base such as pyridine, sodium carbonate, sodium hydrogen carbonate and the like. The compound (VIb) can be prepared by reacting compound (IV) with $NH_2OZ$ (V) in the presence of base such as pyridine, sodium carbonate, sodium hydrogen carbonate and the like. The compound (VIa) can be directly prepared from the compound (II) by reacting two or more equivalents of hydroxyamine (III) in the same reaction condition as described above.

The compound (VIb) wherein Z is $-(CH_2)_n CO_2H$ can be prepared by basic hydrolysis of the corresponding ester derivative (VIb) wherein Z is $-(CH_2)_n CO_2R^6$.

Scheme 2

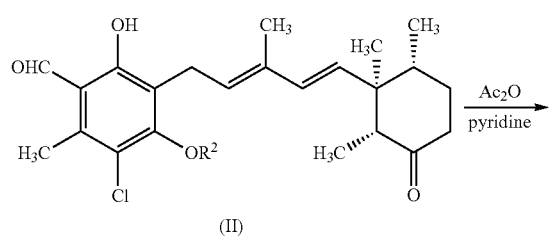

(II)

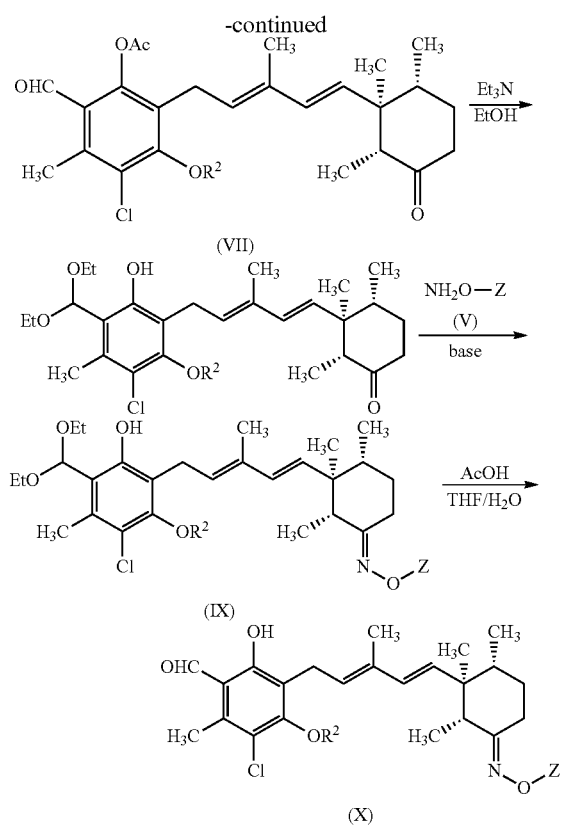

Scheme 2 shows a method for producing compound (X). The compound (VIII) in which $R^2$ is methyl or fluorinated alkyl can be prepared from ascochlorin via O-acetyl derivative (VII) wherein $R^2$ is methyl or fluorinated alkyl by the method described in JP 2005-225851 A. The intermediate (IX) can be prepared by reacting the intermediate (VIII) with $NH_2$—Z (V) in the presence of base such as pyridine, sodium carbonate, sodium hydrogen carbonate and the like.

The compound (X) can be prepared by acidic hydrolysis of the acetal group of compound (IX) in an appropriate solvent by the method known to a person skilled in the art.

Scheme 3

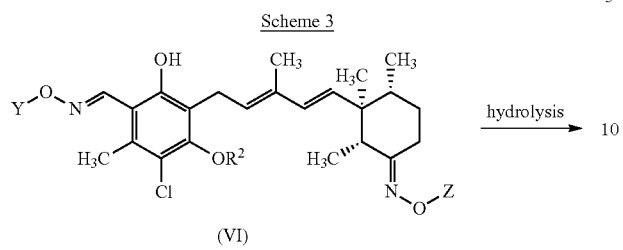

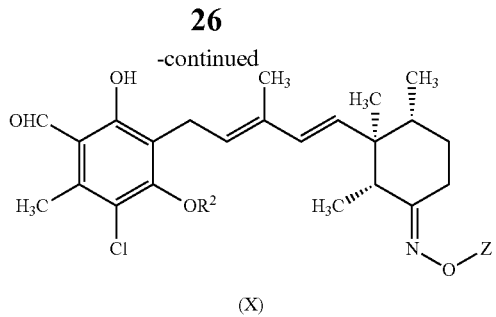

Scheme 3 shows another method for producing compound (X). The compound (X) can be prepared from the corresponding oxime derivative (VI) by treatment with hydrochloric acid in THF/H$_2$O at 100° C.

Scheme 4

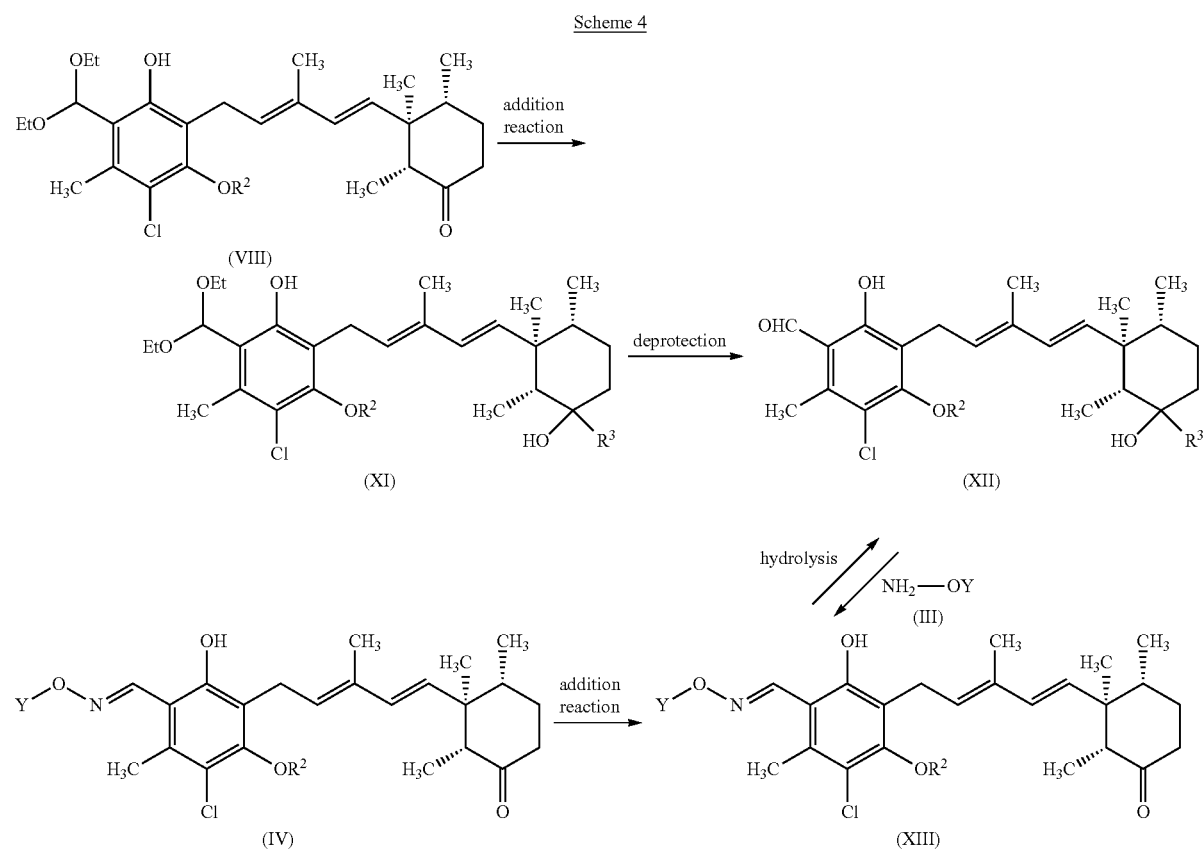

Scheme 4 shows a method for producing compounds (XII) and (XIII). The intermediate (XI) can be prepared by reacting the intermediate (VIII) with an alkylating agent, such as alkyl lithium, alkyl Grignard agent or alkyl cupper lithium reagent, in an appropriate solvent. The compound (XII) can be prepare by acidic hydrolysis of the acetal group of the intermediate (XI) in an appropriate solvent.

The compound (XIII) can be prepared by reacting the intermediate (IV) with an alkylating agent stated above in an appropriate solvent. The compound (XIII) can be also prepared by reacting the compound (XII) with NH$_2$—OY (III) in the presence of base such as pyridine, sodium carbonate, sodium hydrogen carbonate and the like. The compound (XII) can be also prepared from the compound (XIII) under similar reaction condition as described in Scheme 3.

Scheme 5a

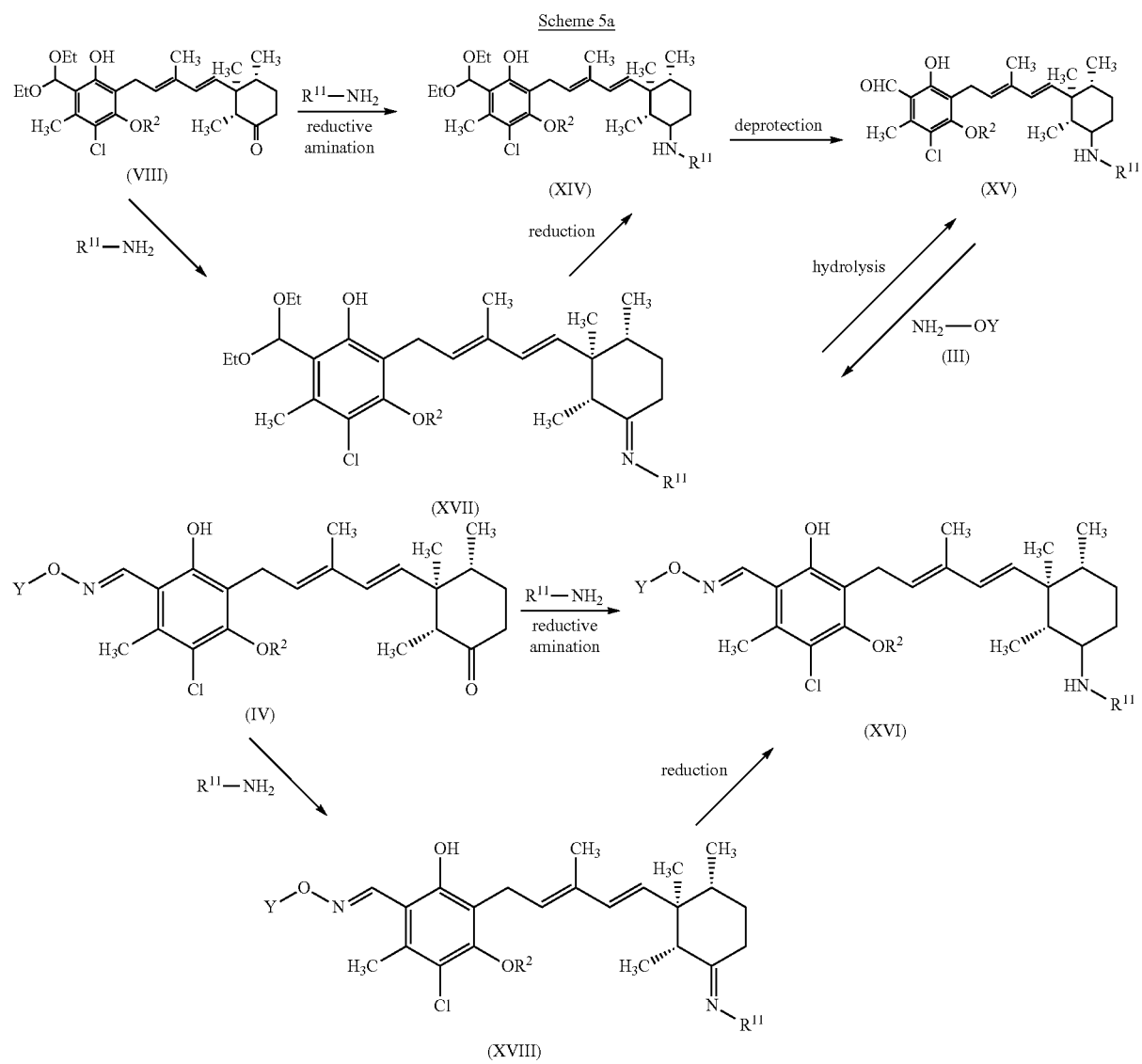

Scheme 5a shows a method for producing compound (XV) and (XVI) wherein $R^{11}$ is $C_{1-6}$ alkyl, $C_{3-7}$ cycloalkyl, or 3- to 7-membered heterocycloalkyl which contains —O—, —S—, —$NR^6$—, or —$SO_2$— as a ring atom. The intermediate (XIV) can be prepared by reductive amination of the intermediate (VIII) with a primary amine, $R^{11}$—NH, in one step or stepwise via intermediate imine (XVII), using the reducing agent such as sodium cyanoborohydride, sodium triacetoxyborohydride and the like.

The compound (XV) can be prepared by acidic hydrolysis of the acetal group of compound (XIV) in an appropriate solvent by the method known to the skilled art. The compound (XVI) can be prepared by reductive amination of the intermediate (IV) with a primary amine, $R^{11}$—$NH_2$ by the same method as described above either directly or step wise fashion via intermediate (XVIII).

The compound (XV) can be also prepared from the oxime ether derivative represented by the formula (XVI) under similar reaction condition as described in Scheme 3.

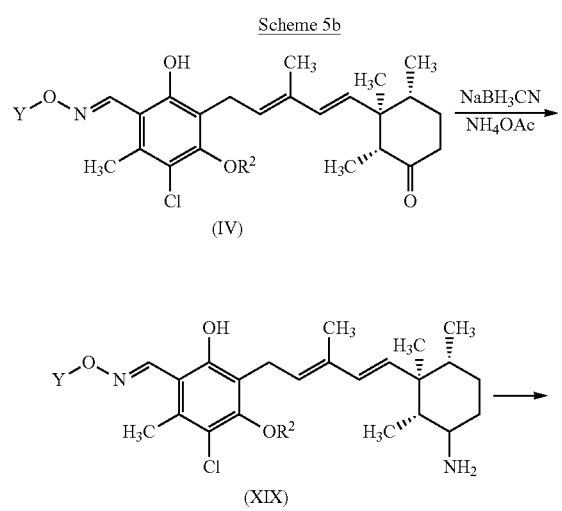

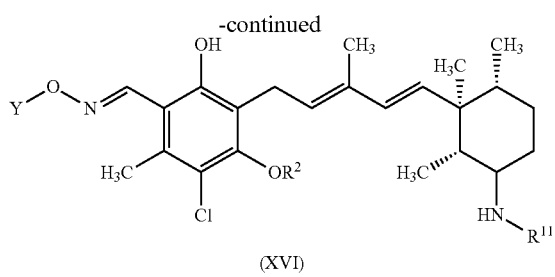

(XVI)

The compound (XVI) wherein $R^{11}$ is $C_{1-6}$ alkyl, $C_{3-7}$ cycloalkyl or 3- to 7-membered heterocycloalkylamino which contains —O—, —S—, —$NR^6$—, —SO— or —$SO_2$— as a ring atom such as oxetane can be prepared from the intermediate (IV) in 2 steps: (i) by reductive amination with ammonium acetate/sodium cyanoborohydride in ethanol, (ii) followed by second reductive amination of the resulting intermediate (XIX) with a ketone corresponding to $R^{11}$ such as oxetan-3-one and sodium triacetoxyborohydride in dichloromethane.

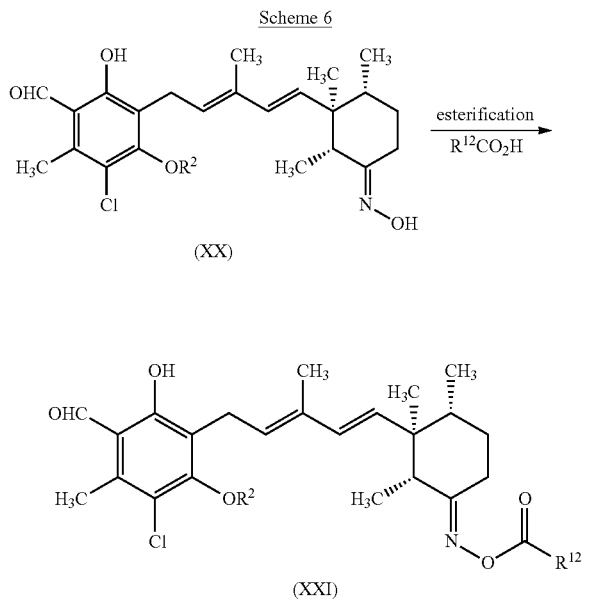

Scheme 6 shows a method for producing compound (XXI), wherein $R^{11}$ is $C_{1-6}$ alkyl, $C_{3-7}$ cycloalkyl, or 3- to 7-membered heterocycloalkyl which contains —O—, —S—, —$NR^6$—, or —$SO_2$— as a ring atom. The intermediate (XX) can be prepared by Scheme 2 or 3. The compound (XXI) can be prepared by esterification of XX with a carboxylic acid of formula $R^{12}CO_2H$ by an active ester method or with condensation agent that are known to those skilled in the art.

When the compound represented by formula (I) is obtained in a free form, it can be converted to a salt is a conventional method.

EXAMPLES

Herein below, the present invention will be more specifically described using Examples, however, it is not to be construed as being limited thereto.

NMR analysis was performed using Brucker, AVANCE 400 MHz or 300 MHz, and NMR data were expressed as chemical shifts in ppm (parts per million) (☐), and the deuterium lock signal from the sample solvent was referenced. Mass spectrum data was obtained using a LC-MS, Shimazu LCMS-2020 or -2010 equipped with a photodiode array, SPD-M20A, ESI-SQD 2020 or 2010 (Shimadzu)

Commercially available reagents were used without further purification "Room temperature" means temperatures ranging from about 20° C. to 25° C. All non-aqueous reactions were carried out under a nitrogen atmosphere. Concentration or distillation of solvents under reduced pressure means that a rotary evaporator was used.

In the preparation of compounds, a functional group was protected with a protecting group as required to obtain a target compound, followed by removal of the protecting groups. Selection of the protecting group, as well as procedure for the introduction or the removal of the protecting group were carried out, for example, according to a method described in Greene and Wuts, "Protective groups in Organic Synthesis" (second edition, John Wiley & Sons, 1991).

Example 1

Synthesis of 3-chloro-4-(fluoromethoxy)-6-hydroxy-2-methyl-5-[(2E,4E)-3-methyl-5-[(1R,2R,6R)-1,2,6-trimethyl-3-oxocyclohexyl]penta-2,4-dien-1-yl]benzaldehyde

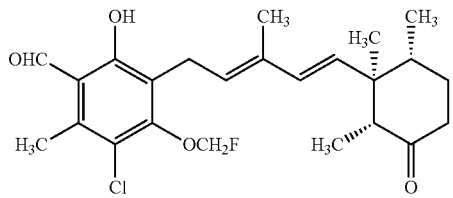

A solution of 3-chloro-4,6-dihydroxy-2-methyl-5-[(2E,4E)-3-methyl-5-[(1R,2R,6R)-1,2,6-trimethyl-3-oxocyclohexyl]penta-2,4-dien-1-yl]benzaldehyde, (ascochlorine, 6 g, 14.82 mmol) in acetonitrile (120 mL), bromofluoromethane (excess), cesium carbonate (2.4 g, 7.38 mmol) was placed in a 250-mL sealed tube. The resulting mixture was stirred for 16 h at 25° C. The mixture was filtered, and the filtrate was concentrated under vacuum. The resulting residue was purified by silica gel column chromatography with Petroleum ether/ethyl acetate (5:1). The product was recrystallized from dichloromethane/hexane in the ratio of 1:5 to give the titled compound (4.5 g, 70%) as an off-white solid.

LC-MS (ES, m/z): 435 [M−H]$^-$

H-NMR (400 MHz, DMSO, ppm): δ 12.60 (s, 1H), 10.30 (s, 1H), 5.86 (m, 2H), 5.72 (s, 1H), 5.42 (m, 2H), 3.50 (d, J=7.2 Hz, 2H), 2.64 (s, 3H), 2.54-2.49 (m, 2H), 2.17 (m, 1H), 2.05 (m, 1H), 1.84 (s, 4H), 1.52 (m, 1H), 0.73-0.67 (m, 6H), 0.59 (s, 3H)

F-NMR (400 MHz, DMSO, ppm): δ−148.31.

Example 2

Synthesis of (2R,3R,4R)-3-[(1E,3E)-5-[3-chloro-5-(diethoxymethyl)-2-(fluoromethoxy)-6-hydroxy-4-methylphenyl]-3-methylpenta-1,3-dien-1-yl]-2,3,4-trimethylcyclohexan-1-one

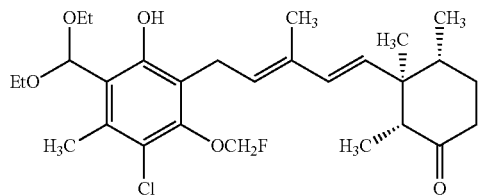

Step 1

A solution of 3-chloro-4-(fluoromethoxy)-6-hydroxy-2-methyl-5-[(2E,4E)-3-methyl-5-[(1R,2R,6R)-1,2,6-trimethyl-3-oxocyclohexyl]penta-2,4-dien-1-yl]benzaldehyde [Example 1](600 mg, 1.37 mmol) in pyridine (12 mL) was placed in a 50-mL round-bottom flask purged and maintained with an atmosphere of nitrogen, and acetic anhydride (196 mg, 1.92 mmol) was added at 25° C. The resulting solution was stirred for 1.5 h at 25° C. Then the mixture was diluted with of dichloromethane (50 mL) and washed with aqueous hydrochloric acid (0.3 mol/L, 20 mL×5). The organic layer was dried with anhydrous sodium sulfate and concentrated under vacuum to give 4-chloro-3-(fluoromethoxy)-6-formyl-5-methyl-2-[(2E,4E)-3-methyl-5-[(1R,2R,6R)-1,2,6-trimethyl-3-oxocyclohexyl]penta-2,4-dien-1-yl]phenyl acetate (500 mg, 76%) as a white solid.

Step 2

Into a solution of 4-chloro-3-(fluoromethoxy)-6-formyl-5-methyl-2-[(2E,4E)-3-methyl-5-[(1R,2R,6R)-1,2,6-trimethyl-3-oxocyclohexyl]penta-2,4-dien-1-yl]phenyl acetate (500 mg, 1.04 mmol) in ethanol (22.5 mL) was placed in a 250-mL round-bottom flask purged and maintained with an atmosphere of nitrogen, and triethylamine (0.02 mL) was added at 25° C. The solution was stirred for 5 h at 25° C., and then concentrated under vacuum to give (2R,3R,4R)-3-[(1E,3E)-5-[3-chloro-5-(diethoxymethyl)-2-(fluoromethoxy)-6-hydroxy-4-methylphenyl]-3-methylpenta-1,3-dien-1-yl]-2,3,4-trimethylcyclohexan-1-one (410 mg, 77%) as a yellow oil.

Example 3

Synthesis of 3-chloro-6-hydroxy-5-[(2E,4E)-5-[(1R,2R,3S,6R)-3-hydroxy-1,2,3,6-tetramethylcyclohexyl]-3-methylpenta-2,4-dien-1-yl]-4-methoxy-2-methylbenzaldehyde (Compound 1-1)

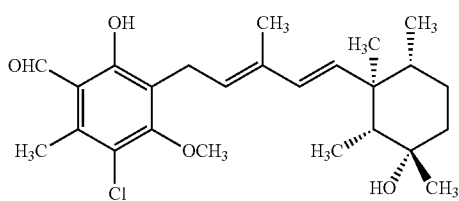 [SMILES: COc1c(Cl)c(C)c(C=O)c(O)c1C/C=C(C)/C=C/[C@@]1(C)[C@H](C)CC[C@](C)(O)[C@@H]1C]

The intermediate (VIII) wherein R² is methyl: (4R,5R,6S)-5-[(1E,3E)-5-[3-chloro-5-(diethoxymethyl)-6-hydroxy-2-methoxy-4-methylphenyl]-3-methylpenta-1,3-dien-1-yl]-4,5,6-trimethyloxan-3-one was prepared from ascochlorin by the procedures described in JP 2005-225851 A.

Step 1

A solution of (2R,3R,4R)-3-[(1E,3E)-5-[3-chloro-5-(diethoxymethyl)-6-hydroxy-2-methoxy-4-methylphenyl]-3-methylpenta-1,3-dien-1-yl]-2,3,4-trimethylcyclohexan-1-one (1 g, 2.03 mmol) in tetrahydrofuran (30 mL) was placed in a 50-mL 3-necked round-bottom flask purged and maintained with an atmosphere of nitrogen, followed by addition of methylmagnesium bromide (2 mL, 3.00 equiv, 3 M) dropwise with stirring at −78° C. The resulting solution was stirred for 3 h at 0° C. The reaction was then quenched by addition of sat. aqueous ammonium chloride (30 mL). The resulting mixture was extracted with diethyl ether (30 mL×3) and the organic layers were combined and washed with saturated aqueous sodium chloride (50 mL). The organic layer was dried over anhydrous sodium sulfate, filtered and concentrated under vacuum. The resulting residue was purified by Flash-Prep-HPLC with the following condition to give 4-chloro-2-(diethoxymethyl)-6-[(2E,4E)-5-[(1R,2R,3S,6R)-3-hydroxy-1,2,3,6-tetramethylcyclohexyl]-3-methylpenta-2,4-dien-1-yl]-5-methoxy-3-methylphenol (0.6 g, 60%) as a light yellow solid (mp. 39-40° C.).

Flash-Prep-HPLC condition (IntelFlash-1): Column, C18 silica gel; mobile phase, acetonitrile/water=70/30 increasing to $CH_3CN$/water=90/10 within 10 min and then $CH_3CN$ within 10 min; Detector, UV 210 nm. LC-MS (ESI, m/z): 507 [M−H]−

H-NMR ($CD_3CN$, 400 MHz, ppm): δ 5.91 (d, J=16.4 Hz, 1H), 5.83 (s, 1H), 5.38-5.43 (m, 1H), 5.30 (d, J=16 Hz, 1H), 3.72-3.79 (m, 5H), 3.62-3.68 (m, 2H), 3.46 (d, J=5.6 Hz, 2H), 2.33 (s, 3H), 1.87 (s, 3H), 1.45-1.70 (m, 3H), 1.29-1.35 (m, 2H), 1.20-1.25 (m, 7H), 1.12 (s, 3H), 0.90 (s, 3H), 0.80 (d, J=5.6 Hz, 3H), 0.70 (d, J=5.4 Hz, 3H).

Step 2

A solution of 4-chloro-2-(diethoxymethyl)-6-[(2E,4E)-5-[(1R,2R,3S,6R)-3-hydroxy-1,2,3,6-tetramethylcyclohexyl]-3-methylpenta-2,4-dien-1-yl]-5-methoxy-3-methylphenol (355 mg, 0.699 mmol) in tetrahydrofuran/water (10 mL/20 mL) was placed in a 50-mL round-bottom flask purged and maintained with an atmosphere of nitrogen, followed by addition of acetic acid (5 mL). The resulting solution was stirred for 5 h at 25° C. The resulting solution was concentrated under vacuum. The resulting residue was purified by Flash-Prep-HPLC with the following condition to give 3-chloro-6-hydroxy-5-[(2E,4E)-5-[(1R,2R,3S,6R)-3-hydroxy-1,2,3,6-tetramethylcyclohexyl]-3-methylpenta-2,4-dien-1-yl]-4-methoxy-2-methylbenzaldehyde (0.26 g, 76%, Compound 1) as an off-white solid (mp. 42-43° C.).

Flash-Prep-HPLC condition (IntelFlash-1): Column, C18 silica gel; mobile phase, $CH_3CN$/water=70/30 increasing to $CH_3CN$/water=90/10 within 10 min; Detector, UV 210 nm. LC-MS (ESI, m/z): 433 [M−H]−

H-NMR ($CD_3CN$, 400 MHz, ppm): δ 10.25 (s, 1H), 5.89 (d, J=16.0 Hz, 1H), 5.40 (t, J=1.2 Hz, 1H), 5.29 (d, J=16.0 Hz, 1H), 3.84 (s, 3H), 3.48 (d, J=7.2 Hz, 2H), 2.63 (s, 3H), 1.87 (s, 3H), 1.57-1.78 (m, 3H), 1.33-1.47 (m, 3H), 1.09 (s, 3H), 0.79 (d, J=3.2 Hz, 3H), 0.68 (d, J=6.8 Hz, 3H).

Example 4

Synthesis of 3-chloro-6-hydroxy-5-[(2E,4E)-5-[(1R, 2R,3E,6R)-3-(hydroxyimino)-1,2,6-trimethylcyclohexyl]-3-methylpenta-2,4-dien-1-yl]-4-methoxy-2-methylbenzaldehyde (Compound 2)

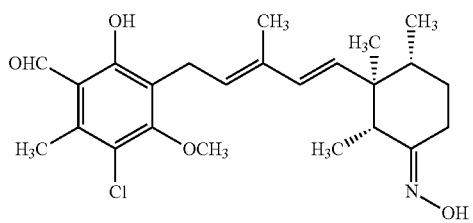 [SMILES: COc1c(Cl)c(C)c(C=O)c(O)c1C/C=C(C)/C=C/[C@@]1(C)[C@H](C)CC/C(=N\O)[C@@H]1C]

Step 1

A solution of (2R,3R,4R)-3-[(1E,3E)-5-[3-chloro-5-(diethoxymethyl)-6-hydroxy-2-methoxy-4-methylphenyl]-3-methylpenta-1,3-dien-1-yl]-2,3,4-trimethylcyclohexan-1-one (1 g, 2.03 mmol) in pyridine (30 mL) was placed in a 50-mL 3-necked round-bottom flask purged and maintained with an inert atmosphere of nitrogen, followed by addition of hydroxyamine hydrochloride (200 mg, 2.88 mmol). The mixture was stirred for 16 h at 25° C. The reaction mixture was concentrated under vacuum. The residue was purified by Flash-Prep-HPLC with the following condition to give 4-chloro-2-(diethoxymethyl)-6-[(2E,4E)-5-[(1R,2R,3E,6R)-3-(hydroxyimino)-1,2,6-trimethylcyclohexyl]-3-methylpenta-2,4-dien-1-yl]-5-methoxy-3-methylphenol (0.40 g, 39%) as an off-white solid (mp. 68-70° C.).

Flash-Prep-HPLC condition (IntelFlash-1): Column, C18 silica gel; mobile phase, $CH_3CN$/water=70/30 increasing to $CH_3CN$/water=90/10 within 15 min and then acetonitrile within 10 min; Detector, UV 210 nm.

LC-MS: (ESI, m/z): 506 [M–H]–

H-NMR: ($CD_3CN$, 400 MHz, ppm): δ 5.95 (d, J=16.0 Hz, 1H), 5.81 (s, 1H), 5.42 (q, J=12.8 Hz, 4.8 Hz, 2H), 3.69-3.77 (m, 5H), 3.59-3.66 (m, 2H), 3.45 (d, J=7.2 Hz, 2H), 3.27-3.32 (m, 1H), 2.47 (s, 3H), 2.27 (d, J=6.8 Hz, 1H), 1.88 (s, 3H), 1.60-1.72 (m, 3H), 1.19-1.29 (m, 7H), 0.82 (d, J=6.8 Hz, 3H), 0.72 (d, J=6.8 Hz, 3H), 0.67 (s, 3H).

Step 2

A solution of 4-chloro-2-(diethoxymethyl)-6-[(2E,4E)-5-[(1R,2R,3E,6R)-3-(hydroxyimino)-1,2,6-trimethylcyclohexyl]-3-methylpenta-2,4-dien-1-yl]-5-methoxy-3-methylphenol (370 mg, 0.726 mmol) in tetrahydrofuran/water (10 mL/20 mL), was placed in a 100-mL 2-necked round-bottom flask purged and maintained with an atmosphere of nitrogen, followed by addition of acetic acid (10 mL). The mixture was stirred for 5 h at 25° C. The reaction mixture was concentrated under vacuum. The residue was purified by Flash-Prep-HPLC with the following condition to give 3-chloro-6-hydroxy-5-[(2E,4E)-5-[(1R,2R,3E,6R)-3-(hydroxyimino)-1,2,6-trimethylcyclohexyl]-3-methylpenta-2,4-dien-1-yl]-4-methoxy-2-methylbenzaldehyde (220 mg, 70%, Compound 2) as a light yellow solid (mp. 158-160° C.).

Flash-Prep-HPLC condition (IntelFlash-1): Column, C18 silica gel; mobile phase, $CH_3CN$/water=70/30 increasing to $CH_3CN$/water=90/10 within 10 min; Detector, UV 210 nm.

LC-MS: (ESI, m/z): 432 [M–H]–

H-NMR: ($CD_3CN$, 400 MHz, ppm): δ 10.25 (s, 1H), 5.94 (d, J=16.4 Hz, 1H), 5.44 (q, J=15.6 Hz, 6.8 Hz, 2H), 3.85 (s, 3H), 3.50 (d, J=7.2 Hz, 2H), 3.29 (t, J=8.4 Hz, 1H), 2.63 (s, 3H), 2.21 (q, J=13.6 Hz, 6.8 Hz, 1H), 1.90 (s, 3H), 1.60-1.69 (m, 3H), 1.20-1.33 (m, 1H), 0.81 (d, J=6.8 Hz, 3H), 0.71 (d, J=6.8 Hz, 3H), 0.66 (s, 3H).

Example 5

Synthesis of 4-chloro-2-[(2E,4E)-5-[(1R,2R,3E,6R)-3-(hydroxyimino)-1,2,6-trimethylcyclohexyl]-3-methylpenta-2,4-dien-1-yl]-6-[(1E)-(hydroxyimino)methyl]-3-methoxy-5-methylphenol (Compound 3)

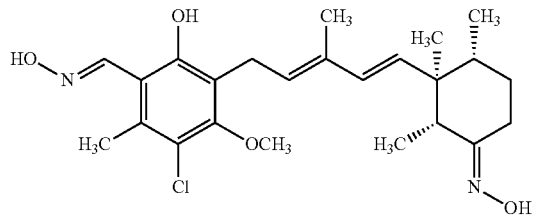

A solution of 3-chloro-6-hydroxy-4-methoxy-2-methyl-5-[(2E,4E)-3-methyl-5-[(1R,2R,6R)-1,2,6-trimethyl-3-oxocyclohexyl]penta-2,4-dien-1-yl]benzaldehyde (700 mg, 1.67 mmol, ascochlorine) in pyridine (14 ml) was placed in a 25-mL round-bottom flask, followed by addition of hydroxyamine hydrochloride (290 mg, 4.17 mmol) at 25° C. The mixture was stirred for 16 h at 25° C., and then concentrated under vacuum. After dilution with dichloromethane (100 ml), the resulting solution was washed with aqueous hydrochloric acid (1N, 50 mL×2) and brine (50 mL). The organic layer was dried over anhydrous sodium sulfate, filtered and concentrated under vacuum. The resulting residue was purified by Flash-Prep-HPLC with the following condition to give the titled compound (221.8 mg, 29.6%) as a white solid.

Flash-Prep-HPLC condition (IntelFlash-1): Column, silica gel; mobile phase, $CH_3CN$/water (0.08% ammonium bicarbonate)=50/50 increasing to a $CH_3CN$/water (0.08% ammonium bicarbonate)=80/20 within 25 min; Detector, UV 254 nm.

LC-MS (ES, m/z): 449 [M+H]+

H-NMR ($CD_3OD$, 400 MHz, ppm): 8.56 (s, 1H), 5.92 (d, J=16 Hz, 1H), 5.46 (m, 2H), 3.78 (s, 3H), 3.52 (d, J=7.2 Hz, 2H), 3.41 (m, 1H), 3.31 (m, 1H), 2.43 (s, 3H), 2.20 (m, 1H), 1.91 (s, 3H), 1.67 (m, 3H), 1.33 (m, 1H), 0.91-0.69 (m, 9H)

Example 6

Synthesis of 3-chloro-4-(fluoromethoxy)-6-hydroxy-5-[(2E,4E)-5-[(1R,2R,3E,6R)-3-(hydroxyimino)-1,2,6-trimethylcyclohexyl]-3-methylpenta-2,4-dien-1-yl]-2-methylbenzaldehyde (Compound 5)

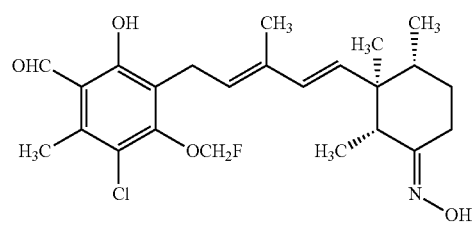

Step 1

A solution of (2R,3R,4R)-3-[(1E,3E)-5-[3-chloro-5-(diethoxymethyl)-2-(fluoromethoxy)-6-hydroxy-4-methylphenyl]-3-methylpenta-1,3-dien-1-yl]-2,3,4-trimethylcyclohexan-1-one [Example 2] (410 mg, 0.80 mmol) in pyridine (12.3 mL) was placed in a 25-mL round-bottom flask, followed by addition of hydroxyamine hydrochloride (83.7 mg, 1.20 mmol, 1.50 equiv) at 25° C. The mixture was stirred overnight at 25° C., and then diluted with dichloromethane (300 mL). The organic layer was washed with aqueous hydrogen chloride (0.3 mol/L, 200 mL×5). The organic layer was combined and concentrated under vacuum to give 4-chloro-2-(diethoxymethyl)-5-(fluoromethoxy)-6-[(2E,4E)-5-[(1R,2R,3E,6R)-3-(hydroxyimino)-1,2,6-trimethylcyclohexyl]-3-methylpenta-2,4-dien-1-yl]-3-methylphenol (330 mg, 78%) as a yellow solid.

Step 2

A solution of 4-chloro-2-(diethoxymethyl)-5-(fluoromethoxy)-6-[(2E,4E)-5-[(1R,2R,3E,6R)-3-(hydroxyimino)-1,2,6-trimethylcyclohexyl]-3-methylpenta-2,4-dien-1-yl]-3-methylphenol (330 mg, 0.63 mmol) in tetrahydrofuran (6.6 mL) was placed in a 250-mL round-bottom flask, and then a solution of glacial acetic acid (6.6 mL, 5.56 equiv) in water (13.2 mL) was added at 25° C. The mixture was stirred for 4 h at 25° C., and then extracted with of dichloromethane (100 mL×5). The organic layer was combined and the pH value of the solution was adjusted to 7-8 with aqueous sodium bicarbonate. The resulting organic layer was separated, dried and concentrated under vacuum. The resulting residue was purified by Flash-Prep-HPLC with the following condition to give 3-chloro-4-(fluoromethoxy)-6-hydroxy-5-[(2E,4E)-5-[(1R,2R,3E,6R)-3-(hydroxyimino)-1,2,6-trimethylcyclohexyl]-3-methylpenta-2,4-dien-1-yl]-2-methylbenzaldehyde (200 mg, 71%, Compound 5) as a yellow solid.

Flash-Prep-HPLC condition (IntelFlash-1): Column, C18 silica gel; mobile phase, $CH_3CN/H_2O$=50/50 increasing to $CH_3CN/H_2O$=80/20 within 28 min; Detector, UV 254 nm.

LC-MS (ES, m/z): 452 $[M+H]^+$

H-NMR (DMSO, 300 MHz, ppm): 12.59 (s, 1H), 10.34 (s, 1H), 10.30 (s, 1H), 5.85-5.90 (t, 2H), 5.70 (s, 1H), 5.43 (s, 1H), 5.38 (d, J=4.5 Hz, 2H), 3.48-3.51 (d, J=7.5 Hz, 2H), 3.31-3.20 (m, 1H), 2.72-2.64 (d, J=24.9 Hz, 1H), 2.26-2.18 (m, 1H), 1.84 (s, 3H), 1.63-1.54 (m, 3H), 1.24-1.19 (d, J=13.2 Hz, 1H)

Example 7

Synthesis of [(1E,2R,3R,4R)-3-[(1E,3E)-5-(3-chloro-5-formyl-6-hydroxy-2-methoxy-4-methylphenyl)-3-methylpenta-1,3-dien-1-yl]-2,3,4-trimethylcyclohexylidene]amino 2-(dimethylamino)-acetate
(Compound 6)

Step 1

A solution of 2-(dimethylamino)acetic acid (15 mg, 0.15 mmol) in dichloromethane (0.4 mL) was placed in a 25-mL round-bottom flask, followed by addition of 1-(3-dimethylaminopropyl)-3-ethylcarbodiimide methiodide (45 mg, 0.15 mmol), 1-hydroxybenzotrizole (21 mg, 0.16 mmol) and N-methylmorpholine (15 mg, 0.15 mmol) at 25° C. The mixture was stirred for 30 min at 25° C. Then 3-chloro-6-hydroxy-5-[(2E,4E)-5-[(1R,2R,3E,6R)-3-(hydroxyimino)-1,2,6-trimethylcyclohexyl]-3-methylpenta-2,4-dien-1-yl]-4-methoxy-2-methylbenzaldehyde, [Compound 2, Example 3] (60 mg, 0.14 mmol) was added. The resulting mixture was stirred for 2 h at 25° C., then washed with water (10 mL) and brine (10 ml). The organic layer was dried over anhydrous sodium sulfate, filtered and concentrated under vacuum. The resulting residue was purified by Prep-HPLC with the following condition to give the titled compound (30 mg, 42%) as a yellow solid.

Prep-HPLC condition: Column, X Bridge C18, 19*150 mm 5 um; mobile phase, $CH_3CN$/water (0.05% ammonium bicarbonate)=50/50 increasing to $CH_3CN$/water (0.05% ammonium bicarbonate)=100/0 within 30 min. Detector, UV 254 nm.

LC-MS: (ES, m/z): 519 $[M+H]^+$

H-NMR: ($CD_3OD$, 400 MHz, ppm): 10.30 (s, 1H), 5.96 (d, J=16 Hz, 1H), 5.46 (m, 2H), 3.83 (s, 3H), 3.52 (d, J=7.2 Hz, 2H), 3.34 (s, 2H), 3.31 (m, 1H), 2.64 (s, 3H), 2.47-2.32 (m, 7H), 1.95 (m, 4H), 1.76 (m, 2H), 1.39 (m, 1H), 0.97 (d, J=6.8 Hz, 3H), 0.75-0.88 (m, 6H).

Step 2

A solution of hydrogen chloride in tetrahydrofuran (0.0225M, 13 mL) was added to [(1E,2R,3R,4R)-3-[(1E,3E)-5-(3-chloro-5-formyl-6-hydroxy-2-methoxy-4-methylphenyl)-3-methylpenta-1,3-dien-1-yl]-2,3,4-trimethylcyclohexylidene]amino 2-(dimethylamino)acetate (150 mg, 0.29 mmol) in a 50-mL round-bottom flask. The mixture was stirred for 5 min at 25° C., then concentrated under vacuum to give [(1E,2R,3R,4R)-3-[(1E,3E)-5-(3-chloro-5-formyl-6-hydroxy-2-methoxy-4-methylphenyl)-3-methylpenta-1,3-dien-1-yl]-2,3,4-trimethylcyclohexylidene]amino 2-(dimethylamino)acetate hydrochloride (101.6 mg, 63%) as a light yellow solid.

LC-MS: (ES, m/z):519 $[M+H]^+$

H-NMR: ($CD_3OD$, 300 MHz, ppm): 10.30 (s, 1H), 5.96 (d, J=17.7 Hz, 1H), 4.34 (m, 2H), 3.83 (s, 3H), 3.52 (m, 2H), 2.81-3.15 (m, 6H), 3.31 (m, 1H), 2.64 (s, 3H), 2.45 (m, 1H), 1.60-2.11 (m, 7H), 1.39 (m, 1H), 0.97 (m, 3H), 0.78 (m, 6H).

Example 8

Synthesis of 4-chloro-3-(fluoromethoxy)-2-[(2E,4E)-5-[(1R,2R,3E,6R)-3-(hydroxyimino)-1,2,6-trimethylcyclohexyl]-3-methylpenta-2,4-dien-1-yl]-6-[(1E)-(hydroxyimino)methyl]-5-methylphenol
(Compound 4)

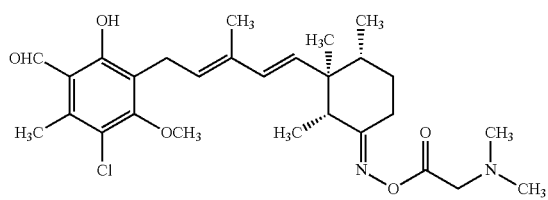

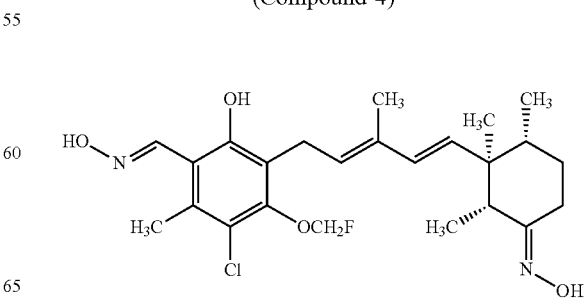

A solution of 3-chloro-4-(fluoromethoxy)-6-hydroxy-2-methyl-5-[(2E,4E)-3-methyl-5-[(1R,2R,6R)-1,2,6-trimethyl-3-oxocyclohexyl]penta-2,4-dien-1-yl]benzaldehyde [Example 1](250 mg, 0.57 mmol) in pyridine (7.5 mL) was placed in a 25 mL round-bottom flask, followed by addition of hydroxyamine hydrochloride (80 mg, 1.15 mmol) at 25° C. The mixture was stirred for 16 h at 25° C., and concentrated under vacuum. The resulting residue was purified by Flash-Prep-HPLC with the following condition to give the titled compound (201.7 mg, 75%, Compound 4) as a white solid.

Flash-Prep-HPLC condition (IntelFlash-1) to give: Column, silica gel; mobile phase, CH$_3$CN/water (0.08% ammonium bicarbonate)=70/30 increasing to CH$_3$CN/water (0.08% ammonium bicarbonate)=90/10 within 15 min; Detector, UV 220 nm.

LC-MS: (ES, m/z): 467 [M+H]$^+$

H-NMR: (CD$_3$OD, 400 MHz, ppm): 8.55 (s, 1H), 5.90 (d, J=16 Hz, 1H), 5.72 (s, 1H), 5.58 (s, 1H), 5.39-5.47 (m, 1H), 3.58 (d, J=7.2 Hz, 2H), 3.36-3.42 (m, 1H), 2.43 (s, 3H), 2.18 (t, 1H), 1.89 (s, 3H), 1.61-1.70 (m, 3H), 1.29-1.35 (m, 1H).

Example 9

Synthesis of 4-chloro-2-[(2E,4E)-5-[(1R,2R,3S,6R)-3-hydroxy-1,2,3,6-tetramethylcyclohexyl]-3-methyl-penta-2,4-dien-1-yl]-6-[(1E)-(hydroxyimino)methyl]-3-methoxy-5-methylphenol (Compound 7-1)

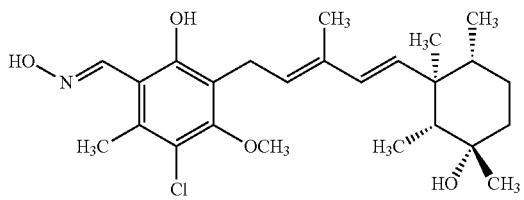 [SMILES: COc1c(Cl)c(C)c(/C=N/O)c(O)c1C/C=C(C)/C=C/[C@@]1(C)[C@H](C)CC[C@](C)(O)[C@@H]1C]

A solution of 3-chloro-6-hydroxy-5-[(2E,4E)-5-[(1R,2R,3S,6R)-3-hydroxy-1,2,3,6-tetramethylcyclohexyl]-3-methylpenta-2,4-dien-1-yl]-4-methoxy-2-methylbenzaldehyde [Compound 1, Example 2] (160 mg, 0.37 mmol) in pyridine (9.6 mL) was placed in a 25-mL round-bottom flask, followed by addition of hydroxyamine hydrochloride (25.6 mg, 0.37 mmol, 1.00 equiv) at 25° C. The mixture was stirred for 16 h at 25° C. and then concentrated under vacuum. The resulting residue was purified by Flash-Prep-HPLC with the following condition to give the titled compound (114.0 mg, 69%, Compound 7-1) as a white solid.

Flash-Prep-HPLC condition (IntelFlash-1): Column, silica gel; mobile phase, CH$_3$CN/water (0.08% NH$_4$HCO$_3$)=70/30 increasing to CH$_3$CN/water (0.08% NH$_4$HCO$_3$)=90/10 within 15 min; Detector, UV 254 nm.

LC-MS: (ES, m/z): 450 [M+H]$^+$

H-NMR: (CD$_3$OD, 400 MHz, ppm): 8.55 (s, 1H), 5.87 (d, J=16 Hz, 1H), 5.42 (t, 1H), 5.24 (d, J=16 Hz, 1H), 3.78 (s, 3H), 3.47-3.53 (m, 2H), 2.44 (s, 3H), 1.88 (s, 3H), 1.46-1.72 (m, 3H), 1.30-1.37 (m, 2H), 1.21 (m, 3H), 1.15 (s, 1H), 0.92 (s, 3H), 0.84 (d, J=7.2 Hz, 3H), 0.72 (d, J=6.8 Hz, 3H).

Example 10

Synthesis of 4-chloro-3-methoxy-2-[(2E,4E)-5-[(1R,2R,3E,6R)-3-(methoxyimino)-1,2,6-trimethylcyclohexyl]-3-methylpenta-2,4-dien-1-yl]-6-[(1E)-(methoxyimino)methyl]-5-methylphenol (Compound 8)

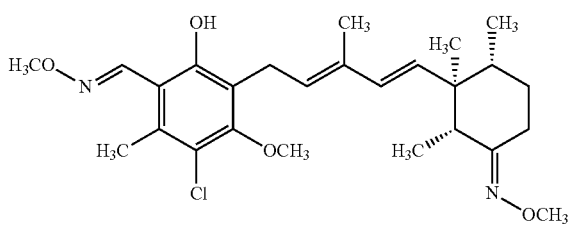 [SMILES: CO/N=C/c1c(C)c(Cl)c(OC)c(C/C=C(C)/C=C/[C@@]2(C)[C@H](C)CC/C(=N\OC)[C@@H]2C)c1O]

The titled compound was prepared from 4-O-methyl-ascochlorine by the similar manner as described in Example 4 except that O-methyl hydroxyamine hydrochloride was used instead of hydroxyamine hydrochloride.

LC-MS: (ES, m/z): 477 [M+H]$^+$

H-NMR: (DMSO, 400 MHz, ppm): δ 10.80 (s, 1H), 8.64 (s, 1H), 5.89 (d, J=16.1 Hz, 1H), 5.46-5.37 (m, 2H), 3.96 (s, 3H), 3.75 (s, 3H), 3.71 (s, 3H), 3.45 (d, J=7.2 Hz, 2H), 3.15-3.11 (m, 1H), 2.41 (s, 3H), 2.223 (q, J=6.8 Hz, 1H), 1.84 (s, 3H), 1.66 (m, 3H), 1.20 (td, J=14.4, 13.1, 6.3 Hz, 1H), 0.80 (d, J=6.8 Hz, 3H), 0.65 (m, 6H).

Example 11

Synthesis of 4-chloro-3-(fluoromethoxy)-2-[(2E,4E)-5-[(1R,2R,3E,6R)-3-(methoxyimino)-1,2,6-trimethylcyclohexyl]-3-methylpenta-2,4-dien-1-yl]-6-[(1E)-(methoxyimino)methyl]-5-methylphenol (Compound 9)

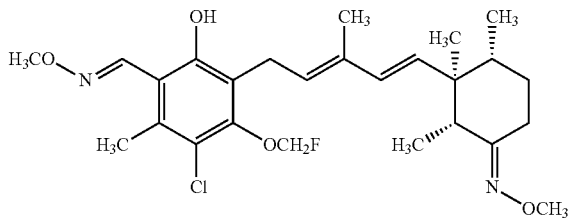

The titled compound was prepared from 4-O-fluoromethyl-ascochlorine by the similar manner as described in Example 8 except that O-methyl hydroxyamine hydrochloride was used instead of hydroxyamine hydrochloride.

LC-MS (ES, m z): [M+H]$^+$: 495.

$^1$H NMR (300 MHz, Methanol-d$_4$) δ 8.60 (s, 1H), 5.89 (d, J=16.2 Hz, 1H), 5.64 (d, J=54.3 Hz, 2H), 5.42 (t, J=7.2 Hz, 1H), 5.36 (d, J=16.2 Hz, 1H), 3.97 (s, 3H), 3.73 (s, 3H), 3.58 (d, J=7.2 Hz, 2H), 3.23-3.26 (m, 1H), 2.43 (s, 3H), 2.17 (q, J=6.9 Hz, 1H), 1.87 (s, 3H), 1.60-1.71 (m, 3H), 1.30-1.33 (m, 1H), 0.86 (d, J=6.9 Hz, 3H), 0.73 (d, J=6.6 Hz, 3H), 0.67 (s, 3H).

Example 12

Synthesis of 4-chloro-2-[(2E,4E)-5-[(1R,2R,3E,6R)-3-(hydroxyimino)-1,2,6-trimethylcyclohexyl]-3-methylpenta-2,4-dien-1-yl]-3-methoxy-6-[(1E)-(methoxyimino)methyl]-5-methylphenol (Compound 10)

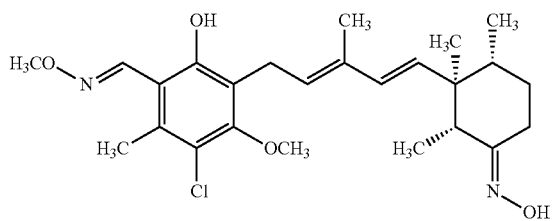

Step 1

A mixture of 3-chloro-6-hydroxy-4-methoxy-2-methyl-5-[(2E,4E)-3-methyl-5-[(1R,2R,6R)-1,2,6-trimethyl-3-oxocyclohexyl]penta-2,4-dien-1-yl]benzaldehyde (4-O-methylascochlorine, 350 mg, 0.84 mmol) and NH$_2$OMe.HCl (69.3 mg, 0.83 mmol) in pyridine (4 mL) was placed in a 50-mL round-bottom flask purged and maintained with an atmosphere of argon. The mixture was stirred overnight at room temperature and concentrated under vacuum. The residue (400 mg) was purified by Prep-HPLC with the following condition to give (2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexan-1-one (200.9 mg, 54%) as an off-white solid.

Prep-HPLC condition (2 #-AnalyseHPLC-SHIMADZU (HPLC-10)): Column, XBridge Prep C18 OBD Column, 5 um, 19*150 mm; mobile phase, Water with 10 mmol NH$_4$HCO$_3$ and CH$_3$CN (hold 80.0% CH$_3$CN in 12 min); Detector, UV 254 nm.

LC-MS (ES, m z): 448 [M+H]$^+$

H-NMR (DMSO, 300 MHz, ppm): δ 10.80 (s, 1H), 8.64 (s, 1H), 5.88 (d, J=16.0 Hz, 1H), 5.37-5.51 (m, 2H), 3.96 (s, 3H), 3.75 (s, 3H), 3.46 (d, J=6.9 Hz, 2H), 2.56 (m, 2H), 2.41 (s, 3H), 2.15 (m, 1H), 1.80-2.06 (m, 4H), 1.41-1.59 (m, 1H), 0.70 (dd, J=15.0, 6.7 Hz, 6H), 0.60 (s, 3H).

Step 2

A mixture of (2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexan-1-one (500 mg, 1.12 mmol) and NH$_2$OH.HCl (84.9 mg, 1.23 mmol, 1.10 equiv) in pyridine (5 mL) was placed in a 50-mL round-bottom flask purged and maintained with an atmosphere of argon. The mixture was stirred overnight at room temperature and then concentrated under vacuum. The residue was purified by Prep-HPLC with the following condition to give 4-chloro-2-[(2E,4E)-5-[(1R,2R,3E,6R)-3-(hydroxyimino)-1,2,6-trimethylcyclohexyl]-3-methylpenta-2,4-dien-1-yl]-3-methoxy-6-[(1E)-(methoxyimino)methyl]-5-methylphenol (246.5 mg, 48%, Compound 10) as a white solid.

Prep-HPLC condition: Column: X Bridge C18, 19*250 mm, 5 um; Mobile Phase A:Water/10 mm NH$_4$HCO$_3$, Mobile Phase B: CH$_3$CN; Flow rate: 30 m/min; Gradient: 88% B to 88% B in 8 min; 254 nm; Detector.

LC-MS (ES, m z): 463 [M+H]$^+$

H-NMR (DMSO, 300 MHz, ppm): δ 10.80 (s, 1H), 10.35 (s, 1H), 8.65 (s, 1H), 5.90 (d, J=16.1 Hz, 1H), 5.42 (m, 2H), 3.96 (s, 3H), 3.75 (s, 3H), 3.46 (d, J=7.1 Hz, 2H), 3.23 (m, 1H), 2.41 (s, 3H), 2.23 (t, J=6.8 Hz, 1H), 1.86 (s, 3H), 1.62 (d, J=11.9 Hz, 3H), 1.18 (d, J=10.5 Hz, 1H), 0.80 (d, J=6.8 Hz, 3H), 0.68 (d, J=6.6 Hz, 3H), 0.61 (s, 3H).

Example 13

Synthesis of 4-chloro-3-(fluoromethoxy)-2-[(2E,4E)-5-[(1R,2R,3E,6R)-3-(hydroxyimino)-1,2,6-trimethylcyclohexyl]-3-methylpenta-2,4-dien-1-yl]-6-[(1E)-(methoxyimino)methyl]-5-methylphenol (Compound 11)

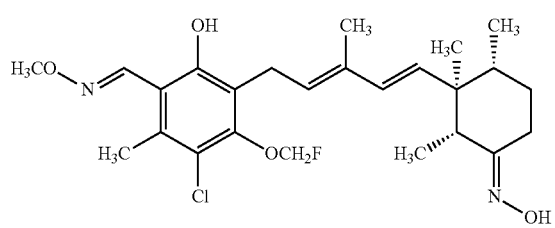

The titled compound was prepared from 4-O-fluoromethyl-ascochlorine by the similar manner as described in Example 12.

LC-MS (ES, m z): [M+H]$^+$: 481.

$^1$H NMR (300 MHz, DMSO-d$_6$) δ 10.36 (s, 1H), 8.66 (s, 1H), 5.88 (d, J=16.2 Hz, 1H), 5.72 (d, J=54.3 Hz, 2H) 5.42 (t, J=7.5 Hz, 1H), 5.37 (d, J=16.2 Hz, 1H), 3.95 (s, 3H) 3.50 (m, 2H), 3.23 (m, 2H), 2.43 (s, 3H), 2.21 (q, J=6.6 Hz, 1H), 1.84 (s, 3H), 1.59 (m, 3H), 1.25 (m, 1H), 0.80 (d, J=6.6 Hz, 3H), 0.68 (d, J=6.9 Hz, 3H), 0.61 (s, 3H).

Example 14

Synthesis of 4-chloro-2-[(2E,4E)-5-[(1R,2R,3E,6R)-3-[[2-(dimethylamino)ethoxy]imino]-1,2,6-trimethylcyclohexyl]-3-methylpenta-2,4-dien-1-yl]-3-methoxy-6-[(1E)-(methoxyimino)methyl]-5-methylphenol (Compound 15)

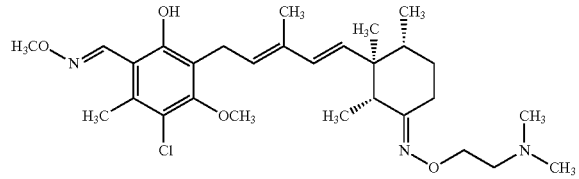 [SMILES: CO/N=C/c1c(C)c(Cl)c(OC)c(C/C=C(C)/C=C/[C@@]2(C)[C@H](C)CC/C(=N\OCCN(C)C)[C@@H]2C)c1O]

The titled compound was prepared by the method similar to that described in Example 12 except that O-(2-(dimethylamino)ethyl)hydroxyamine hydrochloride was used instead of hydroxyamine hydrochloride.

LC-MS (ES, m/z): 534 [M+H]$^+$

H-NMR (DMSO, 400 MHz, ppm): δ10.79 (s, 1H), 8.63 (s, 1H), 5.89 (d, J=16.1 Hz, 1H), 5.33-5.48 (m, 2H), 3.98 (m, 5H), 3.74 (s, 3H), 3.45 (d, J=7.2 Hz, 2H), 3.13 (m, 2H), 2.46 (m, 2H), 2.39 (s, 3H), 2.23 (q, J=6.8 Hz, 1H), 2.14 (s, 6H), 1.85 (d, J=1.3 Hz, 3H), 1.57-1.74 (m, 3H), 1.19 (m, 1H), 0.78 (d, J=6.7 Hz, 3H), 0.66 (d, J=6.5 Hz, 3H), 0.61 (s, 3H).

Example 15

Synthesis of 4-chloro-3-methoxy-6-[(1E)-(methoxyimino)methyl]-5-methyl-2-[(2E,4E)-3-methyl-5-[(1R,2R,3E,6R)-1,2,6-trimethyl-3-[[2-(morpholin-4-yl)ethoxy]imino]cyclohexyl]penta-2,4-dien-1-yl]phenol (Compound 16)

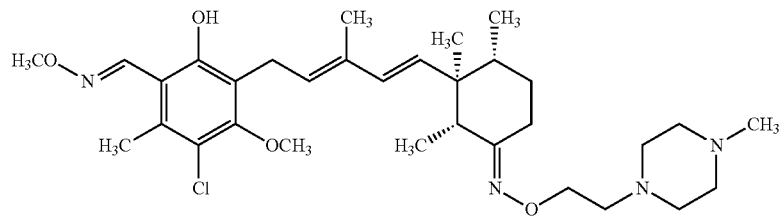

The titled compound was prepared by the method similar to that described in Example 12 except that O-(2-(morpholin-4-yl)ethyl)hydroxyamine hydrochloride was used instead of hydroxyamine hydrochloride.

LC-MS (ES, m z): 576 [M+H]$^+$

H-NMR (CD$_3$CN, 300 MHz, ppm): δ 8.55 (s, 1H), 5.93 (d, J=16.1 Hz, 1H), 5.36-5.50 (m, 2H), 4.07 (t, J=5.7 Hz, 2H), 3.94 (s, 3H), 3.75 (s, 3H), 3.51 (m, 6H), 3.14-3.28 (m, 1H), 2.55 (m, 2H), 2.46 (s, 7H), 2.20 (t, J=6.8 Hz, 1H), 1.89 (d, J=1.1 Hz, 3H), 1.58-1.72 (m, 3H), 1.25 (m, 1H), 0.81 (d, J=6.8 Hz, 3H), 0.67 (m, 6H).

Example 16

Synthesis of 4-chloro-3-methoxy-6-[(1E)-(methoxyimino)methyl]-5-methyl-2-[(2E,4E)-3-methyl-5-[(1R,2R,3E,6R)-1,2,6-trimethyl-3-[[2-(4-methylpiperazin-1-yl)ethoxy]imino]cyclohexyl]penta-2,4-dien-1-yl]phenol (Compound 17)

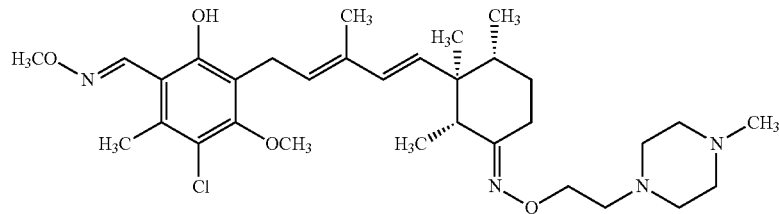 [SMILES: CO/N=C/c1c(C)c(Cl)c(OC)c(C/C=C(C)/C=C/[C@@]2(C)[C@H](C)CC/C(=N\OCCN3CCN(C)CC3)[C@@H]2C)c1O]

The titled compound was prepared by the method similar to that described in Example 12 except that O-(2-(N-methylpipearzin-4-yl)ethyl)hydroxyamine hydrochloride was used instead of hydroxyamine hydrochloride.

LC-MS (ES, m z): 589 [M+H]$^+$

H-NMR (CDCl$_3$, 400 MHz, ppm): δ 10.80 (s, 1H), 8.50 (s, 1H), 5.92 (t, J=16.0 Hz, 1H), 5.51 (m, 1H), 5.33 (m, 1H), 4.19 (m, 2H), 3.99 (s, 3H), 3.83 (s, 3H), 3.56 (t, J=7.2 Hz, 2H), 3.28 (m, 1H), 2.42-2.70 (m, 13H), 2.32 (s, 3H), 2.14 (m, 1H), 1.93 (s, 3H), 1.63 (m, 3H), 1.29 (m, 1H), 0.88 (d, J=6.8 Hz, 3H), 0.71 (m, 6H).

Example 17

Synthesis of ethyl 2-([[[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetate (Compound 18)

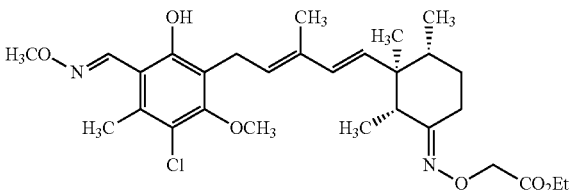

The titled compound was prepared by the method similar to that described in Example 12 except that ethyl 2-(aminooxy)acetate was used instead of hydroxyamine hydrochloride.

LC-MS (ES, m z): [M+H]$^+$: 549

$^1$H NMR (300 MHz, DMSO-d$_6$): δ 10.74 (s, 1H), 8.60 (s, 1H), 5.86 (d, J=16.2 Hz, 1H), 5.41 (t, J=7.0 Hz, 1H), 5.35 (d, J=16.2 Hz, 1H), 4.51 (s, 2H), 4.06 (q, J=7.1 Hz, 2H), 3.71 (s, 3H), 3.42 (d, J=7.2 Hz, 2H), 3.28 (s, 1H), 3.18 (dd, J=12.9, 4.1 Hz, 1H), 2.37 (s, 3H), 2.24 (q, J=6.8 Hz, 1H), 1.81 (d, J=1.3 Hz, 3H), 1.79-1.56 (m, 3H), 1.31-1.17 (m, 1H), 1.14 (t, J=7.1 Hz, 3H), 0.71 (d, J=6.7 Hz, 3H), 0.64 (d, J=6.5 Hz, 3H), 0.58 (s, 3H).

Example 18

Synthesis of 4-chloro-2-[(2E,4E)-5-[(1R,2R,3S,6R)-3-hydroxy-1,2,3,6-tetramethylcyclohexyl]-3-methyl-penta-2,4-dien-1-yl]-3-methoxy-6-[(1E)-(methoxyimino)methyl]-5-methylphenol (Compound 14-1)

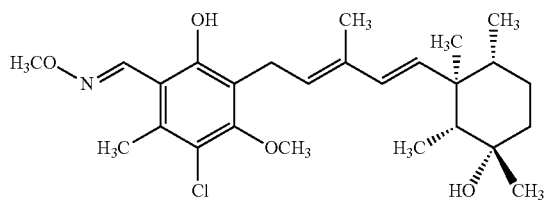 [SMILES: CO/N=C/c1c(C)c(Cl)c(OC)c(C/C=C(C)/C=C/[C@@]2(C)[C@H](C)CC[C@](C)(O)[C@@H]2C)c1O]

A mixture of 3-chloro-6-hydroxy-5-[(2E,4E)-5-[(1R,2R,3S,6R)-3-hydroxy-1,2,3,6-tetramethylcyclohexyl]-3-methylpenta-2,4-dien-1-yl]-4-methoxy-2-methylbenzaldehyde [Compound 1, Example 2] (350 mg, 0.80 mmol) and methoxylamine hydrochloride (85 mg, 1.02 mmol) in pyridine (5 mL) was placed in a 50-mL round-bottom flask. The mixture was stirred for 12 h at 10 to 15° C. and concentrated under vacuum. The residue was purified by Prep-HPLC with the following condition to give the titled compound (209.3 mg, 55%) as a light yellow solid.

Prep-HPLC condition (2 #-AnalyseHPLC-SHIMADZU (HPLC-10)): Column, XBridge BEH C18 OBD Prep Column, 5 μm, 19 mm 250 mm; mobile phase, Water with 10 mmol NH$_4$HCO$_3$ and CH$_3$CN (hold 90.0% CH$_3$CN in 9 min); Detector, uv 254&220 nm.

LC-MS (ES, m z): [M–H] 462

H-NMR (DMSO, 400 MHz ppm): δ 10.79 (s, 1H), 8.64 (s, 1H), 5.82 (m, 1H), 5.39 (m. 1H), 5.22 (m, 1H), 3.96 (s. 3H), 3.74 (m, 4H), 3.32-3.45 (m, 2H), 2.50 (s, 3H), 1.81 (m, 3H), 1.47-1.59 (m, 2H), 1.21-1.38 (m, 3H), 1.13 (m, 1H), 1.04 (s, 3H), 0.85 (m, 3H), 0.74 (m, 3H), 0.64 (m, 3H).

Example 19

Synthesis of 2-([[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetic acid (Compound 19)

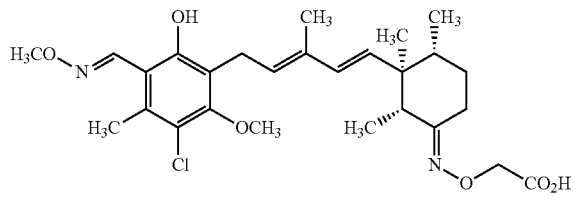 [SMILES: CO/N=C/c1c(C)c(Cl)c(OC)c(C/C=C(C)/C=C/[C@@]2(C)[C@H](C)CC/C(=N\OCC(=O)O)[C@@H]2C)c1O]

A solution of ethyl 2-([[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetate [Compound 18, Example 17] (350 mg, 0.64 mmol) was placed in a 25-mL round-bottom flask, followed by addition of a solution of lithium hydroxide (76 mg, 3.17 mmol) in water/THF (0.5/1 mL). The mixture was stirred overnight at room temperature. The pH value of the mixture was adjusted to 4 with aqueous hydrochloride acid (1N). The reaction mixture was extracted with dichloromethane (2 mL×2). The organic layer was combined, and then concentrated under vacuum. The residue was purified by Prep-HPLC with the following condition to give 2-([[[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetic acid (300 mg, 90%, Compound 19) as a white solid.

Prep-HPLC (2 #-AnalyseHPLC-SHIMADZU(HPLC-10)): Column, XBridge Shield RP18 OBD Column, 5 um, 19*150 mm; mobile phase, WATER WITH 0.05% TFA and CH$_3$CN (hold 72.0% CH$_3$CN in 11 min); Detector, UV 254 nm.

LC-MS: (ES, m z): [M+H]$^+$: 521.

$^1$H NMR (300 MHz, DMSO-d$_6$) δ 10.76 (s, 1H), 8.60 (s, 1H), 5.86 (d, J=16.2 Hz, 1H), 5.41 (t, J=6.9 Hz, 1H), 5.35 (d, J=16.2 Hz, 1H), 4.42 (s, 2H), 3.92 (s, 3H), 3.42 (d, J=7.1 Hz, 2H), 3.13-3.25 (m, 1H), 2.37 (s, 3H), 2.23 (q, J=6.8 Hz, 1H), 1.82 (d, J=1.4 Hz, 3H), 1.56-1.76 (m, 3H), 1.22 (s, 1H), 0.71 (d, J=6.8 Hz, 3H), 0.64 (d, J=6.5 Hz, 3H), 0.59 (s, 3H).

Example 20

Synthesis of 3-chloro-4-(fluoromethoxy)-6-hydroxy-2-methyl-5-[(2E,4E)-3-methyl-5-[(1R,2R,3E,6R)-1,2,6-trimethyl-3-[[2-(morpholin-4-yl)ethoxy]imino]cyclohexyl]penta-2,4-dien-1-yl]benzaldehyde (Compound 12)

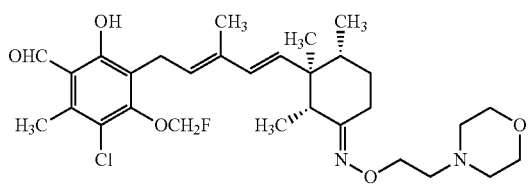

The titled compound was prepared by the similar method as described in Example 6 except that O-2-(morpholin-4-yl)ethyl hydroxyamine hydrochloride was used instead of hydroxyamine hydrochloride.

LC-MS (ES, m z): [M+H]$^+$: 565

$^1$H NMR (300 MHz, Chloroform-d) δ 12.55 (s, 1H), 10.29 (s, 1H), 5.91 (d, J=16.0 Hz, 1H), 5.70 (d, J=54.3 Hz, 1H), 5.46 (t, J=7.4 Hz, 1H), 5.34 (d, J=16.0 Hz, 1H), 4.19 (t, J=5.8 Hz, 2H), 3.72 (m, 4H), 3.61 (d, J=7.3 Hz, 2H), 3.21-3.36 (m, 1H), 2.67 (d, J=9.0 Hz, 5H), 2.55 (m, 4H), 2.15 (q, J=6.7 Hz, 1H), 1.52-1.74 (m, 3H), 1.30 (m, 1H), 0.89 (d, J=6.7 Hz, 3H), 0.73 (d, J=6.4 Hz, 3H), 0.69 (s, 3H).

Example 21

Synthesis of 4-chloro-2-[(2E,4E)-5-[(1R,2R,6R)-3-(ethylamino)-1,2,6-trimethylcyclohexyl]-3-methylpenta-2,4-dien-1-yl]-3-methoxy-6-[(1E)-(methoxyimino)methyl]-5-methylphenol (Compound 21)

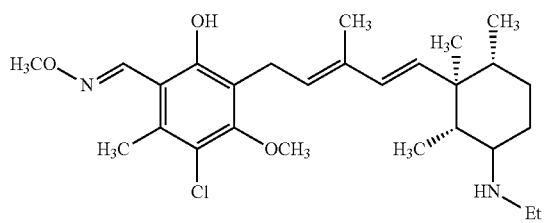 [SMILES: CCNC1CC[C@@H](C)[C@](C)(/C=C/C(C)=C/Cc2c(O)c(/C=N/OC)c(C)c(Cl)c2OC)[C@H]1C]

Step 1

A mixture of placed (2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexan-1-one [Example 12, step 1] (3 g, 6.70 mmol), Ti(i-PrO)$_4$ (15.2 g, 53.52 mmol), ethylamine hydrochloride (2.2 g, 26.83 mmol) and MS 4A (Ig) in THF (30 mL) was placed in a 250-mL round-bottom flask. The mixture was stirred overnight at 68° C. in an oil bath. The resulting mixture was diluted with 200 mL of ethyl acetate followed by addition of 10 mL of saturated ammonium chloride. The mixture was filtered, and the filtrate was dried over anhydrous magnesium sulfate and concentrated under vacuum to give 4-chloro-2-[(2E,4E)-5-[(1R,2R,3E,6R)-3-(ethylimino)-1,2,6-trimethylcyclohexyl]-3-methylpenta-2,4-dien-1-yl]-3-methoxy-6-[(1E)-(methoxyimino)methyl]-5-methylphenol (1.2 g, crude) as a brown solid.

Step 2

A solution of 4-chloro-2-[(2E,4E)-5-[(1R,2R,3E,6R)-3-(ethylimino)-1,2,6-trimethylcyclohexyl]-3-methylpenta-2,4-dien-1-yl]-3-methoxy-6-[(1E)-(methoxyimino)methyl]-5-methylphenol (1.2 g, 2.53 mmol) and sodium triacetoxyborohydride (1.07 g, 5.05 mmol, 2.00 equiv) in dichloromethane (20 mL) was placed in a 100-mL round-bottom flask. The mixture was stirred for 5 h at room temperature. The mixture was filtered, and the filtrate was concentrated under vacuum. The residue was purified by Flash-Prep-HPLC with the following condition to give a crude product (350 mg), which was purified by Chiral-Prep-HPLC with the following condition to give 4-chloro-2-[(2E,4E)-5-[(1R,2R,6R)-3-(ethylamino)-1,2,6-trimethylcyclohexyl]-3-methylpenta-2,4-dien-1-yl]-3-methoxy-6-[(1E)-(methoxyimino)methyl]-5-methylphenol (211.4 mg, 18%, Compound 21) as an orange solid.

Flash-Prep-HPLC condition (CombiFlash-1): Column, C18 silica gel; mobile phase, water/acetonitrile=1:0 increasing to water/acetonitrile=0:1 within 40 min; Detector, UV 254 nm.

Chiral-Prep-HPLC condition: Column: XBridge Shield RP18 OBD Column, 5 um, 19*150 mm; Mobile Phase A: Water with 10 mmol NH$_4$HCO$_3$, Mobile Phase B: ACN; Flow rate: 20 mL/min; Gradient: 75% B to 95% B in 10 min; Detector 254 nm.

LC-MS (ES, m/z): 477 [M+H]$^+$

H-NMR (DMSO, 300 MHz, ppm): δ 10.71-10.87 (br, 1H), 8.644 (s, 1H), 5.82 (t, J=16.2 Hz, 1H), 5.39 (m, 1H), 5.25 (m, 1H), 3.96 (s, 3H), 3.75 (s, 3H), 3.44 (d, J=6.9 Hz, 2H), 2.57-2.66 (m, 2H), 2.51 (s, 3H), 2.28-2.36 (m, 1H), 1.74-1.82 (m, 4H), 1.12-1.50 (m, 6H), 0.98 (m, 3H), 0.86 (m, 3H), 0.77 (m, 3H), 0.63 (m, 3H).

Example 22

Synthesis of 4-chloro-2-[(2E,4E)-5-[(1R,2R,6R)-3-(cyclopropylamino)-1,2,6-trimethylcyclohexyl]-3-methylpenta-2,4-dien-1-yl]-3-methoxy-6-[(1E)-(methoxyimino)methyl]-5-methylphenol (Compound 23)

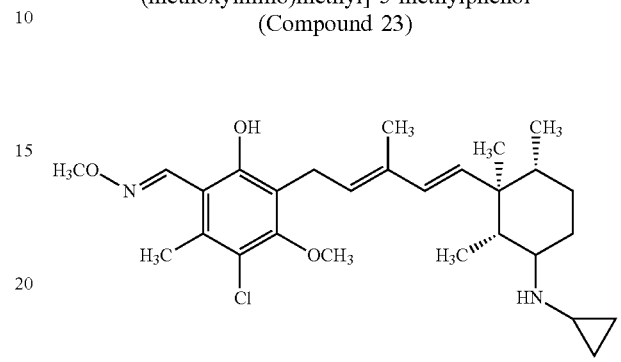

The titled compound was prepared by the similar method described in Example 21 except that cyclopropyl amine was used instead of ethylamine.

LC-MS (ES, m z): 489 [M+H]$^+$

H-NMR (DMSO, 300 MHz, ppm): δ 10.79 (s, 1H), 8.64 (s, 1H), 5.80 (t, J=16.2 Hz, 1H), 5.37 (m, 1H), 5.24 (m, 1H), 3.96 (s, 3H), 3.74 (s, 3H), 3.44 (d, J=6.3 Hz, 2H), 2.74 (m, 1H), 2.41 (s, 3H), 1.96 (m, 2H), 1.82 (s, 3H), 1.41-1.57 (m, 3H), 1.15-1.40 (m, 3H), 0.80 (s, 3H), 0.73 (m, 3H), 0.64 (m, 3H), 0.39 (m, 1H), 0.25 (m, 2H), 0.15 (m, 1H).

Example 23

Synthesis of 2-[(2E,4E)-5-[(1R,2R,6R)-3-amino-1,2,6-trimethylcyclohexyl]-3-methylpenta-2,4-dien-1-yl]-4-chloro-3-methoxy-6-[(1E)-(methoxyimino)methyl]-5-methylphenol (Compound 24)

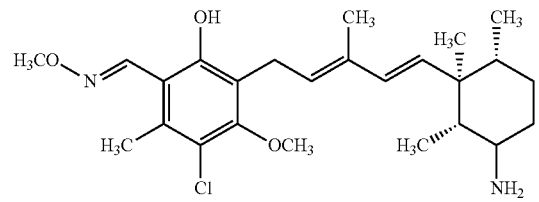 [SMILES: CO/N=C/c1c(C)c(Cl)c(OC)c(C/C=C(C)/C=C/[C@@]2(C)[C@H](C)CCC(N)[C@@H]2C)c1O]

A mixture of (2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexan-1-one (3 g, 6.70 mmol) [Example 12, Step 1], NaBH$_3$CN (2.75 g, 43.76 mmol) and NH$_4$OAc (20 g, 40.00 equiv) in ethanol (100 mL) was placed in a 250-mL round-bottom flask purged and maintained with an atmosphere of argon. The resulting mixture was stirred overnight at 70° C. in an oil bath. The resulting mixture was concentrated under vacuum. The residue was diluted with H$_2$O (80 mL). The mixture was extracted with ethyl acetate (200 mL×3) and the organic layer was combined, then concentrated under vacuum. The residue was purified by Flash-Prep-HPLC with the following condition to give the titled compound (1.5 g, 50%, Compound 24) as a yellow solid.

Flash-Prep-HPLC condition (IntelFlash-1): Column, C18 silica gel; mobile phase, $CH_3CN: H_2O=0:95$ increasing to $CH_3CN: H_2O=95:5$ within 55 min; Detector, UV 254 nm.

LC-MS: (ES, m z): $[M+H]^+$ 449

H-NMR: ($CDCl_3$, 400 MHz ppm): ☐ 10.77 (s, 1H), 8.50 (s, 1H), 5.93 (d, J=16.4 Hz, 1H), 5.52 (m, 1H), 5.19 (m, 1H), 3.99 (s, 3H), 3.82 (s, 3H), 3.54 (m, 2H), 2.42 (s, 3H), 2.04-2.23 (m, 1H), 1.90 (m, 3H), 1.25-1.85 (m, 6H), 0.91-1.04 (m, 5H), 0.70-0.78 (m, 4H).

Example 24

Synthesis of 4-chloro-3-methoxy-6-[(1E)-(methoxyimino)methyl]-5-methyl-2-[(2E,4E)-3-methyl-5-[(1R,2R,6R)-1,2,6-trimethyl-3-[(oxetan-3-yl)amino] cyclohexyl]penta-2,4-dien-1-yl]phenol (Compound 25)

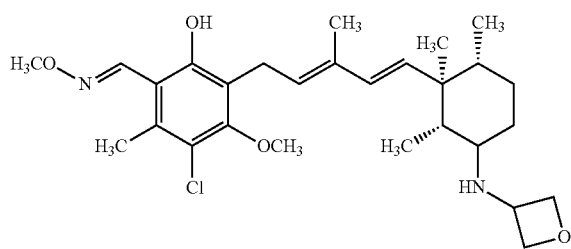 [SMILES: CO/N=C/c1c(C)c(Cl)c(OC)c(C/C=C(C)/C=C/[C@@]2(C)[C@H](C)CCC(NC3COC3)[C@@H]2C)c1O]

Into a 50-mL sealed tube, a solution of 2-[(2E,4E)-5-[(1R,2R,6R)-3-amino-1,2,6-trimethylcyclohexyl]-3-methylpenta-2,4-dien-1-yl]-4-chloro-3-methoxy-6-[(1E)-(methoxyimino)methyl]-5-methylphenol (Compound 24; 1 g, 2.23 mmol), sodium triacetoxyborohydride (STAB, 709.8 mg, 3.35 mmol) and oxetan-3-one (353.6 mg, 4.91 mmol) in DCM (12 mL) were placed. The mixture was stirred for 18 h at room temperature and then concentrated under vacuum. The residue was purified by Prep-HPLC with the following condition to give the titled compound (239.2 mg, 21%, Compound 25) as an off-white solid.

Prep-HPLC condition (2 #-AnalyseHPLC-SHIMADZU (HPLC-10)): Column, XBridge Shield RP18 OBD Column, 5 um, 19*150 mm; mobile phase, Water with 10 mmol $NH_4HCO_3$ and $CH_3CN$ (hold 82.0% ACN in 10 min); Detector, UV 254 nm.

LC-MS: (ES, m z): $[M+H]^+$ 505

H-NMR: (DMSO, 400 MHz ppm): δ10.80 (s, 1H), 8.66 (s, 1H), 5.84 (d, J=16.4 Hz, 1H), 5.41 (m, 1H), 5.25 (d, J=15.6 Hz, 1H), 4.60 (m, 2H), 4.27-4.36 (m, 2H), 4.38 (s, 3H), 3.83 (m, 1H), 3.76 (s, 3H), 3.46 (d, J=7.2 Hz, 2H), 2.42 (s, 3H), 1.84 (s, 3H), 1.45-1.58 (m, 3H), 1.35 (m, 2H), 1.21 (m, 1H), 0.89 (s, 3H), 0.81 (d, J=7.2 Hz, 3H), 0.67 (m, 3H).

Example 25

Synthesis of 3-chloro-5-[(2E,4E)-5-[(1R,2R,6R)-3-(ethylamino)-1,2,6-trimethylcyclohexyl]-3-methylpenta-2,4-dien-1-yl]-6-hydroxy-4-methoxy-2-methylbenzaldehyde (Compound 20)

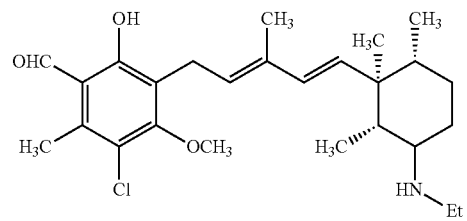 [SMILES: CCNC1CC[C@@H](C)[C@](C)(/C=C/C(C)=C/Cc2c(O)c(C=O)c(C)c(Cl)c2OC)[C@H]1C]

A solution of 4-chloro-2-[(2E,4E)-5-[(1R,2R,6R)-3-(ethylamino)-1,2,6-trimethylcyclohexyl]-3-methylpenta-2,4-dien-1-yl]-3-methoxy-6-[(1E)-(methoxyimino)methyl]-5-methylphenol [Compound 21, Example 21] (500 mg, 1.05 mmol), formaldehyde (425 mg, 5.25 mmol, 5.00 equiv, 37%) and hydrochloride acid (500 mg, 5.3 mmol, 5.00 equiv, 38%) in THF/water (20 mL/2 mL) was placed in a 30-mL sealed tube. The mixture was stirred overnight at 100° C. and then concentrated under vacuum. The residue was purified by Prep-HPLC with the following condition to give the titled compound (55.4 mg, 9.4%, Compound 20) as an off-white solid.

Prep-HPLC condition (2 #-AnalyseHPLC-SHIMADZU (HPLC-10)): Column, Gemini-NX 5 u C18 110A, AXIA Packed, 150×21.2 mm; mobile phase, Column: Mobile Phase A: Water with 10 mmol $CF_3COOH$, Mobile Phase B: $CH_3CN$; Flow rate: 30 m/min; Gradient: 60% B to 95% B in 10 min; 254 nm; Detector, uv 254 nm.

LC-MS (ES, m z): 448 $[M+H]^+$

H-NMR (DMSO, 300 MHz, ppm) 12.62 (br, 1H), 10.27 (br, 1H), 7.90 (br, 1H), 7.43 (br, 1H), 5.94 (d, J=16.2 Hz, 1H), 5.43 (t, J=7.5 Hz, 1H), 5.34 (d, J=15.9 Hz, 1H), 3.82 (s, 3H), 3.47 (d, J=7.5 Hz, 2H), 3.28 (m, 1H), 2.96 (m, 2H), 2.62 (s, 3H), 1.85 (m, 5H), 1.70 (m, 1H), 1.50 (s, 3H), 1.20 (m, 3H), 0.88 (m, 3H), 0.83 (m, 3H), 0.74 (m, 3H).

Example 26

Synthesis of 3-chloro-5-[(2E,4E)-5-[(1R,2R,6R)-3-(cyclopropylamino)-1,2,6-trimethylcyclohexyl]-3-methylpenta-2,4-dien-1-yl]-6-hydroxy-4-methoxy-2-methylbenzaldehyde (Compound 22)

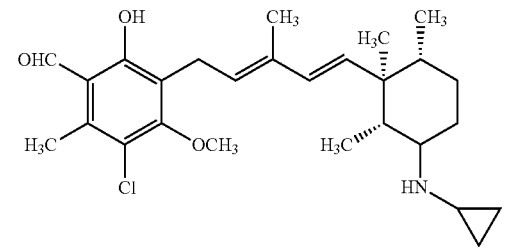 [SMILES: COc1c(Cl)c(C)c(C=O)c(O)c1C/C=C(C)/C=C/[C@@]1(C)[C@H](C)CCC(NC2CC2)[C@@H]1C]

The titled compound was prepared from Compound 23 (Example 22) by the similar method as described in Example 25.

LC-MS (ES, m z): 460 [M+H]+

H-NMR (DMSO, 300 MHz, ppm): 12.60 (br, 1H), 10.27 (s, 1H), 5.80 (d, J=16.2 Hz, 1H), 5.36 (t, J=7.2 Hz, 1H), 5.25 (d, J=15.9 Hz, 1H), 3.81 (s, 3H), 3.42 (d, J=6.9 Hz, 2H), 2.75 (m, 1H), 2.62 (s, 3H), 1.96 (m, 2H), 1.82 (s, 3H), 1.20-1.61 (m, 6H), 0.80 (m, 3H), 0.71 (m, 3H), 0.63 (m, 3H), 0.35-0.47 (m, 1H), 0.24-0.31 (m, 2H), 0.06-0.18 (m, 1H).

Example 27

Synthesis of 3-chloro-5-[(2E,4E)-5-[(1R,2R,6R)-3-(cyclopropylamino)-1,2,6-trimethylcyclohexyl]-3-methylpenta-2,4-dien-1-yl]-4-(fluoromethoxy)-6-hydroxy-2-methylbenzaldehyde (Compound 13)

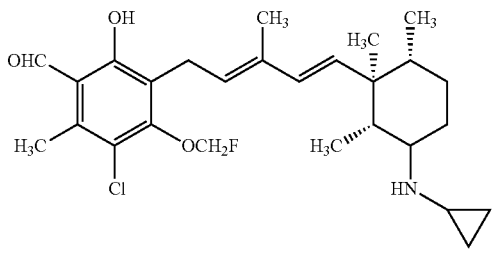

Step 1

Into a 50-mL round-bottom flask, was placed a solution of (2R,3R,4R)-3-[(1E,3E)-5-[3-chloro-5-(diethoxymethyl)-2-(fluoromethoxy)-6-hydroxy-4-methylphenyl]-3-methyl-penta-1,3-dien-1-yl]-2,3,4-trimethylcyclohexan-1-one [Example 2] (900 mg, 1.76 mmol), MS 4A (200 mg) and cyclopropanamine (2 g, 35.03 mmol, 20.00 equiv) in ethanol (10 mL). The resulting solution was stirred overnight at 30° C. The resulting mixture was concentrated under vacuum to give 4-chloro-2-[(2E,4E)-5-[(1R,2R,3E,6R)-3-(cyclopropylimino)-1,2,6-trimethylcyclohexyl]-3-methylpenta-2,4-dien-1-yl]-6-(diethoxymethyl)-3-(fluoromethoxy)-5-methylphenol (0.9 g, 93%) as a solid.

Step 2

A solution of 4-chloro-2-[(2E,4E)-5-[(1R,2R,3E,6R)-3-(cyclopropylimino)-1,2,6-trimethylcyclohexyl]-3-methyl-penta-2,4-dien-1-yl]-6-(diethoxymethyl)-3-(fluoromethoxy)-5-methylphenol (1.1 g, 2.00 mmol) and sodium borohydride acetate (464 mg, 2.19 mmol) in ethanol (20 mL) was placed in a 100-mL round-bottom flask. The mixture was stirred for 3 h at room temperature and concentrated under vacuum. The residue was purified by silica gel column chromatography with ethyl acetate/petroleum ether (1:10) to give 4-chloro-2-[(2E,4E)-5-[(1R,2R,6R)-3-(cyclopropylamino)-1,2,6-trimethylcyclohexyl]-3-methyl-penta-2,4-dien-1-yl]-6-(diethoxymethyl)-3-(fluoromethoxy)-5-methylphenol (460 mg, 42%) as a solid.

Step 3

A solution of 4-chloro-2-[(2E,4E)-5-[(1R,2R,6R)-3-(cyclopropylamino)-1,2,6-trimethylcyclohexyl]-3-methyl-penta-2,4-dien-1-yl]-6-(diethoxymethyl)-3-(fluoromethoxy)-5-methylphenol (460 mg, 0.83 mmol) in THF/water/acetic acid (10/20/10 mL) was placed in a 100-mL round-bottom flask. The mixture was stirred for 3 h at room temperature and concentrated under vacuum. The residue was dissolved in water (10 mL). The mixture was extracted with ethyl acetate (20 mL) and the organic layer was combined, then concentrated under vacuum. The residue was purified by Prep-HPLC with the following condition of 3-chloro-5-[(2E,4E)-5-[(1R,2R,6R)-3-(cyclopropylamino)-1,2,6-trimethylcyclohexyl]-3-methylpenta-2,4-dien-1-yl]-4-(fluoromethoxy)-6-hydroxy-2-methylbenzaldehyde (206.7 mg, 52%, Compound 13) as a light yellow solid.

Prep-HPLC condition (2 #-AnalyseHPLC-SHIMADZU (HPLC-10)): Column, Gemini-NX C18 AXAI Packed, 21.2×150 mm 5 um 11 nm; mobile phase, Water with 10 mmol NH4HCO3 and CH3CN (hold 95.0% CH3CN in 8 min); Detector, uv 254 nm.

LC-MS (ES, m z): [M+H]+: 478.

H NMR (300 MHz, DMSO-d6) δ 10.26 (s, 1H), 5.79 (d, J=154.3 Hz, 2H), 5.78 (d, J=16.2 Hz, 1H) 5.34 (t, J=7.2 Hz, 1H), 5.25 (d, J=16.2 Hz, 1H), 3.48 (d, J=6.9 Hz, 2H), 2.76 (m, 1H), 2.64 (s, 3H), 1.95-2.08 (m, 2H), 1.80 (s, 3H), 1.20-1.48 (m, 5H), 0.79 (s, 3H), 0.69 (d, J=7.2 Hz, 3H), 0.59 (d, J=6.3 Hz, 3H), 035 (m, 1H), 0.24 (m, 1H), 0.11 (m, 1H).

Example 28

Synthesis of 2-([[[(1E,2R,3R,4R)-3-[(1E,3E)-5-[3-chloro-2-(fluoromethoxy)-5-formyl-6-hydroxy-4-methylphenyl]-3-methylpenta-1,3-dien-1-yl]-2,3,4-trimethylcyclohexylidene]amino]oxy)acetic Acid (Compound 26)

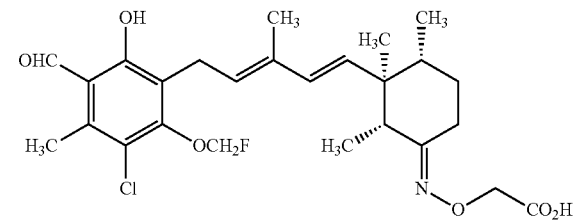

Step 1

A solution of (2R,3R,4R)-3-[(1E,3E)-5-[3-chloro-5-(diethoxymethyl)-2-(fluoromethoxy)-6-hydroxy-4-methylphenyl]-3-methylpenta-1,3-dien-1-yl]-2,3,4-trimethylcyclohexan-1-one [Example 2] (1.5 g, 2.94 mmol), Cs2CO3 (479 mg, 1.47 mmol) and ethyl 2-(aminooxy)acetate oxalic acid salt (605 mg, 2.89 mmol) in ethanol (10 mL) was placed in a 100-mL round-bottom flask. The mixture was stirred for 2 h at room temperature. The reaction mixture was diluted with water (10 mL), and extracted with ethyl acetate (10 mL×2). The organic layer was combined, and then concentrated under vacuum. The residue was purified by Flash-Prep-HPLC with the following condition to give ethyl 2-([[[(1E,2R,3R,4R)-3-[(1E,3E)-5-[3-chloro-5-(diethoxymethyl)-2-(fluoromethoxy)-6-hydroxy-4-methylphenyl]-3-methylpenta-1,3-dien-1-yl]-2,3,4-trimethylcyclohexylidene]amino]oxy)acetate (1.0 g, 56%) as a light yellow solid.

Flash-Prep-HPLC condition (IntelFlash-1): Column, C18 silica gel; mobile phase, CH3CN/H2O=60:40 increasing to CH3CN/H2O=95:5 within 40 min; Detector, UV 254 nm.

LC-MS (ES, m/z): 612 [M+H]+

Step 2

A mixture of ethyl 2-([[[(1E,2R,3R,4R)-3-[(1E,3E)-5-[3-chloro-5-(diethoxymethyl)-2-(fluoromethoxy)-6-hydroxy-4-methylphenyl]-3-methylpenta-1,3-dien-1-yl]-2,3,4-trimethylcyclohexylidene]amino]oxy)acetate (1 g, 1.63 mmol), lithium hydroxide (117 mg, 3.00 equiv) in THF/H2O (1:1, 30 mL) was placed in a 100-mL round-bottom flask. The mixture was stirred for 2 h at room temperature. Then (15 mL) was added to the solution. The resulting solution was stirred for an additional 6 h at room temperature. The resulting mixture was concentrated under vacuum and diluted with 20 mL of water. The mixture was extracted with of ethyl acetate (20 mL×2). The organic layer was combined, and then concentrated under vacuum. The residue was purified by Flash-Prep-HPLC with the following condition to give 2-([[(1E,2R,3R,4R)-3-[(1E,3E)-5-[3-chloro-2-(fluoromethoxy)-5-formyl-6-hydroxy-4-methylphenyl]-3-methylpenta-1,3-dien-1-yl]-2,3,4-trimethylcyclohexylidene]amino]oxy)-acetic acid (533.3 mg, 64%, Compound 26) as a light yellow solid.

Flash-Prep-HPLC condition (IntelFlash-1): Column, C18 silica gel; mobile phase, $CH_3CN/H_2O$=55:45 increasing to $CH_3CN/H_2O$=95:5 within 45 min; Detector, UV 254 nm.

LC-MS (ES, m z): $[M+H]^+$: 510.

H-NMR (300 MHz, DMSO-$d_6$) δ12.58 (s, 2H), 10.30 (s, 1H), 5.88 (d, J=16.2 Hz, 1H), 5.79 (d, J=53.7 Hz, 2H), 5.40 (d, J=16.2 Hz, 1H), 5.38 (m, 1H), 4.46 (s, 2H), 3.50 (d, J=7.2 Hz, 2H), 3.23 (dd, J=12.7, 4.0 Hz, 1H), 2.64 (s, 3H), 2.27 (q, J=6.7 Hz, 1H), 1.84 (s, 3H), 1.82-1.59 (m, 3H), 1.35-1.19 (m, 1H), 0.75 (d, J=6.6 Hz, 3H), 0.68 (d, J=6.6 Hz, 3H), 0.62 (s, 3H).

Example 29

Synthesis of 2-([[(1E,2R,3R,4R)-3-[(1E,3E)-5-[3-chloro-2-(fluoromethoxy)-6-hydroxy-5-[(1E)-(hydroxyimino)methyl]-4-methylphenyl]-3-methylpenta-1,3-dien-1-yl]-2,3,4-trimethylcyclohexylidene]amino]oxy)acetic Acid (Compound 27)

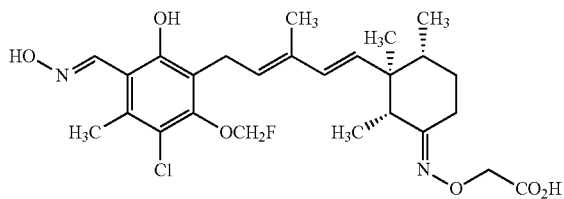

Step 1

A solution of 3-chloro-4-(fluoromethoxy)-6-hydroxy-2-methyl-5-[(2E,4E)-3-methyl-5-[(1R,2R,6R)-1,2,6-trimethyl-3-oxocyclohexyl]penta-2,4-dien-1-yl]benzaldehyde [Example 1](600 mg, 1.37 mmol) and hydroxyamine hydrochloride (93.5 mg, 1.35 mmol, 0.98 equiv) in pyridine (6 mL) was placed in a 100-mL round-bottom flask. The mixture was stirred for 2 h at room temperature. The resulting mixture was concentrated under vacuum to give (2R,3R,4R)-3-[(1E,3E)-5-[3-chloro-2-(fluoromethoxy)-6-hydroxy-5-[(1E)-(hydroxyimino)methyl]-4-methylphenyl]-3-methylpenta-1,3-dien-1-yl]-2,3,4-trimethylcyclohexan-1-one (500 mg, crude) as yellow oil.

Step 2

A solution of (2R,3R,4R)-3-[(1E,3E)-5-[3-chloro-2-(fluoromethoxy)-6-hydroxy-5-[(1E)-(hydroxyimino)methyl]-4-methylphenyl]-3-methylpenta-1,3-dien-1-yl]-2,3,4-trimethylcyclohexan-1-one (500 mg, 1.11 mmol) and ethyl 2-(aminooxy)acetate oxalic acid salt (925 mg, 4.42 mmol, 4.00 equiv) in pyridine (6 mL) was placed in a 100-mL round-bottom flask. The mixture was stirred for 1 h at room temperature. The resulting mixture was concentrated under vacuum to give resulted in of ethyl 2-([[(1E,2R,3R,4R)-3-[(1E,3E)-5-[3-chloro-2-(fluoromethoxy)-6-hydroxy-5-[(1E)-(hydroxyimino)methyl]-4-methylphenyl]-3-methylpenta-1,3-dien-1-yl]-2,3,4-trimethylcyclohexylidene]amino]oxy)acetate (550 mg, crude) as yellow solid.

Step 3

A mixture of ethyl 2-([[(1E,2R,3R,4R)-3-[(1E,3E)-5-[3-chloro-2-(fluoromethoxy)-6-hydroxy-5-[(1E)-(hydroxyimino)methyl]-4-methylphenyl]-3-methylpenta-1,3-dien-1-yl]-2,3,4-trimethylcyclohexylidene]amino]oxy)acetate (550 mg, 0.99 mmol), lithium hydroxide (853 mg, 35.62 mmol) in tetrahydrofuran (6 mL) and water (2 mL) was placed in a 100-mL round-bottom flask. The resulting solution was stirred for 1 h at room temperature. The mixture was concentrated under vacuum. The resulting mixture was extracted with ethyl acetate (10 mL×3) and the organic layer was combined, then concentrated under vacuum. The residue was purified by Prep-HPLC with the following condition to give 2-([[(1E,2R,3R,4R)-3-[(1E,3E)-5-[3-chloro-2-(fluoromethoxy)-6-hydroxy-5-[(1E)-(hydroxyimino)methyl]-4-methylphenyl]-3-methylpenta-1,3-dien-1-yl]-2,3,4-trimethylcyclohexylidene]amino]oxy)acetic acid (242.2 mg, 46%, Compound 27) as a solid.

Prep-HPLC condition (Prep_HPLC_MC1): Column: XBridge Shield RP18 OBD Column, 5 um, 19*150 mm; Mobile Phase A: Waters (0.1% FA), Mobile Phase B: ACN; Flow rate: 20 mL/min; Gradient: 56% B to 80% B in 8 min; Detector: 254 nm.

LC-MS (ES, m z): $[M+H]^+$: 525, $[M+Na-H]^+$: 547

H-NMR (300 MHz, $CD_3OD$, ppm): δ 8.56 (S, 1H), 5.89 (d, J=16.2 Hz, 1H), 5.72 (s, 1H), 5.54 (s, 1H), 5.44-5.33 (m, 2H), 4.48 (s, 2H), 3.56 (d, J=7.2 Hz, 2H), 3.39-3.32 (m, 1H), 2.43 (s, 3H), 2.19 (q, J=6.6 Hz, 1H), 1.86 (s, 3H), 1.77-1.59 (m, 3H), 1.25-1.48 (m, 1H), 0.84 (d, J=6.0 Hz, 3H), 0.74-0.69 (m, 6H).

Test Example 1

Effect on Phosphorylation Level of AMPK and ACC in HepG2 Cells.

p-AMPK and p-ACC levels were measured by Western blot analysis using the antibodies for p-AMPK and p-ACC. Following reagents were purchased from the vendors, and the instruments listed below were used.

Reagents: AMPKα (D5A2) rabbit mAb, phospho-acetyl-CoA carboxylase (Ser79) (D7D11) rabbit mAb, anti-rabbit IgG, HRP-linked antibody, and beta-actin (13E5) rabbit mAb were purchased from Cell Signaling Technology. ECL Western Blotting Detection Reagents were purchased from Thermo.

Instruments: Western Blot System (Invitrogen/Bio-Rad), and Imaging System (Cell Biosciences)

Compound Treatment

HepG2 cells were cultured in MEM medium supplemented with 10% FBS at 37° C. and under 5% $CO_2$ condition. HepG2 cells ($1\times10^6$ cells/well) were seeded into 6-well cell culture plates for 24 hr. The cells were starved in serum-free MEM medium (3 ml/well) for 24 hr.

Test Compounds Preparation:

The compounds were dissolved in DMSO to make the stock solution of 5, 25, 50 mM respectively. The compounds were diluted to final concentration in serum-free MEM medium to be 5, 25, and 50 μM.

Metformin Preparation:

Metformin was dissolved in PBS to make the stock concentration as 1M. Metformin was diluted to final concentration in serum-free MEM medium to be 5, and 50 mM The serum-free MEM medium was discarded from each well. 3 ml of 1×compounds was added to each well. Cells were incubated in a 37° C., 5% CO$_2$ incubator for 6 h (Compound 5, Compound 19 and Metformin).

Western Blot Analysis

Total proteins (10 μg) from each sample was loaded to sample well of SDS-PAGE. Electrophoresis was run at 120 V constant voltage until the blue marker reaches the end of the gel. The proteins were transferred to a PVDF membrane using Bio-Rad's Trans blot for 40 min at 300 mA. After transfer, the membrane was blocked with blocking buffer for 2 hr at room temperature. The membrane was incubated with the corresponding primary antibody solution at 4° C. overnight. The membrane was washed for 5 min×3 with 1×TBST and incubated with secondary antibody solution at room temperature for 45 min. The membrane was washed for 5 min×3 with 1×TBST and the detection was conducted with chemiluminescence detection reagents. The results are indicated in FIG. 1.

Test Example 2

Measurement of Solubility in pH4.0 and pH7.4 Phosphate Buffer Solution

1) Preparation of Stock Solutions

The stock solutions of test compounds and positive control compound were prepared in DMSO at the concentration of 30 mM. Diclofenac was used as positive control in the assay.

2) Procedures for Solubility Determination

The stock solution of each compound (10 μL) was placed in order into their proper 96-well rack, followed by adding 990 μL of PBS at pH 4.0 and pH 7.4 into each vial of the cap-less Solubility Sample plate. This study was performed in duplicate. One stir stick was added to each vial and then vials were sealed using a molded PTDE/SIL 96-Well Plate Cover. The Solubility Sample plate was transferred to the Thermomixer Comfort plate shaker and incubated at 25° C. for 2 hours with shaking at 1,100 rpm. After 2 hours incubation, stir sticks were removed using a big magnet and all samples from the Solubility Sample plate were transferred into the filter plate. All the samples were filtered by using the vacuum manifold. The filtered samples were diluted with methanol.

3) Samples Analyzed by LC-MS/MS:

The LC system comprised a Shimadzu liquid chromatograph separation system equipped with degasser DGU-20A3, solvent delivery unit LC-20AD, system controller CBM-20A, column oven CTO-10ASVP and CTC Analytics HTC PAL System. Mass spectrometric analysis was performed using an API 4000 instrument from AB Inc (Canada) with an ESI interface. The data acquisition and control system were created using Analyst 1.6 software from ABI Inc. The results of the measurements are indicated in Table 2.

TABLE 2

| compound number | Solubility (μM) | |
|---|---|---|
| | pH 4.0 PBS | pH 7.4 PBS |
| 13 | 18 | 0.01 |
| 15 | 54 | 0.29 |
| 17 | 39 | 0.04 |
| 19 | 148 | 23.7 |
| 20 | 186 | 0.32 |
| 21 | 168 | 0.003 |
| 22 | 29 | 0.01 |
| 26 | 192 | 12.3 |

TABLE 2-continued

| compound number | Solubility (μM) | |
|---|---|---|
| | pH 4.0 PBS | pH 7.4 PBS |
| 27 | 165 | 315 |
| MAC | <0.08 | 0.07 |
| compound #13 in WO2004/074236 | converted to MAC | 0.02 |

PBS: phosphate buffer solution (2 hr incubation)

Test Example 3

Determination of Stability Against Mouse and Human Microsomes

Pooled human liver microsomes (Cat. 452161; Lot. 23418) were purchased from Corning and pooled male mouse liver microsomes (Cat. M1000; Lot. 1210302) were purchased from Xenotech. Microsomes were stored at −80° C. prior to use. 40 μL of ultra-pure H$_2$O was used instead of NADPH solution in the negative control. The negative control was used to exclude the misleading factor that was resulted from instability of chemical itself. Samples with NADPH were prepared in duplicate. Negative controls were prepared in singlet.

The reaction was started with the addition of 4 μL of 200 μM compound solution to each master solution to get the final concentration of 2 μM. Verapamil was used as positive control in the assay. Aliquots of 50 μL were taken from the reaction solution at 0, 15, 30, 45 and 60 min. The reaction was stopped by addition of 4 volumes of cold acetonitrile with IS (200 nM imipramine, 200 nAM labetalol and 2 μM ketoprofen). Samples were centrifuged at 3,220 g for 40 minutes. Aliquot of 90 μL of the supernatant was mixed with 90 μL of ultra-pure H$_2$O and then was used for LC-MS/MS analysis. Results are shown in Table 3 by indicating remaining % of the test compound after 60 minutes incubation with liver microsomes from human and mouse in the presence of NADPH.

TABLE 3

| compound number | Liver microsome stability remaining % after 60 min incubation with NADPH | |
|---|---|---|
| | human LM | mouse LM |
| 3 | 74 | 58 |
| 4 | 67 | 47 |
| 5 | 86 | 88 |
| 7 | 71 | 71 |
| 8 | 100 | 89 |
| 9 | 100 | 83 |
| 10 | 83 | 63 |
| 11 | 81 | 56 |
| 14 | 99 | 88 |
| 15 | 88 | 79 |
| 16 | 56 | 76 |
| 17 | 76 | 55 |
| 18 | 86 | 59 |
| 19 | 94 | 89 |
| 21 | 100 | 80 |
| 23 | 74 | 98 |
| 25 | 66 | 39 |
| 27 | 99 | 97 |
| MAC | 2 | 6 |

Test Example 4

PK profiles of Compound 19 in the blood were analyzed by LC/MS/MS after single dose administration of the test compounds in SD rats.

Figure 2:
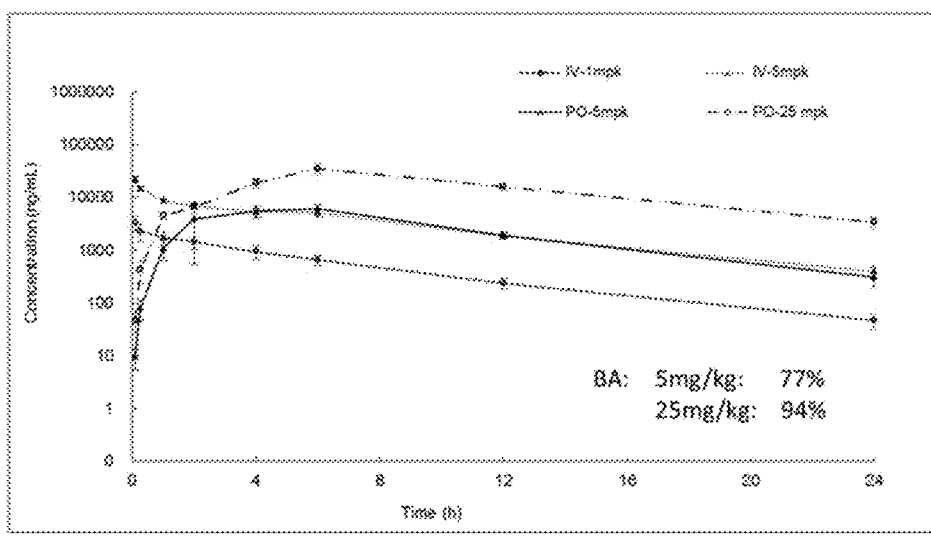
FIG. 2 shows pharmacokinetic profile of Compound 19 in SD rats.

Test animal: SD rat (n=3/group)
Vehicle: 10 v/v % DMSO and 90 v/v % PEG400
Dose (single): iv/1 and 5 mg/kg, po/5 and 25 mg/kg
Analytical instrument and condition: LC/MS/MS instrument [LC: Shimazu, MS: AB API4000 (ion source: ESI)], LC column: XSELECT™ CSH™ C18 2.5 m (2.1×50 mm), mobile phase: 5% acetonitrile (0.1% formic acid) and 95% acetonitrile (0.1% formic acid).
The results are shown in FIG. 2.

Test Example 5

The anti-proliferative activities of the compounds against 6 human cancer cell lines were determined by CellTiterGlo assay kit. All cells were obtained from ATCC and cultured as recommended by the vendor. Cells were assayed in exponential growth phase. Sample solution was prepared by 3-fold serial dilution from 30 mM stock for 10 doses in DMSO. Antiproliferative activities were measured by CellTiterGlo assay kit according to the protocol after cells were incubated for 96 hrs in a 37° C., 5% $CO_2$ incubator.

On the $4^{th}$ day of incubation, i) 15 μl reagent (CelltiterGlo assay kit) was added per well and plate was shaken (avoiding light) for 2 mins on a plate shaker, ii) the plate was kept (avoiding light) in room temperature for 30 min, and iii) the luminescence value was recorded by Multiplate reader. The results are shown in Table 4.

TABLE 4

Antiproliferative activities (IC50: μM)

| compound number | A549 | HT29 | BxPC-3 | LNCaP | MDA-MB-231 | U87-MG |
|---|---|---|---|---|---|---|
| 4 | 4.3 | 6.4 | 11.4 | 4.2 | 5.1 | 9.1 |
| 5 | 2.7 | 2.8 | 3.2 | 1.8 | 2.6 | 5.5 |
| 7 | 6.5 | 10 | 12.8 | 7.2 | 6.8 | 13.1 |
| 12 | 2.9 | 2.8 | 2.3 | 0.9 | 5.8 | 3.6 |
| 13 | 2 | 3.6 | 2.2 | 0.8 | 5.3 | 3 |
| 15 | 6.7 | 7 | 1.7 | 4.2 | 4.8 | 4.4 |
| 17 | 6.8 | 5.2 | 1.7 | 4.1 | 5 | 4.5 |
| 19 | 22.3 | 22.5 | 17 | 14.6 | 47.4 | 20.4 |
| 20 | 4.8 | 2.7 | 2.3 | 1.9 | 4.1 | 2.3 |
| 21 | 5.3 | 5 | 1.7 | 3.8 | 4.3 | 3.1 |
| 22 | 1.9 | 3.8 | 2.7 | 1.1 | 6 | 3.2 |

Test Example 6

An efficacy study was conducted by using Compound 19 (Cmpd 19) with CT26 syngeneic mouse model. Female BALB/c mice (Vital River, Beijing, China) of 7 to 9 weeks old with body weight between 19 and 21 g were used. Each mouse was inoculated subcutaneously on the right flank with CT26 tumor cells ($2\times10^5$) in 0.1 mL of PBS for tumor development. On Day 5 after tumor inoculation, mice were randomized into groups. Each group consisted of 10 tumor-bearing mice. The treatment with Cmpd 19 was then started on Day 5. The treatments were made to the tumor-bearing mice according to the study design shown in Table 5.

TABLE 5

Groups and Treatments

| Group | Drug | Dose (mg/kg) | Route | Regimen |
|---|---|---|---|---|
| 1 | Vehicle | — | p.o. | Once a day x 18 |
| 2 | Anti PD-1 antibody | 10 | i.p. | Once 6 days x 3 |
| 3 | Cmpd 19 | 50 | p.o. | Once a day x 18 |
| 4 | Cmpd 19 | 25 | p.o. | Once a day x 18 |
| 5 | Cmpd 19 + | 50 | p.o. | Once a day x 18 |
| | Anti PD-1 antibody | 10 | i.p. | Once 6 days x 3 |
| 6 | Cmpd 19 + | 25 | p.o. | Once a day x 18 |
| | Anti PD-1 antibody | 10 | i.p. | Once 6 days x 3 |

As an anti PD-1 antibody, anti-mouse PD-1 antibody (CD279, Clone: RMP1-14, Catalog #: BE0146 from Bio X Cell) was used. Formulation of each drug is summarized in Table 6.

TABLE 6

Formulation

| Compounds | Preparation |
|---|---|
| Vehicle | 95% PEG400, 5% Tween80 |
| Anti PD-1 | PBS |
| Cmpd 19 | 95% PEG400, 5% Tween80 |

Figure 3:
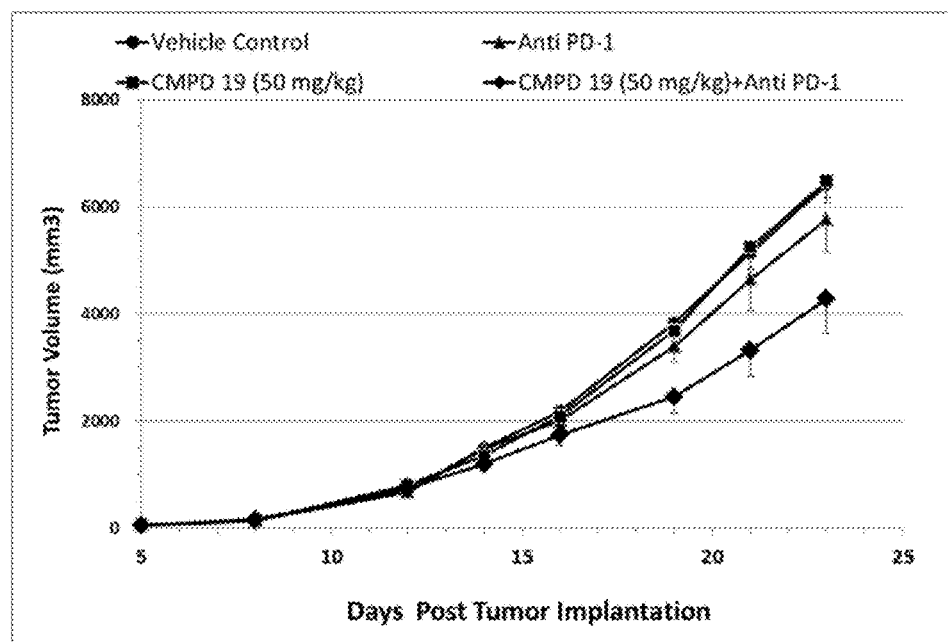
FIG. 3 shows the results of assay conducted in Test Example 6 indicating tumor growth curve for G1, G3, and G9.

The measurement of tumor size was conducted three times weekly with calipers, and the tumor volume ($mm^3$) is estimated using the formula: $TV=(a\times b^2)/2$, where "a" and "b" are long and short diameters of a tumor, respectively. The TVs were used for calculation of the tumor growth inhibition (TGI, an indicator of antitumor effectiveness), using formula: $TGI=(1-T/C)\times100\%$, where "T" and "C" are the mean relative volumes (% tumor growth) of the tumors in the treated and the control groups. Data were analyzed using GraphPad Software and represented as the mean value±SD in FIG. 3 in which error bars are shown. The p values were assessed using One-Way ANOVA Dunnett test and vehicle control (G1) as control group. A case with p<0.05 was considered as statistically significant. The tumor growth inhibitions were summarized in Table 7.

TABLE 7

Antitumor Activities of Different Treatment Groups in CT26 Tumor Model

| Treatment | Tumor volume ($mm^3$, on Day 23) | TGI (%) | P value vs. vehicle control |
|---|---|---|---|
| G1: Vehicle | 6,425 ± 352 | — | — |
| G2: Anti PD-1 | 5,769 ± 625 | 10.4 | 0.393 |
| G3: Cmpd 19 (50 mg/kg) | 6,483 ± 310 | −1.4 | 0.940 |
| G4: Cmpd 19 (25 mg/kg) | 6,056 ± 689 | 6.5 | 0.630 |
| G5: Cmpd 19 (50 mg/kg) + Anti PD-1 | 4,278 ± 645 | 33.2 | 0.006 |
| G6: Cmpd 19 (25 mg/kg) + Anti PD-1 | 5,054 ± 582 | 21.4 | 0.076 |

Tumor growth curves for G1: Vehicle, G3: Anti PD-1 antibody, G5: Cmpd 19 (50 mg/kg), and G7: Cmpd 19 (50 mg/kg)+Anti PD-1 antibody are plotted in FIG. 3.

Overall, administration of a single drug, namely administration of anti PD-1 antibody, Cmpd 19 (50 mg/kg) or Cmpd 19 (25 mg/kg) shows a minor or no antitumor activity with TGI values of 10.4% (p=0.393), −1.4% (p=0.940) and 6.5% (p=0.630) respectively. The combination treatment of anti-PD-1 antibody with Cmpd 19 (50 mg/kg) produces a significant antitumor activity. Moreover, the TGI values for these combinations are calculated to be 33.2% (p=0.006). While the combination treatment of anti-PD-1 antibody with Cmpd 19 (25 mg/kg) produced a moderate trend antitumor activity with TGI of 21.4% (p=0.076).

The invention claimed is:

1. A method for treating or preventing a cancer, comprising administrating to a subject in need thereof a therapeutically effective amount of a compound represented by formula (I):

(I)

wherein
$R^1$ is formyl, or —CH=N—O—Y, in which Y is a hydrogen atom or $C_{1-6}$ alkyl;
$R^2$ is $C_{1-6}$ alkyl that may be substituted with 1 to 5 fluorine atoms;
$R^3$ is a hydrogen atom or $C_{1-6}$ alkyl;
$R^4$ is hydroxy, $C_{1-6}$ alkylamino, $C_{3-7}$ cycloalkylamino, or 3- to 7-membered heterocycloalkylamino which contains —O—, —S—, —$NR^6$—, —SO— or —$SO_2$— as a ring atom, or
$R^3$ and $R^4$ together with the carbon atom to which they are attached form >C=N—O—Z;
Z is a hydrogen atom, $C_{1-6}$ alkyl, —$CO(CH_2)_n$—$R^5$ or —$(CH_2)_n$—$R^5$;
n is an integer selected from 1 to 4;
$R^5$ is —$CO_2R^6$, —$CONH_2$, —$CONR^7R^8$, —$OCONR^7R^8$, —$SO_2NR^7R^8$, —$SO_2R^9$, hydroxy, —$NHSO_2R^9$, or —$NR^7R^8$;
$R^6$, $R^7$ and $R^8$ are each independently selected from a group consisting of a hydrogen atom, $C_{1-6}$ alkyl, and $C_{3-7}$ cycloalkyl; or $R^7$ and $R^8$ together with the nitrogen atom to which they are attached form a nitrogen-containing 3- to 7-membered heterocyclic ring which may further contain —O—, —S—, —$NR^6$—, —SO— or —$SO_2$— as a ring atom, in which the heterocyclic ring may be substituted with one or more substituents selected from hydroxy and $C_{1-6}$ alkyl;
$R^9$ is $C_{1-6}$ alkyl, or $C_{3-7}$ cycloalkyl;
a pharmaceutically acceptable salt or a solvate thereof, in combination with administration of an immune checkpoint inhibitor.

2. The method according to claim 1, wherein $R^4$ is selected from the group consisting of hydroxy, methylamino, ethylamino, cyclopropylamino, and oxetan-3-ylamino.

3. The method according to claim 1, wherein $R^3$ and $R^4$ together with the carbon atom to which they are attached form >C=N—O—Z in which Z is selected from the group consisting of a hydrogen atom, $C_{1-6}$ alkyl, —$CH_2CO_2R^6$, morpholinoethyl, piperazinylethyl, N-methyl-piperazinylethyl, and N,N-dimethylamino-ethyl.

4. The method according to claim 2, wherein $R^1$ is formyl.

5. The method according to claim 2, wherein $R^1$ is —CH=N—OH.

6. The method according to claim 2, wherein $R^1$ is —CH=N—OMe.

7. The method according to claim 1, wherein the compound represented by formula (I) is selected from the group consisting of
3-chloro-6-hydroxy-5-((2E,4E)-5-((1R,2R,6R)-3-hydroxy-1,2,3,6-tetramethylcyclohexyl)-3-methylpenta-2,4-dien-1-yl)-4-methoxy-2-methylbenzaldehyde,
3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde,
(E)-3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde oxime,
3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde oxime,
3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde,
[(1E,2R,3R,4R)-3-[(1E,3E)-5-(3-chloro-5-formyl-6-hydroxy-2-methoxy-4-methylphenyl)-3-methylpenta-1,3-dien-1-yl]-2,3,4-trimethylcyclohexylidene]amino 2-(dimethylamino)acetate,
(E)-3-chloro-6-hydroxy-5-((2E,4E)-5-((1R,2R,3S,6R)-3-hydroxy-1,2,3,6-tetramethylcyclohexyl)-3-methylpenta-2,4-dien-1-yl)-4-methoxy-2-methylbenzaldehyde oxime,
(E)-3-chloro-6-hydroxy-4-methoxy-5-((2E,4E)-5-((1R,2R,6R,E)-3-(methoxyimino)-1,2,6-trimethylcyclohexyl)-3-methylpenta-2,4-dien-1-yl)-2-methylbenzaldehyde O-methyl oxime,
(E)-3-chloro-4-(fluoromethoxy)-6-hydroxy-5-((2E,4E)-5-((1R,2R,6R,E)-3-(methoxyimino)-1,2,6-trimethylcyclohexyl)-3-methylpenta-2,4-dien-1-yl)-2-methylbenzaldehyde O-methyl oxime,
(E)-3-chloro-6-hydroxy-5-((2E,4E)-5-((1R,2R,6R,E)-3-(hydroxyimino)-1,2,6-trimethylcyclohexyl)-3-methylpenta-2,4-dien-1-yl)-4-methoxy-2-methylbenzaldehyde O-methyl oxime,
(E)-3-chloro-4-(fluoromethoxy)-6-hydroxy-5-((2E,4E)-5-((1R,2R,6R,E)-3-(hydroxyimino)-1,2,6-trimethylcyclohexyl)-3-methylpenta-2,4-dien-1-yl)-2-methylbenzaldehyde O-methyl oxime,
3-chloro-4-(fluoromethoxy)-6-hydroxy-2-methyl-5-((2E,4E)-3-methyl-5-((1R,2R,6R,E)-1,2,6-trimethyl-3-(2-morpholinoethoxyimino)cyclohexyl)penta-2,4-dien-1-yl)benzaldehyde,
3-chloro-5-((2E,4E)-5-((1R,2R,6R)-3-(cyclopropylamino)-1,2,6-trimethylcyclohexyl)-3-methylpenta-2,4-dien-1-yl)-4-(fluoromethoxy)-6-hydroxy-2-methylbenzaldehyde,
(E)-3-chloro-6-hydroxy-5-((2E,4E)-5-((1R,2R,3S,6R)-3-hydroxy-1,2,3,6-tetramethylcyclohexyl)-3-methylpenta-2,4-dien-1-yl)-4-methoxy-2-methylbenzaldehyde O-methyl oxime,
(E)-3-chloro-5-((2E,4E)-5-((1R,2R,6R,E)-3-(2-(dimethylamino)ethoxyimino)-1,2,6-trimethylcyclohexyl)-3-methylpenta-2,4-dien-1-yl)-6-hydroxy-4-methoxy-2-methylbenzaldehyde O-methyl oxime,
(E)-3-chloro-6-hydroxy-4-methoxy-2-methyl-5-((2E,4E)-3-methyl-5-((1R,2R,6R,E)-1,2,6-trimethyl-3-(2- morpholinoethoxyimino)cyclohexyl)penta-2,4-dien-1-yl)benzaldehyde O-methyl oxime,
(E)-3-chloro-6-hydroxy-4-methoxy-2-methyl-5-((2E,4E)-3-methyl-5-((1R,2R,6R,E)-1,2,6-trimethyl-3-(2-(4-methylpiperazin-1-yl)ethoxyimino)-cyclohexyl)penta-2,4-dien-1-yl)benzaldehyde O-methyl oxime,
ethyl 2-([[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetate,
2-([[(1E,2R,3R,4R)-3-[(1E,3E)-5-[3-chloro-6-hydroxy-2-methoxy-5-[(1E)-(methoxyimino)methyl]-4-methylphenyl]-3-methylpenta-1,3-dien-1-yl]-2,3,4-trimethylcyclohexylidene]amino]oxy)acetic acid,
3-chloro-5-((2E,4E)-5-((1R,2R,6R)-3-(ethylamino)-1,2,6-trimethylcyclohexyl)-3-methylpenta-2,4-dien-1-yl)-6-hydroxy-4-methoxy-2-methylbenzaldehyde,
(E)-3-chloro-5-((2E,4E)-5-((1R,2R,6R)-3-(ethylamino)-1,2,6-trimethylcyclohexyl)-3-methylpenta-2,4-dien-1-yl)-6-hydroxy-4-methoxy-2-methylbenzaldehyde O-methyl oxime,
3-chloro-5-((2E,4E)-5-((1R,2R,6R)-3-(cyclopropylamino)-1,2,6-trimethylcyclohexyl)-3-methylpenta-2,4-dien-1-yl)-6-hydroxy-4-methoxy-2-methylbenzaldehyde,
(E)-3-chloro-5-((2E,4E)-5-((1R,2R,6R)-3-(cyclopropylamino)-1,2,6-trimethylcyclohexyl)-3-methylpenta-2,4-dien-1-yl)-6-hydroxy-4-methoxy-2-methylbenzaldehyde O-methyl oxime,
2-[(2E,4E)-5-[(1R,2R,6R)-3-amino-1,2,6-trimethylcyclohexyl]-3-methylpenta-2,4-dien-1-yl]-4-chloro-3-methoxy-6-[(1E)-(methoxyimino)methyl]-5-methylphenol,
(E)-3-chloro-6-hydroxy-4-methoxy-2-methyl-5-((2E,4E)-3-methyl-5-((1R,2R,6R)-1,2,6-trimethyl-3-(oxetan-3-ylamino)cyclohexyl)penta-2,4-dien-1-yl)benzaldehyde O-methyl oxime,
2-([[(1E,2R,3R,4R)-3-[(1E,3E)-5-[3-chloro-6-hydroxy-2-fluoromethoxy-5-formyl-4-methylphenyl]-3-methylpenta-1,3-dien-1-yl]-2,3,4-trimethylcyclohexylidene]amino]oxy)acetic acid,
2-([[(1E,2R,3R,4R)-3-[(1E,3E)-5-[3-chloro-6-hydroxy-2-methoxy-5-[(1E)-(hydroxyimino)methyl]-4-methylphenyl]-3-methylpenta-1,3-dien-1-yl]-2,3,4-trimethylcyclohexylidene]amino]oxy)acetic acid,
2-([[(1E,2R,3R,4R)-3-[(1E,3E)-5-[3-chloro-2-methoxy-6-hydroxy-5-[(1E)-(hydroxyimino)methyl]-4-methylphenyl]-3-methylpenta-1,3-dien-1-yl]-2,3,4-trimethylcyclohexylidene]amino]oxy)acetic acid,
and pharmaceutically acceptable salts thereof.

8. The method according to claim 1, wherein the immune checkpoint inhibitor is selected from anti-CTLA4 antibodies, anti-PD-1 antibodies and anti-PD-L1 antibodies.

9. The method according to claim 1, wherein the immune checkpoint inhibitor is an anti-PD-1 antibody.

10. The method according to claim 1, wherein the immune checkpoint inhibitor is an anti-PD-L1 antibody.

11. The method according to claim 3, wherein $R^1$ is formyl.

12. The method according to claim 3, wherein $R^1$ is —CH=N—OH.

13. The method according to claim 3, wherein $R^1$ is —CH=N—OMe.

* * * * *